US009433538B2

(12) United States Patent
Pagel et al.

(10) Patent No.: US 9,433,538 B2
(45) Date of Patent: Sep. 6, 2016

(54) METHODS AND APPARATUS FOR APPLICATION OF NESTED ZERO WASTE EAR TO TRAVELING WEB AND FORMATION OF ARTICLES USING A DUAL CUT SLIP UNIT

(71) Applicant: CURT G. JOA, INC., Sheboygan Falls, WI (US)

(72) Inventors: Tyler W Pagel, Grafton, WI (US); Brian Jankuski, Glenbeulah, WI (US); Robert Herberg, Sheboygan Falls, WI (US); Peter J Jenquin, Plymouth, WI (US); Robert E Andrews, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 131 days.

(21) Appl. No.: 13/650,625

(22) Filed: Oct. 12, 2012

(65) Prior Publication Data
US 2013/0037201 A1 Feb. 14, 2013

Related U.S. Application Data

(63) Continuation-in-part of application No. 12/925,033, filed on Oct. 12, 2010, which is a continuation-in-part of application No. 12/798,520, filed on Apr. 5, 2010, now Pat. No. 8,172,977, application No. 13/650,625,
(Continued)

(51) Int. Cl.
*A61F 13/15* (2006.01)
(52) U.S. Cl.
CPC ... *A61F 13/15723* (2013.01); *A61F 13/15756* (2013.01); *A61F 13/15804* (2013.01); *Y10T 156/1075* (2015.01)

(58) Field of Classification Search
CPC ....... B32B 38/04; B32B 38/06; B32B 38/10; A61F 13/15723; A61F 13/15756; A61F 13/15804
USPC ........ 156/250, 252, 256, 259, 263, 264, 265
See application file for complete search history.

(56) References Cited

U.S. PATENT DOCUMENTS

| 135,145 A | 1/1873 | Murphy |
| 293,353 A | 2/1884 | Purvis |

(Continued)

FOREIGN PATENT DOCUMENTS

| BE | 1007854 | 11/1995 |
| CA | 1146129 | 5/1983 |

(Continued)

OTHER PUBLICATIONS

International Search Report dated Mar. 9, 2012 regarding EP Application No. 11184738.0, 6 pages.
(Continued)

*Primary Examiner* — Mark A Osele
*Assistant Examiner* — Christopher C Caillouet
(74) *Attorney, Agent, or Firm* — Ryan Kromholz & Manion, S.C.

(57) ABSTRACT

The present invention provides a method of providing a disposable product with zero waste ear formation and attaching the ears to a running chassis web. A cut/slip operation is performed on an incoming web carried by a transfer drum, and the cut/slip pieces are further divided and next separated by a second transfer drum and bonded to incoming webs.

6 Claims, 50 Drawing Sheets

Related U.S. Application Data which is a continuation-in-part of application No. 12/151,667, filed on May 8, 2008, now Pat. No. 8,106,972, application No. 13/650,625, which is a continuation-in-part of application No. 12/806,891, filed on Aug. 24, 2010, now Pat. No. 8,293,056, which is a continuation-in-part of application No. 11/436,274, filed on May 18, 2006, now Pat. No. 7,780,052.

(60) Provisional application No. 61/547,474, filed on Oct. 14, 2011, provisional application No. 61/212,011, filed on Apr. 6, 2009, provisional application No. 61/212,619, filed on Apr. 14, 2009, provisional application No. 60/928,305, filed on May 9, 2007.

(56) References Cited

U.S. PATENT DOCUMENTS

| | | |
|---|---|---|
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 9/1967 | Joa |
| 3,356,092 A | 12/1967 | Joa |
| 3,360,103 A | 12/1967 | Joa |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |

(56) References Cited

U.S. PATENT DOCUMENTS

| | | |
|---|---|---|
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,220,237 A | 9/1980 | Mohn |
| 4,222,533 A | 9/1980 | Pongracz |
| 4,223,822 A | 9/1980 | Clitheroe |
| 4,231,129 A | 11/1980 | Winch |
| 4,234,157 A | 11/1980 | Hodgeman et al. |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,479,836 A | 10/1984 | Dickover et al. |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,826,499 A | 5/1989 | Ahr |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,917,746 A | 7/1990 | Kons |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,676 A | 1/1994 | Rooyakkers et al. |
| 5,308,345 A | 5/1994 | Herrin |
| 5,328,438 A | 7/1994 | Crowley |
| 5,334,446 A | 8/1994 | Quantrille et al. |
| 5,340,424 A | 8/1994 | Matsushita |
| 5,353,909 A | 10/1994 | Mukai |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,435,971 A | 7/1995 | Dyckman |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Hermann |
| 5,540,647 A | 7/1996 | Weiermann et al. |

(56) References Cited

U.S. PATENT DOCUMENTS

| | | |
|---|---|---|
| 5,540,796 A | 7/1996 | Fries |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 3,288,037 A | 11/1996 | Burnett |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| 5,685,873 A | 11/1997 | Bruemmer |
| RE35,687 E | 12/1997 | Igaue et al. |
| 5,693,165 A | 12/1997 | Schmitz |
| 5,699,653 A | 12/1997 | Hartman et al. |
| 5,705,013 A * | 1/1998 | Nease et al. ............... 156/260 |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,759,340 A | 6/1998 | Boothe et al. |
| 5,766,389 A | 6/1998 | Brandon et al. |
| 5,779,689 A | 7/1998 | Pfeifer et al. |
| 5,788,797 A | 8/1998 | Herrin et al. |
| 5,817,199 A | 10/1998 | Brennecke et al. |
| 5,827,259 A | 10/1998 | Laux et al. |
| 5,829,164 A | 11/1998 | Kotischke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,904,675 A | 5/1999 | Laux et al. |
| 5,932,039 A | 8/1999 | Popp et al. |
| 5,938,193 A | 8/1999 | Bluemle et al. |
| 5,938,652 A | 8/1999 | Sauer |
| 5,964,390 A | 10/1999 | Borresen et al. |
| 5,964,970 A | 10/1999 | Woolwine et al. |
| 5,971,134 A | 10/1999 | Trefz et al. |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,171,432 B1 | 1/2001 | Brisebois |
| 6,183,576 B1 | 2/2001 | Couillard et al. |
| 6,193,054 B1 | 2/2001 | Henson et al. |
| 6,193,702 B1 | 2/2001 | Spencer |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,639 B1 | 7/2001 | Sauer |
| 6,264,784 B1 | 7/2001 | Menard et al. |
| 6,276,421 B1 | 8/2001 | Valenti et al. |
| 6,276,587 B1 | 8/2001 | Boerresen |
| 6,284,081 B1 | 9/2001 | Vogt et al. |
| 6,287,409 B1 | 9/2001 | Stephany |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,336,922 B1 | 1/2002 | VanGompel et al. |
| 6,336,923 B1 | 1/2002 | Fujioka et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,544,375 B1 | 4/2003 | Schmitz |
| 6,547,909 B1 | 4/2003 | Butterworth |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,656,309 B1 | 12/2003 | Parker et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,682,626 B2 | 1/2004 | Mlinar et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Guha et al. |
| 6,758,109 B2 | 7/2004 | Nakakado |
| 6,766,817 B2 | 7/2004 | da Silva |
| 6,808,582 B2 | 10/2004 | Popp et al. |
| D497,991 S | 11/2004 | Otsubo et al. |
| 6,811,019 B2 | 11/2004 | Christian et al. |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,869,494 B2 | 3/2005 | Roessler et al. |
| 6,875,202 B2 | 4/2005 | Kumasaka et al. |
| 6,884,310 B2 | 4/2005 | Roessler et al. |
| 6,893,528 B2 | 5/2005 | Middelstadt et al. |
| 6,913,718 B2 | 7/2005 | Ducker |
| 6,918,404 B2 | 7/2005 | Dias da Silva |

(56) References Cited

U.S. PATENT DOCUMENTS

| | | |
|---|---|---|
| 6,976,521 B2 | 12/2005 | Mlinar |
| 6,978,486 B2 | 12/2005 | Zhou et al. |
| 7,017,321 B2 | 3/2006 | Salvoni |
| 7,017,820 B1 | 3/2006 | Brunner |
| 7,045,031 B2 | 5/2006 | Popp et al. |
| 7,047,852 B2 | 5/2006 | Franklin et al. |
| 7,066,586 B2 | 6/2006 | da Silva |
| 7,069,970 B2 | 7/2006 | Tomsovic et al. |
| 7,077,393 B2 | 7/2006 | Ishida |
| 7,130,710 B2 | 10/2006 | Popp et al. |
| 7,172,666 B2 | 2/2007 | Groves et al. |
| 7,175,584 B2 | 2/2007 | Maxton et al. |
| 7,195,684 B2 | 3/2007 | Satoh |
| 7,201,345 B2 | 4/2007 | Werner |
| 7,214,174 B2 | 5/2007 | Allen et al. |
| 7,214,287 B2 | 5/2007 | Shiomi |
| 7,220,335 B2 | 5/2007 | Van Gompel et al. |
| 7,247,219 B2 | 7/2007 | O'Dowd |
| 7,252,730 B2 | 8/2007 | Hoffman et al. |
| 7,264,686 B2 | 9/2007 | Thorson et al. |
| 7,303,708 B2 | 12/2007 | Andrews et al. |
| 7,326,311 B2 | 2/2008 | Krueger et al. |
| 7,332,459 B2 | 2/2008 | Collins et al. |
| 7,374,627 B2 | 5/2008 | McCabe |
| 7,380,213 B2 | 5/2008 | Pokorny et al. |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,695,464 B2 | 4/2010 | Fletcher et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,793,772 B2 | 9/2010 | Schafer |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,922,983 B2 | 4/2011 | Prokash et al. |
| 7,935,296 B2 | 5/2011 | Koele et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 8,062,459 B2 | 11/2011 | Nakakado et al. |
| 8,172,977 B2 | 5/2012 | Andrews et al. |
| 8,176,573 B2 | 5/2012 | Popp et al. |
| 8,182,624 B2 | 5/2012 | Handziak |
| 8,293,056 B2 | 10/2012 | McCabe |
| 2001/0012813 A1 | 8/2001 | Bluemle |
| 2001/0017181 A1 | 8/2001 | Otruba et al. |
| 2001/0035332 A1 | 11/2001 | Zeitler |
| 2001/0042591 A1 | 11/2001 | Milner et al. |
| 2002/0002358 A1* | 1/2002 | Durrance et al. ........ 604/385.01 |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0138064 A1 | 9/2002 | Datta |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0051802 A1 | 3/2003 | Hargett et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0115660 A1 | 6/2003 | Hopkins |
| 2003/0121244 A1 | 7/2003 | Abba |
| 2003/0121614 A1 | 7/2003 | Tabor et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0082931 A1 | 4/2004 | Tani |
| 2004/0087425 A1 | 5/2004 | Ng et al. |
| 2004/0098791 A1 | 5/2004 | Faulks |
| 2004/0112517 A1 | 6/2004 | Groves et al. |
| 2004/0164482 A1 | 8/2004 | Edinger |
| 2004/0167493 A1 | 8/2004 | Jarpenberg et al. |
| 2004/0182213 A1 | 9/2004 | Wagner et al. |
| 2004/0182497 A1 | 9/2004 | Lowrey |
| 2004/0216830 A1 | 11/2004 | Van Eperen |
| 2005/0000628 A1 | 1/2005 | Norrby |
| 2005/0022476 A1 | 2/2005 | Hamer |
| 2005/0056678 A1 | 3/2005 | Nomura et al. |
| 2005/0077418 A1 | 4/2005 | Werner et al. |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0201619 A1 | 9/2006 | Andrews |
| 2006/0224137 A1 | 10/2006 | McCabe et al. |
| 2006/0265867 A1 | 11/2006 | Schaap |
| 2007/0074953 A1 | 4/2007 | McCabe |
| 2007/0131343 A1 | 6/2007 | Nordang |
| 2007/0131817 A1 | 6/2007 | Fromm |
| 2007/0142808 A1* | 6/2007 | Wada et al. ................. 604/385.3 |
| 2008/0210067 A1 | 9/2008 | Schlinz et al. |
| 2008/0223537 A1 | 9/2008 | Wiedmann |
| 2009/0020211 A1 | 1/2009 | Andrews et al. |
| 2009/0126864 A1 | 5/2009 | Tachibana et al. |
| 2009/0198205 A1 | 8/2009 | Malowaniec et al. |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193135 A1 | 8/2010 | Eckstein et al. |
| 2010/0193138 A1 | 8/2010 | Eckstein |
| 2010/0193155 A1 | 8/2010 | Nakatani |
| 2011/0106042 A1 | 5/2011 | Sablone et al. |
| 2012/0123377 A1 | 5/2012 | Back |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2330679 | 9/1999 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| CA | 2699136 | 10/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |

(56) References Cited

FOREIGN PATENT DOCUMENTS

| | | |
|---|---|---|
| EP | 0089106 | 9/1983 |
| EP | 0099732 | 2/1984 |
| EP | 0206208 | 12/1986 |
| EP | 0304140 | 2/1989 |
| EP | 0439897 | 8/1991 |
| EP | 0455231 A1 | 11/1991 |
| EP | 510251 | 10/1992 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1035818 | 4/2002 |
| EP | 1199057 | 4/2002 |
| EP | 1366734 | 12/2003 |
| EP | 1433731 | 6/2004 |
| EP | 1189564 | 3/2005 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 1941853 A1 | 9/2008 |
| EP | 1994919 | 11/2008 |
| EP | 2103427 | 9/2009 |
| EP | 2233116 | 9/2010 |
| EP | 2238955 | 10/2010 |
| EP | 1175880 | 5/2012 |
| EP | 1868821 | 1/2013 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 1467470 | 3/1977 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| JP | 2007-44374 | 2/2007 |
| JP | 2008-161300 | 7/2008 |
| SE | 0602047 | 5/2007 |
| SE | 0601003-7 | 6/2007 |
| SE | 0601145-6 | 10/2009 |
| WO | WO2008155618 | 12/1988 |
| WO | WO93/15248 | 8/1993 |
| WO | WO9403301 | 2/1994 |
| WO | WO97/23398 | 7/1997 |
| WO | WO9732552 | 9/1997 |
| WO | WO9747265 | 12/1997 |
| WO | WO9747810 | 12/1997 |
| WO | WO9821134 | 5/1998 |
| WO | WO98/55298 | 12/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO03/031177 | 4/2003 |
| WO | WO2004007329 | 1/2004 |
| WO | WO2005075163 | 8/2005 |
| WO | WO2006038946 | 4/2006 |
| WO | WO2007029115 | 3/2007 |
| WO | WO2007039800 | 4/2007 |
| WO | WO2007126347 | 11/2007 |
| WO | WO2008001209 | 1/2008 |
| WO | WO2008/015594 | 2/2008 |
| WO | WO2008037281 | 4/2008 |
| WO | WO2008/123348 | 10/2008 |
| WO | WO2010028786 | 3/2010 |
| WO | WO2011101773 | 8/2011 |

OTHER PUBLICATIONS

International Search Report dated Oct. 4, 2013 regarding EP Application No. 12173311.7, 6 pages.

Third Party Observations regarding EP08251662.6, dated Nov. 11, 2014, 9 pages.

European Search Report for Appln. No. 12188581.8, 6 pages, dated Sep. 12, 2014.

* cited by examiner

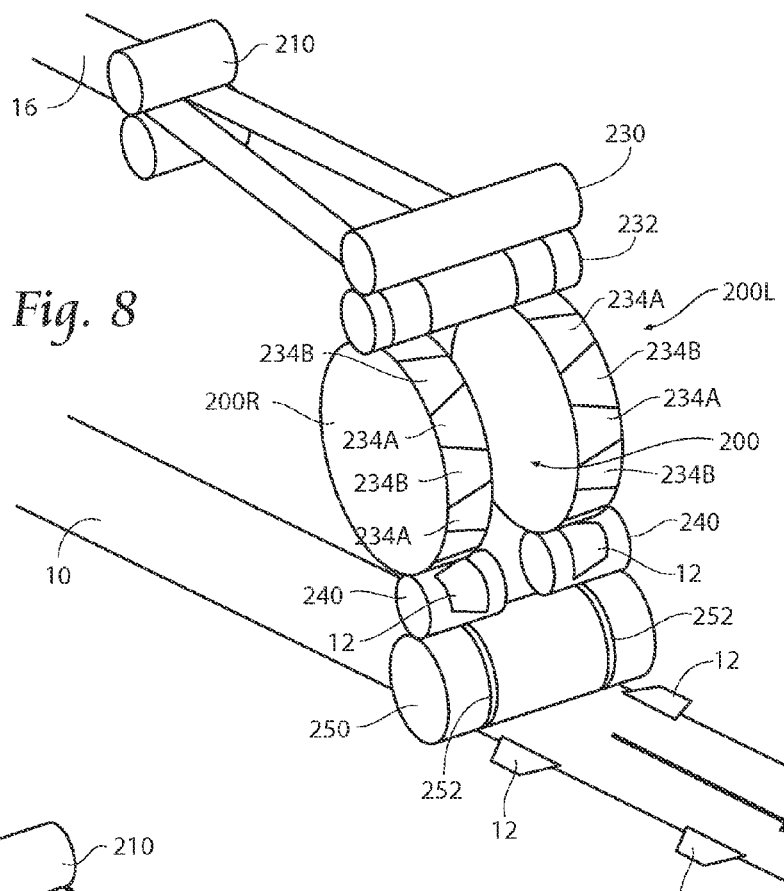
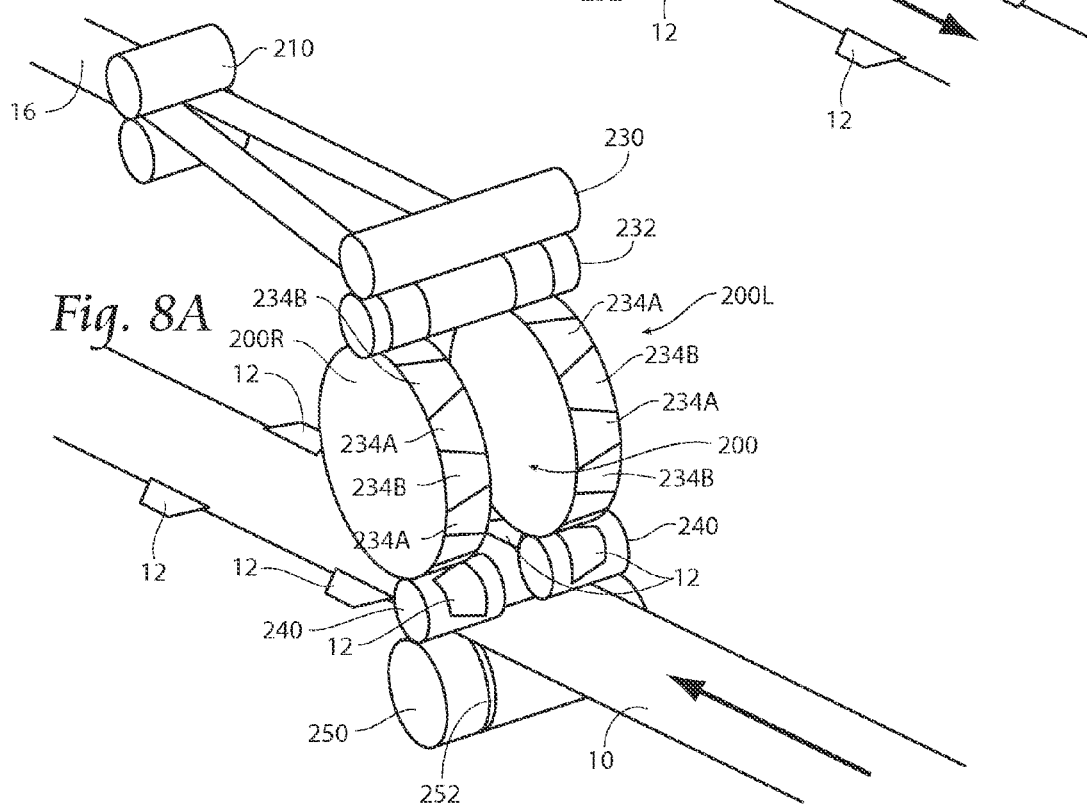

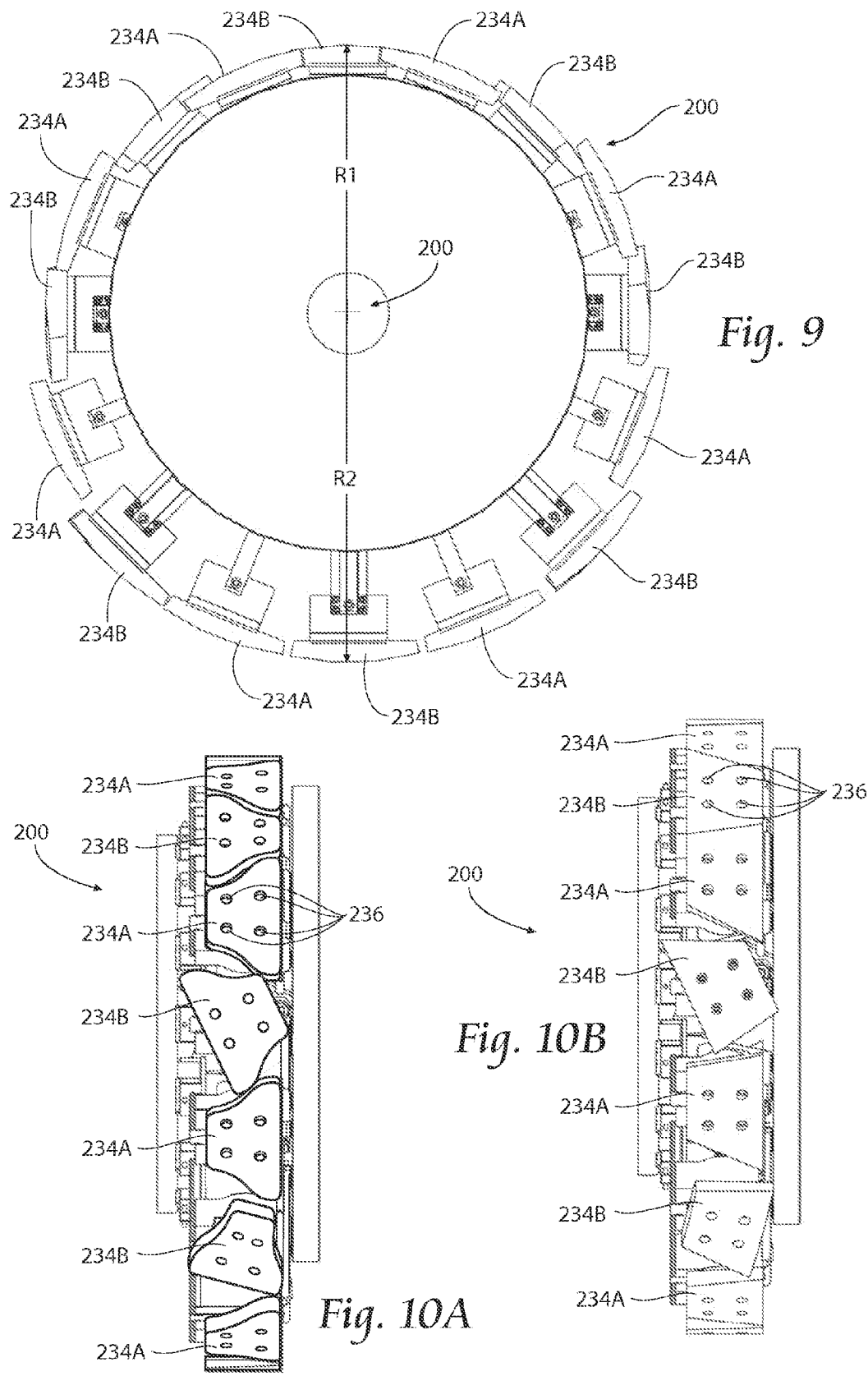

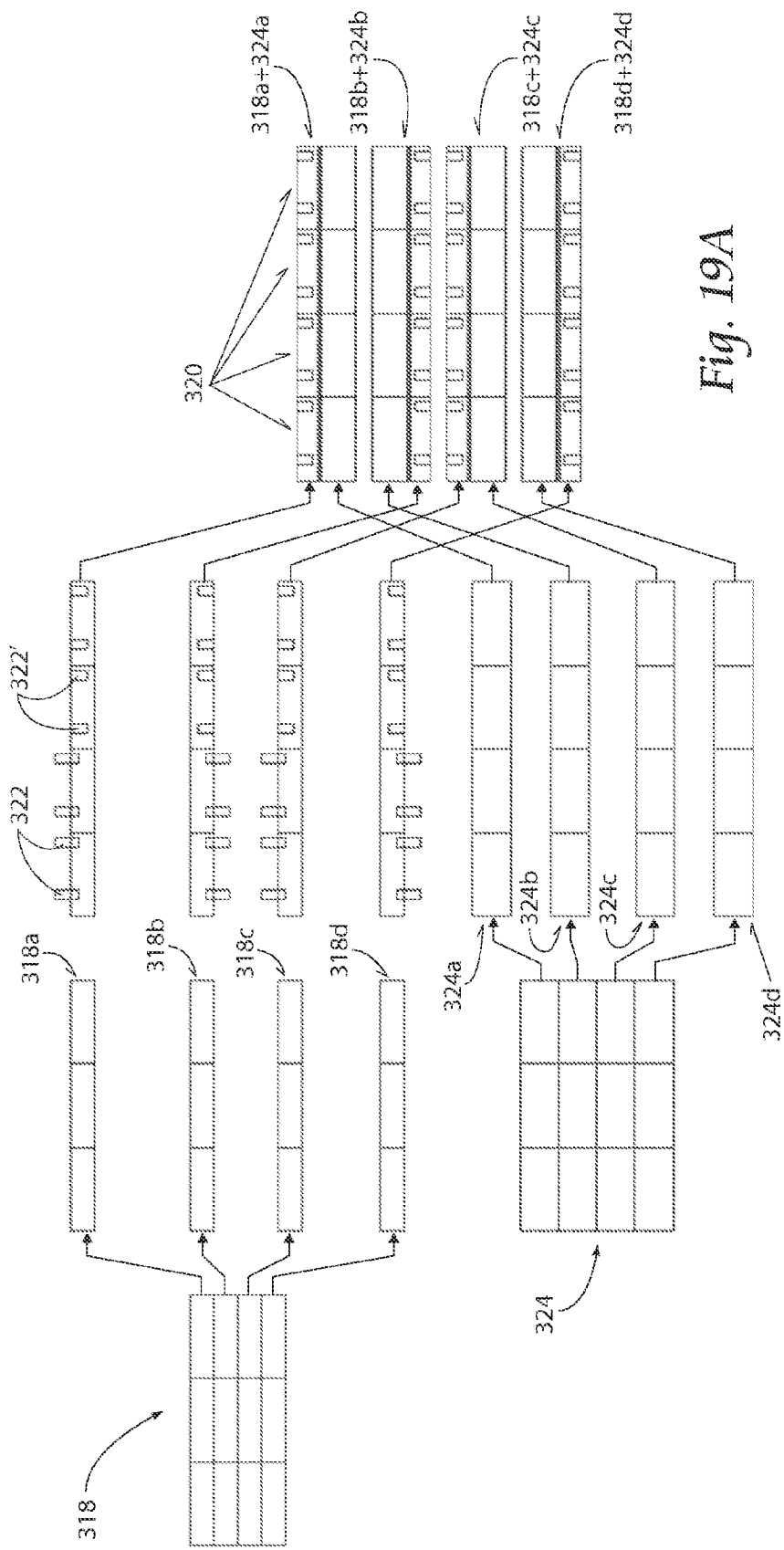

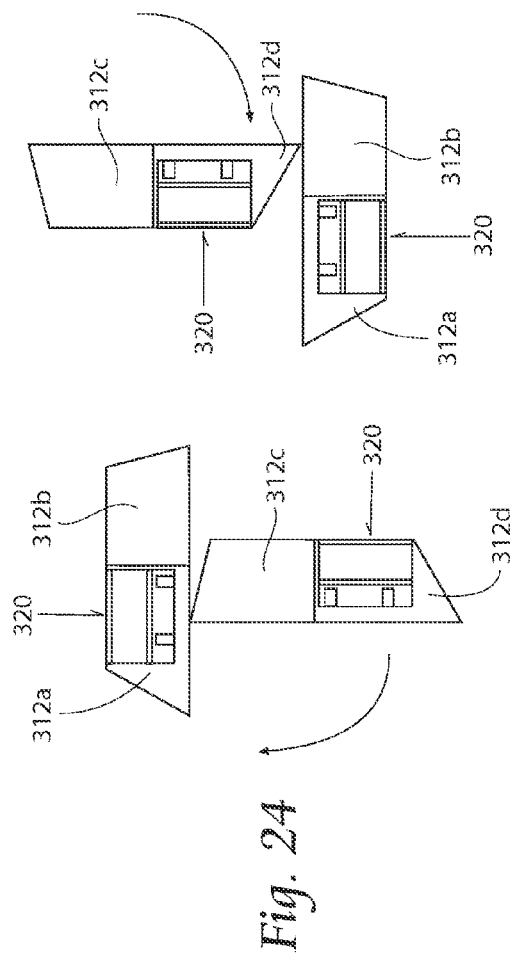
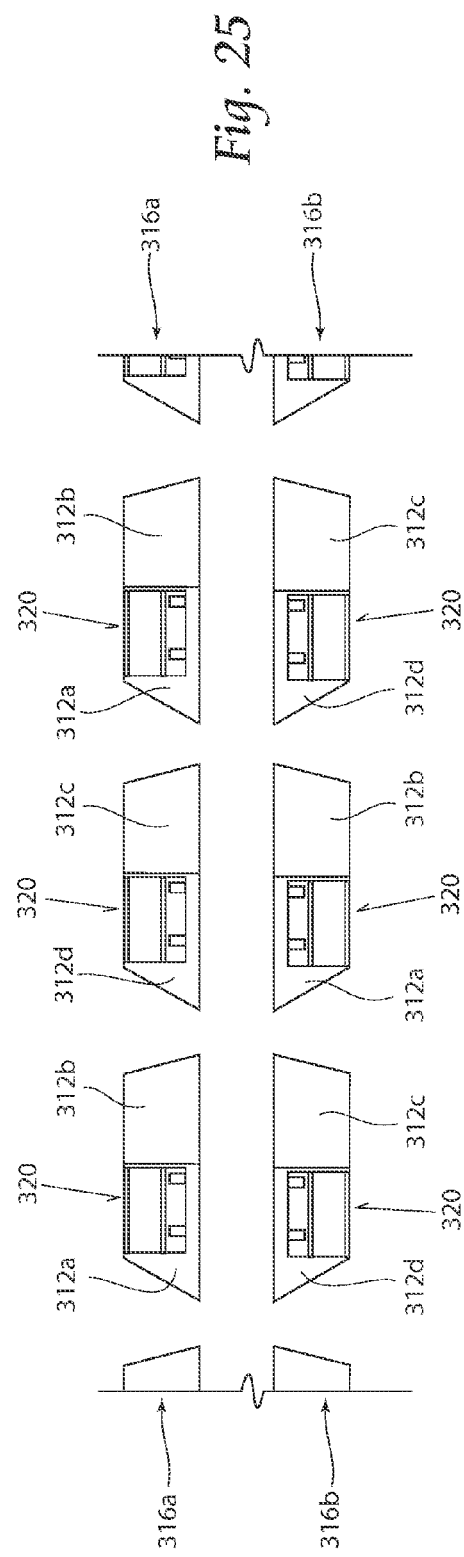
Fig. 24
Fig. 25

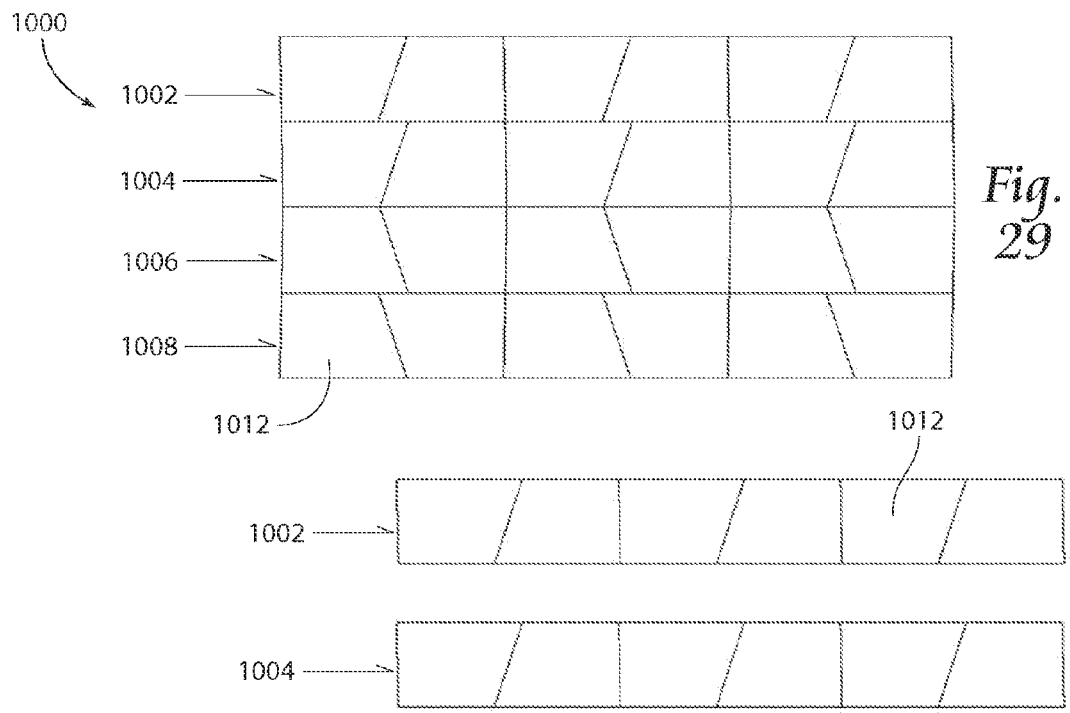
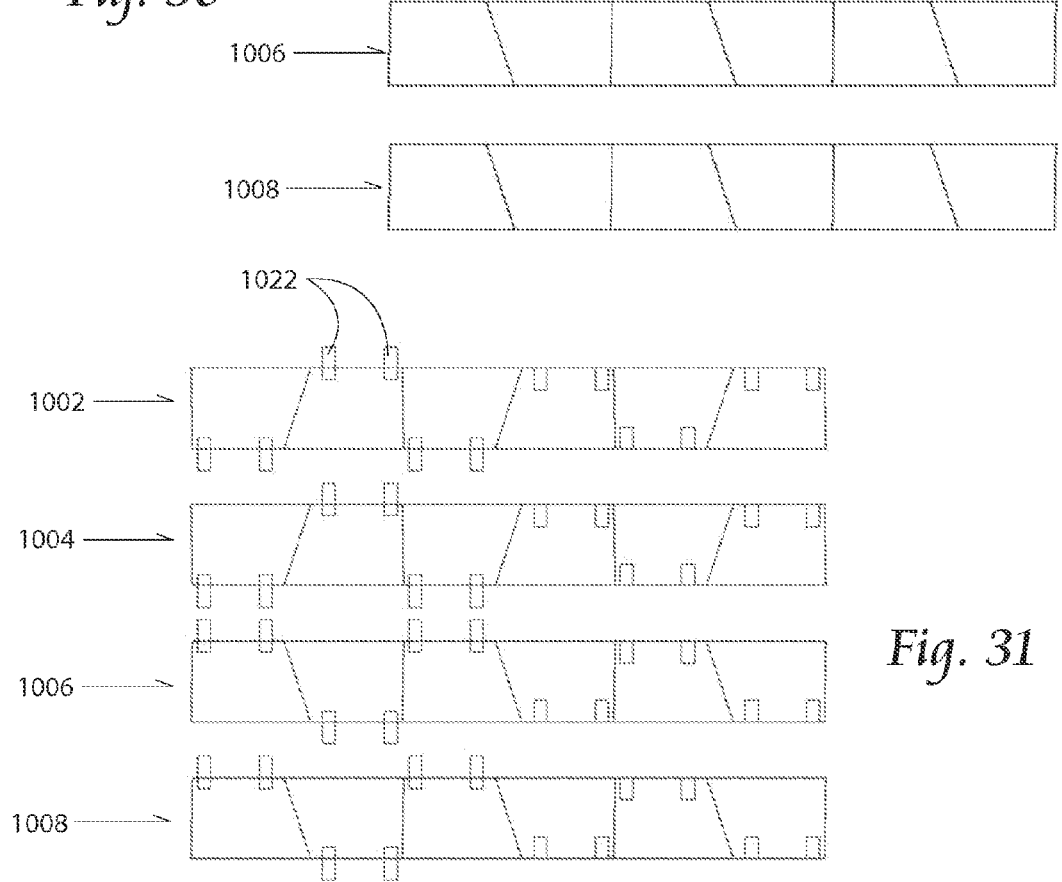

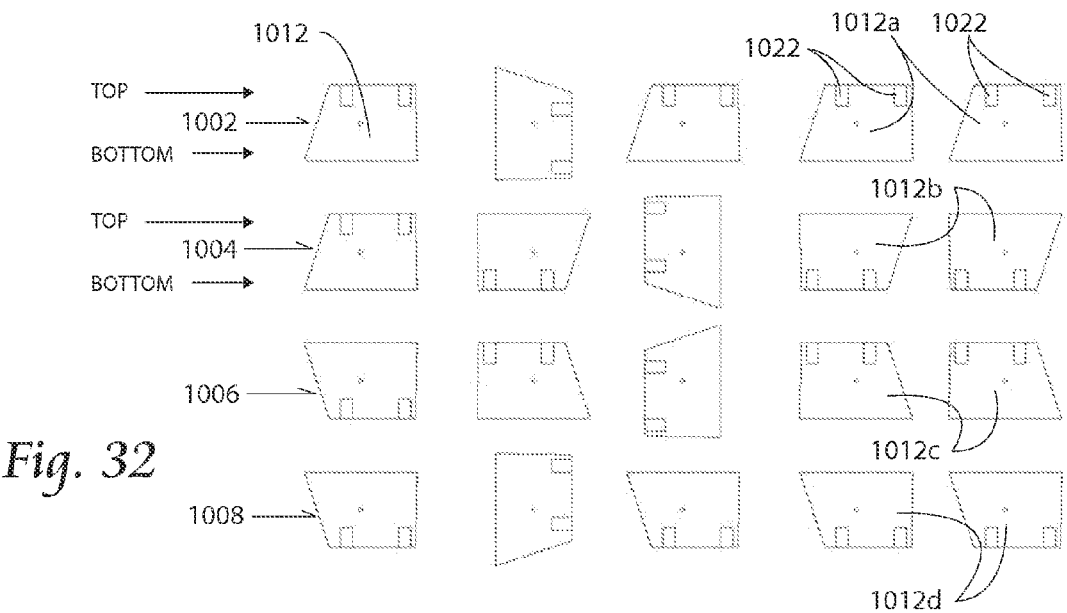
Fig. 32
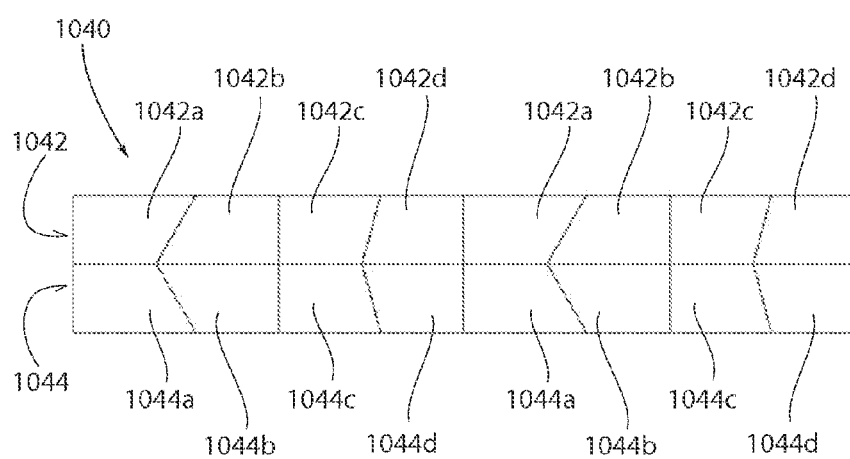
Fig. 33
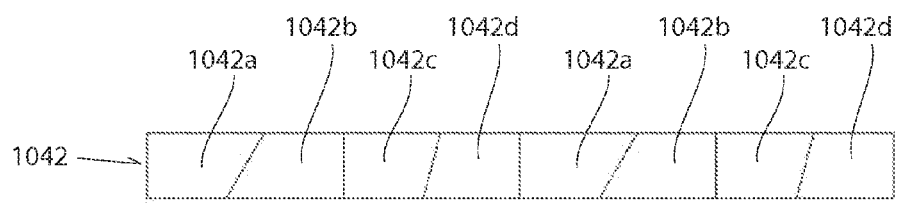
Fig. 34
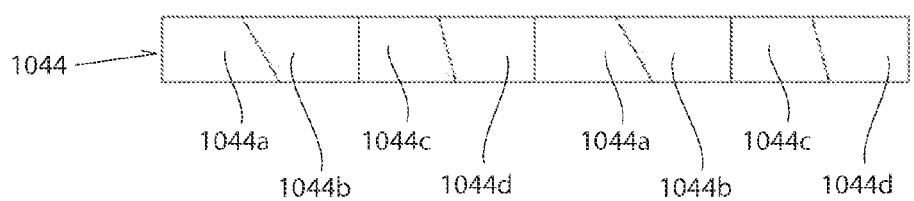

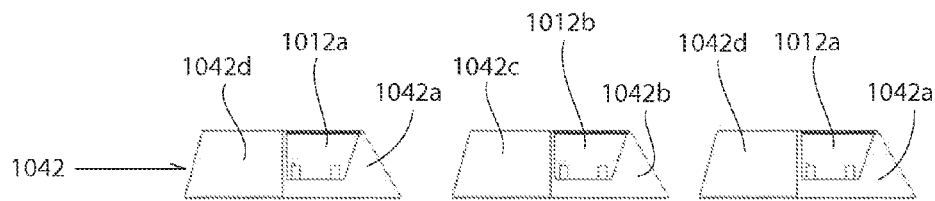
Fig. 38
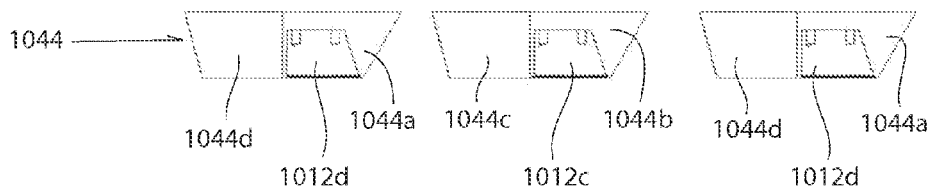
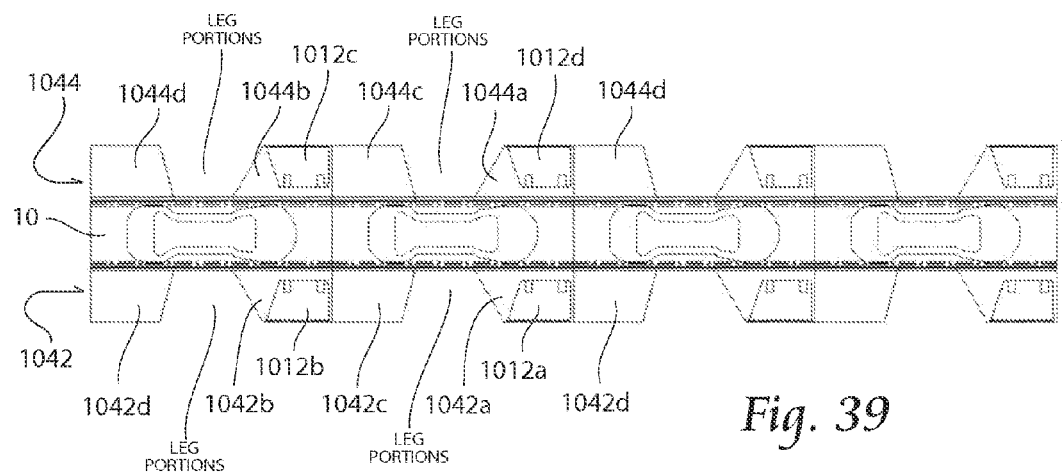
Fig. 39
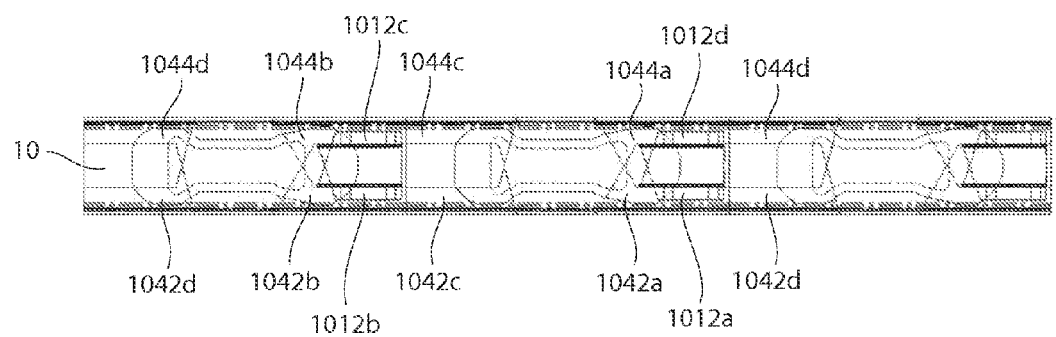
Fig. 40

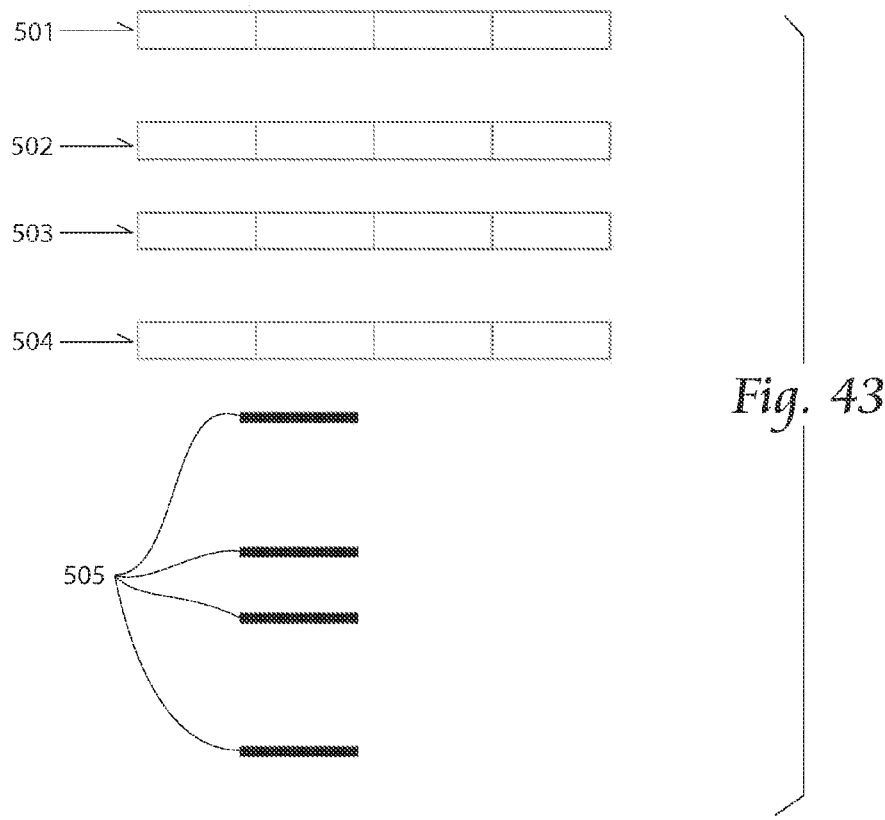
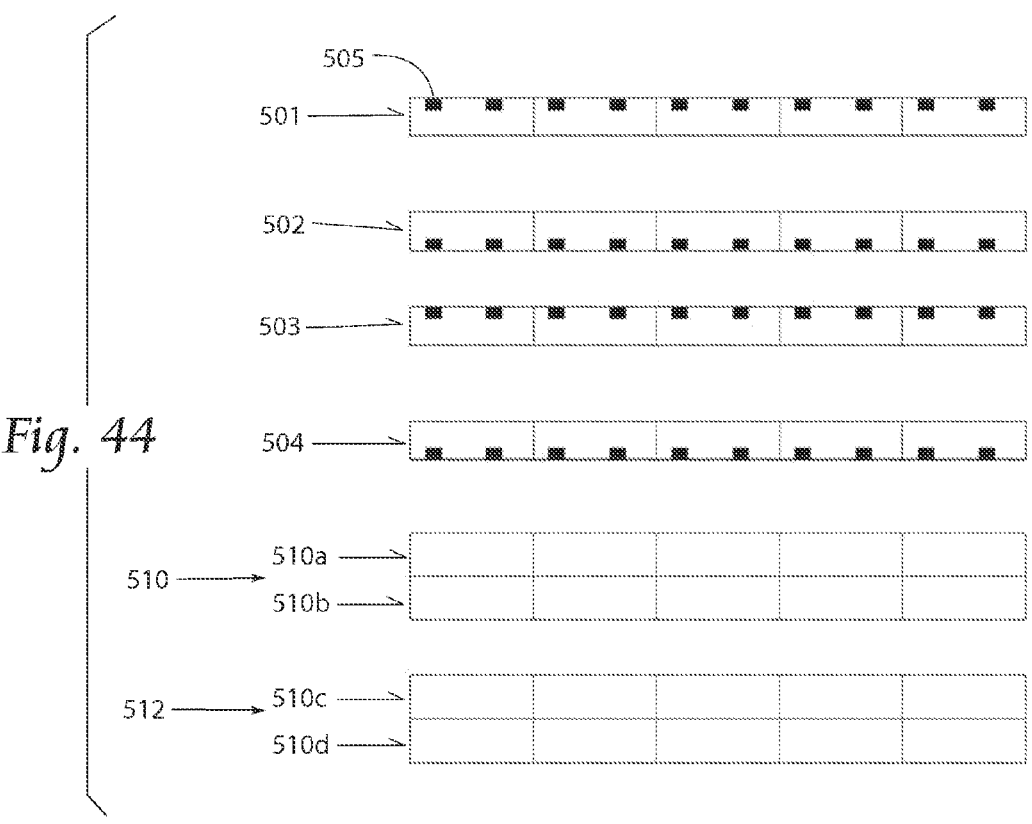

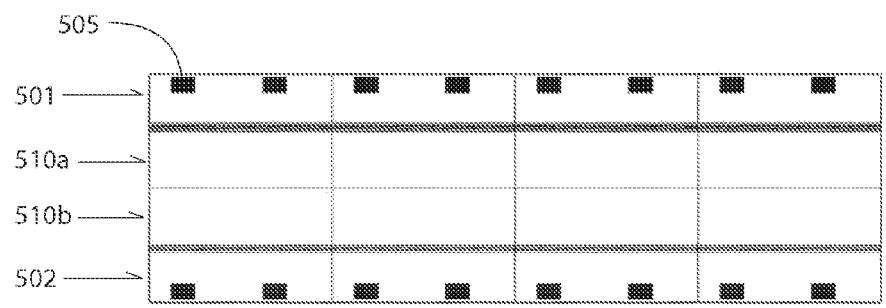
Fig. 45
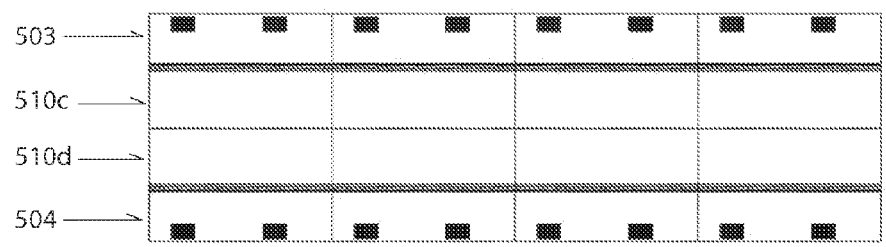
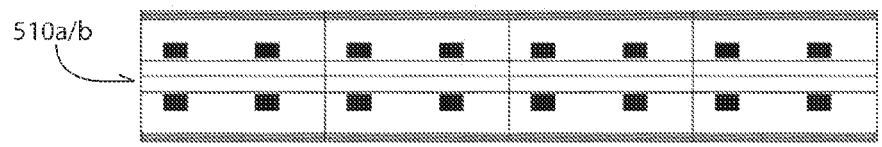
Fig. 46
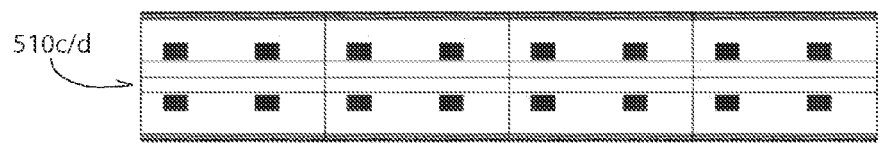

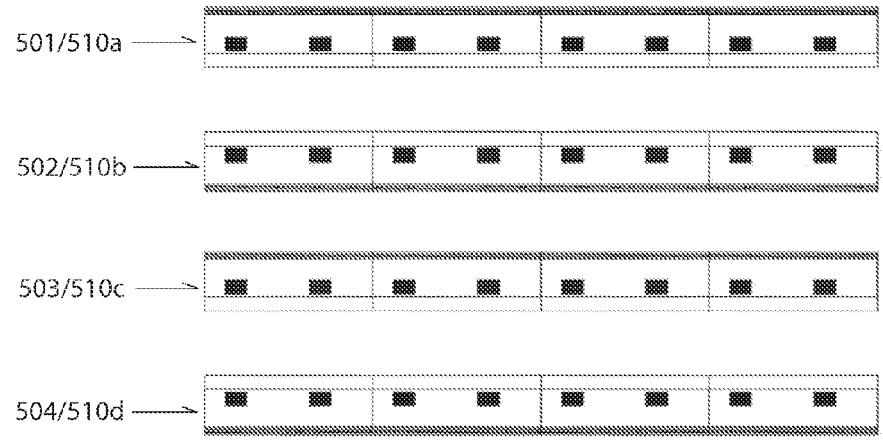
Fig. 47
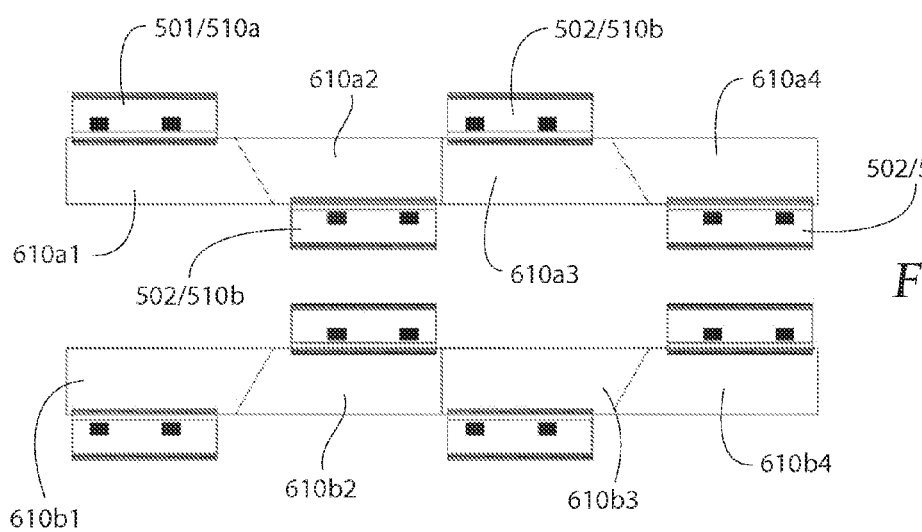
Fig. 48
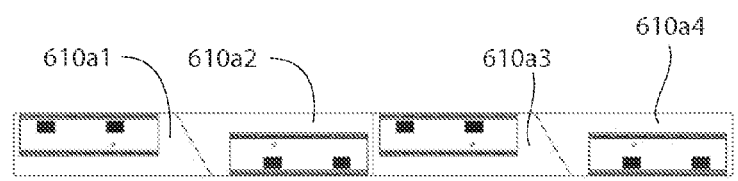
Fig. 49
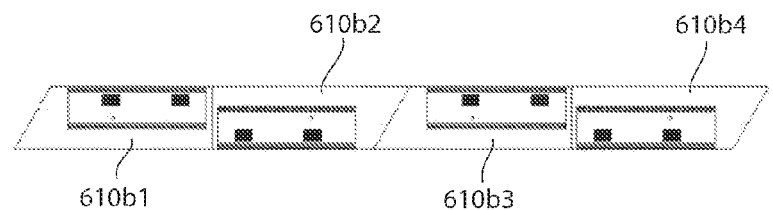

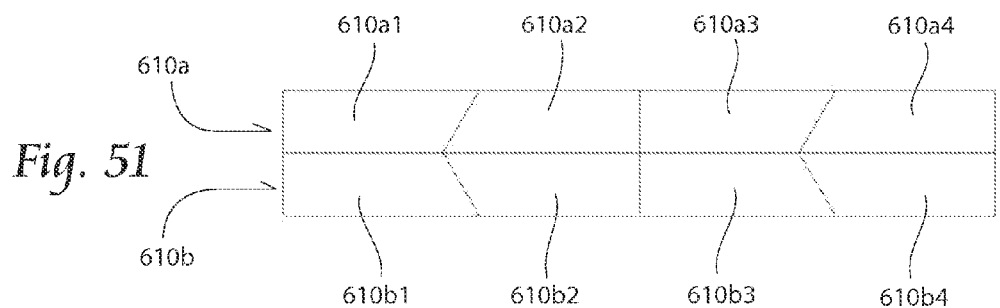
Fig. 51
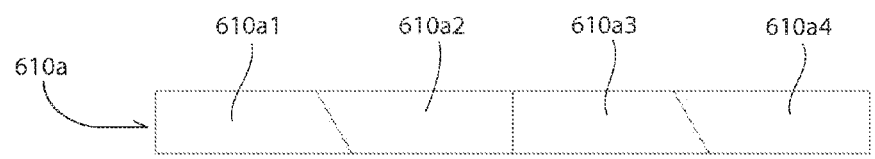
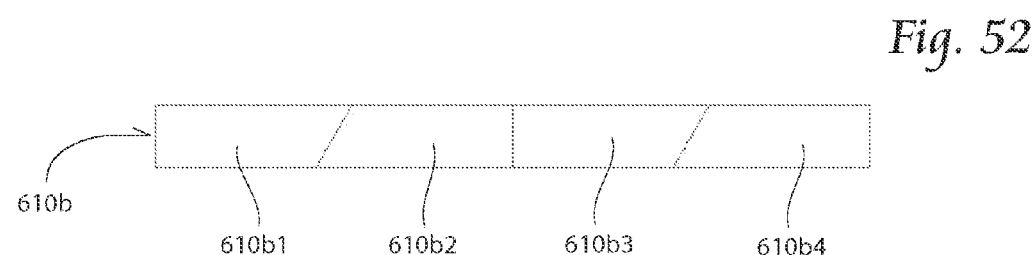
Fig. 52

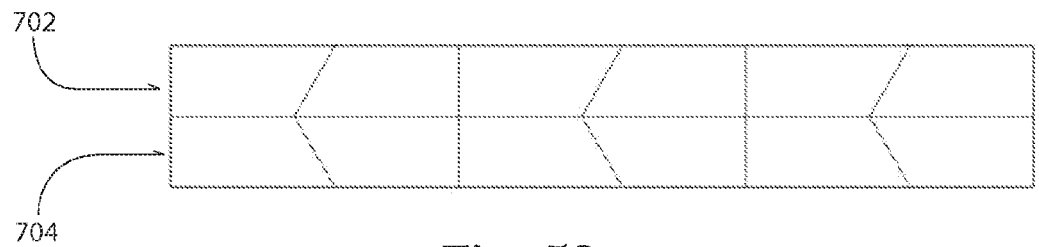
Fig. 53
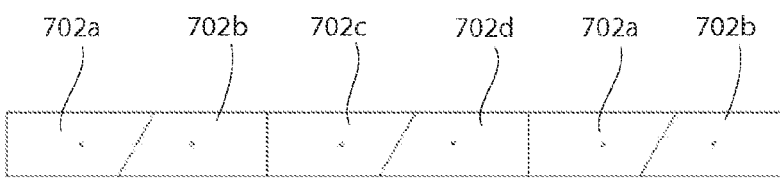
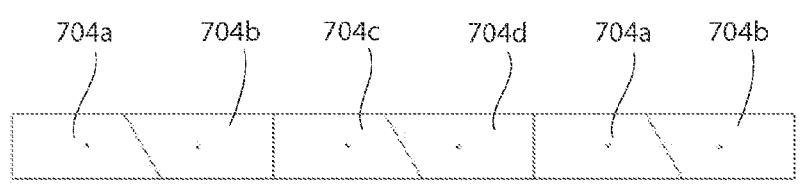
Fig. 54
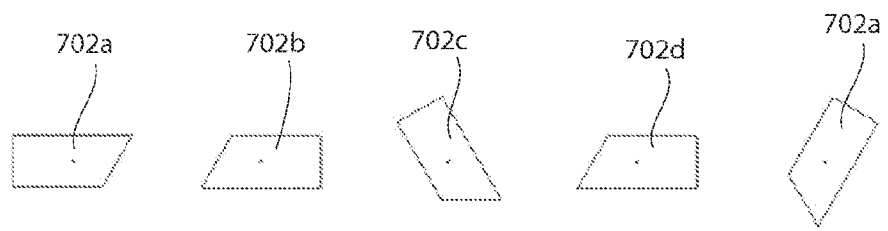
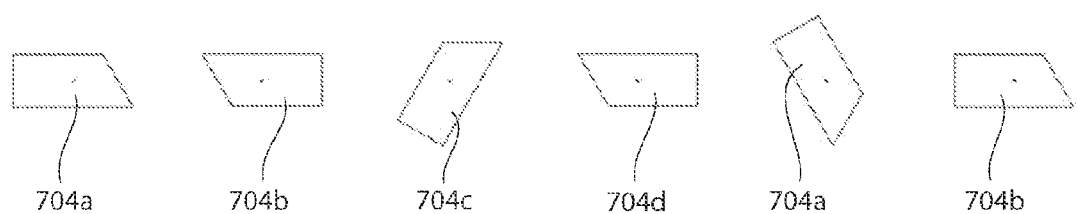
Fig. 55

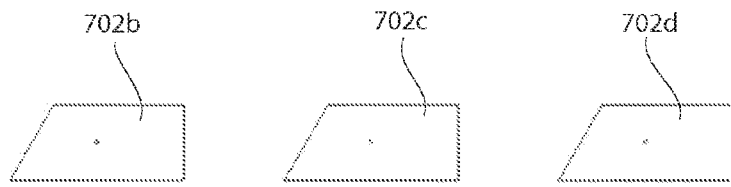
*Fig. 56*
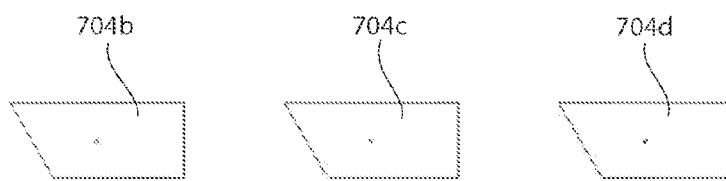
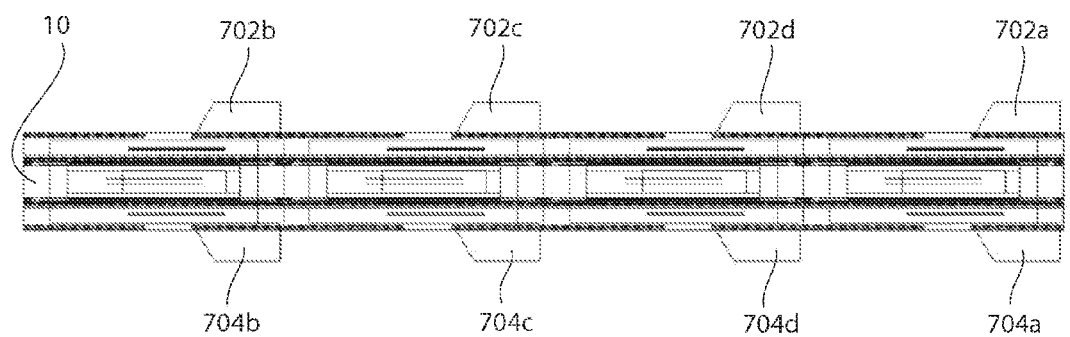
*Fig. 57*
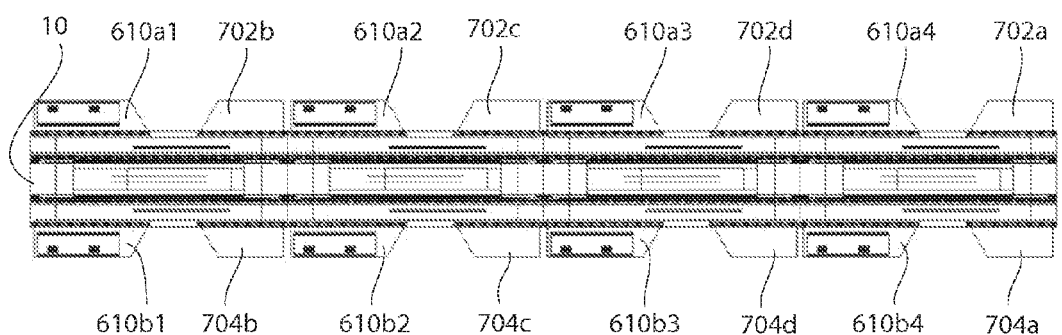
*Fig. 58*

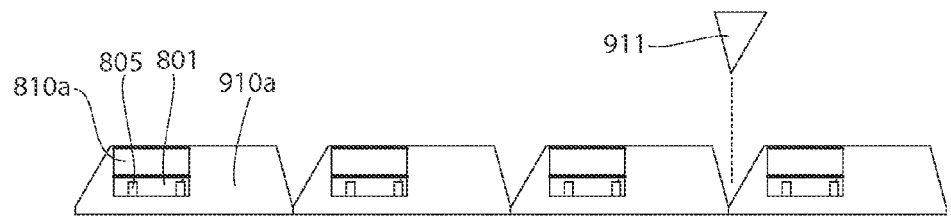
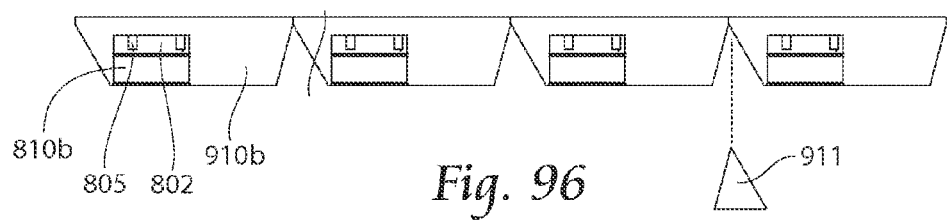
Fig. 96
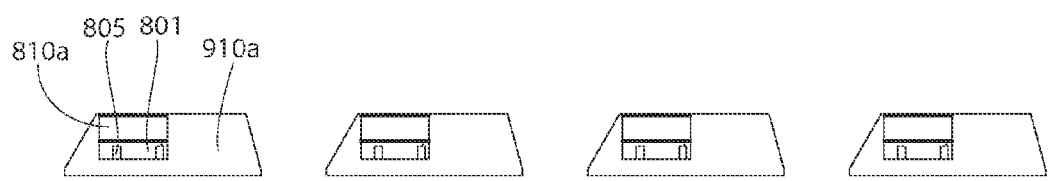
Fig. 97
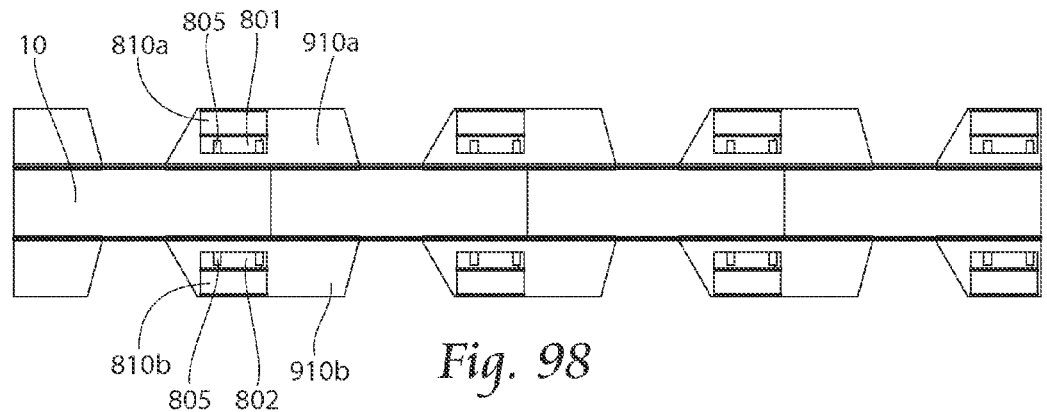
Fig. 98 ically, ears are
secured to the diaper at a first end, and a second free end is
typically equipped with securing means, such as a pressure

METHODS AND APPARATUS FOR APPLICATION OF NESTED ZERO WASTE EAR TO TRAVELING WEB AND FORMATION OF ARTICLES USING A DUAL CUT SLIP UNIT

RELATED APPLICATIONS

This application claims the benefit of co-pending Provisional Patent Application Ser. No. 61/547,474, filed on 14 Oct. 2011. This application is also a continuation-in-part of U.S. application Ser. No. 12/925,033, filed on 12 Oct. 2010, which is a continuation-in-part of U.S. application Ser. No. 12/798,520 filed on 5 Apr. 2010 (now U.S. Pat. No. 8,172,977), which in turn claims the benefit of U.S. Provisional Application Ser. No. 61/212,011 filed on 6 Apr. 2009 and U.S. Provisional Application Ser. No. 61/212,619 filed on 14 Apr. 2009. This application is also a continuation-in-part of application Ser. No. 12/151,667 filed 8 May, 2008 (now U.S. Pat. No. 8,106,972), which claims the benefit of U.S. Provisional Application Ser. No. 60/928,305 filed 9 May 2007. This application is also a continuation-in-part of U.S. application Ser. No. 12/806,891 filed on 24 Aug. 2010 which is a continuation U.S. application Ser. No. 11/436,274, filed on 18 May 2006 (now U.S. Pat. No. 7,780,052).

BACKGROUND OF THE INVENTION

The present invention relates to disposable hygiene products and more specifically, to methods and apparatuses for processing disposable hygiene products. More specifically, the invention relates to cutting and applying segments of one web to attach to a disposable diaper.

The invention disclosed herein also relates to apparatus and methods for waste reduction. Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion. As in many manufacturing operations, waste minimization is a goal in web processing applications, as products having spliced raw materials cannot be sold to consumers. Indeed, due to the rate at which web processing machines run, even minimal waste can cause inefficiencies of scale.

In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, it is beneficial to use up all of incoming rolls, so that a portion of the incoming rolls do not become waste. That objective is accomplished with the present invention When manufacturing hygiene products, such as baby diapers, adult diapers, disposable undergarments, incontinence devices, sanitary napkins and the like, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts a off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web.

Continual improvements and competitive pressures have incrementally increased the operational speeds of disposable diaper converters. As speeds increased, the mechanical integrity and operational capabilities of the applicators had to be improved accordingly.

SUMMARY OF THE INVENTION

The present invention allows for square, and non-square, and preferably trapezoidal, ear webs to be applied to a traveling web, with zero or minimized waste present in the incoming ear web. Zero material is wasted due to the geometry of the chosen ear pattern and its downstream processing.

An ear is a component of a diaper that is grasped and pulled around the waist of a wearer. Typically, ears are secured to the diaper at a first end, and a second free end is typically equipped with securing means, such as a pressure sensitive adhesive, or hook and loop material. As a user grasps an ear and pulls the ear, elasticity provided about the waist region of the diaper allows the free end to be snugly pulled about the waist of a wearer, and coupled to the diaper. Ears can be rectangular or made of irregular shapes.

The present invention provides a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method (described later) with intermittent adhesive applied to the chassis web, or can be by vacuum transfer.

The present invention also allows for two side panel assemblies, including fastening mechanisms, to be attached to two ears, the side panel assemblies attached in a prefolded condition. Two more ears can coupled to a chassis web to create a front panel to wear about the waist of a user.

The present invention also allows for chips of material to be removed from the ears to provide a diaper with contoured leg openings. In one embodiment, the chips may be removed from the ears before the ears are attached to the chassis web. In an additional embodiment the chips may be removed from the ears after the ears are attached to the chassis web. In an additional embodiment the chips may be removed from the ears and a portion of the chassis web removed after the ears are attached to the chassis web.

BRIEF DESCRIPTION OF THE DRAWINGS

FIG. 8 is a perspective schematic view of the nested zero waste back ear applicator device and methods of the present invention;

FIG. 8a is a perspective schematic view of the nested zero waste back ear applicator device and methods of the present invention with an alternate web path configuration;

FIG. 9 is a side view of an ear turner assembly device used to rotate alternating ears;

FIG. 10a is front view of the ear turner assembly device used to rotate alternating ears;

FIG. 10b is front view of the ear turner assembly device used to rotate alternating ears, showing an alternate embodiment of a puck, configured to match in shape and size alternate ear design;

FIGS. 18-28 are schematic and plan views of methods of performing nested zero waste back ear application including a multi-component ear portion.

FIG. 18 is a plan view of an ear tab forming material (or wing, nonwoven web);

FIG. 19 is a plan view of an ear tab forming material following slitting and spreading;

FIG. 19a is a schematic view of formation of a side panel assembly;

FIG. 20 is a plan view of a side-panel assembly coupled to the ear tab forming material;

FIG. 21 is a plan view of the side-panel assembly coupled to the ear tab forming material, after the side-panel assembly has been folded;

FIGS. 22 and 23 are a plan view of the side-panel assembly coupled to the ear tab forming material, after the side-panel assembly has been folded, and during and after re-phasing of the side panel and wing assembly;

FIG. 24 is a plan view of the side panel and wing assembly being die cut, re-pitched, and rotated;

FIG. 25 is a plan view of the side panel and wing assembly following cutting, re-pitching and rotation;

FIG. 26 is a plan view of the side panel and wing assembly being coupled to a chassis assembly;

FIG. 27 is a plan view of the side panel and wing assembly, coupled to the chassis assembly, and folded into the profile of the chassis assembly;

FIG. 28 is an in-use plan view of an inventive disposable product formed by the methods of the present invention.

FIGS. 29-42 are schematic and plan views of methods of assembling a disposable product, including forming a nested zero waste ear to a nested zero waste wing portion, attaching ear and wing portions to a chassis top sheet, and folding the product to form a folded diaper.

FIG. 29 is a plan view of an ear tab forming material (or wing, nonwoven web);

FIG. 30 is a plan view of an ear tab forming material following slitting and spreading;

FIGS. 30-32 are a schematic view of formation of an ear assembly being slit, spread, tapes added, and the ear cut, repitched and rotated;

FIGS. 33-34 shown formation of a slit and spread wing web;

FIG. 35 shows the ear bonded to the wing web;

FIG. 36 shows the ear being folded down and temporarily coupled to the wing;

FIGS. 37-38 shown die cutting, repitching and rotating the wing assembly while carrying the ear assembly;

FIG. 39 is a plan view of the side panel and wing assembly being coupled to a chassis assembly;

FIG. 40 is a plan view of the side panel and wing assembly, coupled to the chassis assembly, and folded into the profile of the chassis assembly;

FIG. 41 is an in-use plan view of an inventive disposable product formed by the methods of the present invention;

FIG. 42 is a cross section view of an inventive disposable product formed by the methods of the present invention;

FIGS. 43-60 are schematic and plan views of methods of assembling a disposable product;

FIG. 96 shows the slit and spread components of FIG. 95, with chip removal;

FIG. 97 shows the slit and spread components of FIG. 96 after chip removal, the components spread apart;

FIG. 98 shows the components of FIG. 98 applied to a chassis web;

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
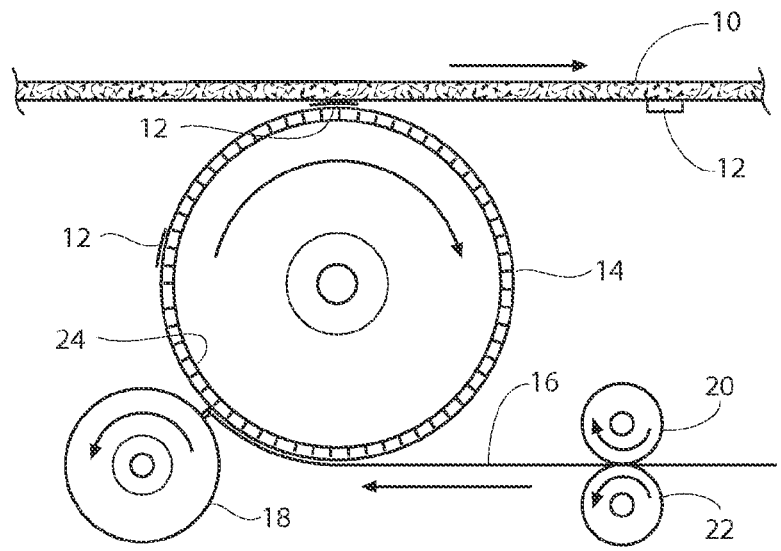
FIG. 1 is a diagrammatic side view of a Prior Art process.
Figure 2:
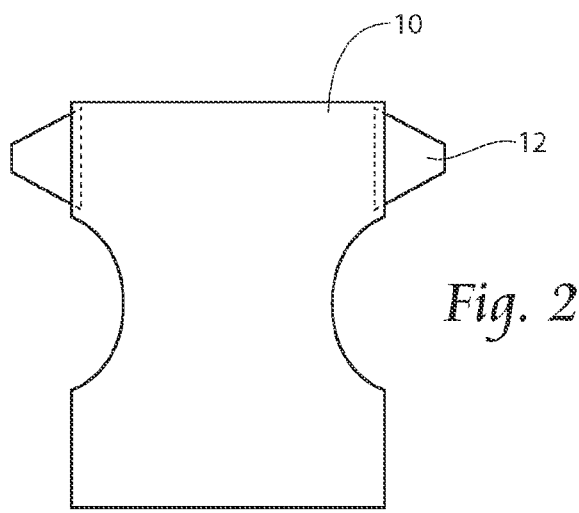
FIG. 2 is a top view of a disposable diaper product carrying a pair of ears.

Referring to the drawings there is seen in FIG. 1 a diagrammatic illustration of a prior art process for applying tabs to webs in a diaper making process, to result in an intermediate product shown in FIG. 2. The present invention can use this prior art method of affixing the segments 12 to the web 10, with a different anvil, the new anvil 114 described below. Web 10 is a composite material used in formation of diapers which is generally formed of various layers of material such as plastic back sheets, absorbent pads and nonwoven top sheets. A series of ears 12 are applied to web 10. In the illustrated process of FIG. 1, a rotatable vacuum anvil 14 is used to supply the ears 12 to web 10. Anvil 14 has internally reduced air pressure or vacuum (not shown), and a plurality of openings 24 are provided through its surface to enable suction of the tab segments 12 against the anvil surface 14. A web of the ear tab forming material 16 is fed by rollers 20 and 22 against the anvil surface 14 where it is cut into segments by a rotary knife 18.

The surface of the anvil roll 14 can have vacuum holes 24 on its smooth surface. In a typical configuration of a slip-and-cut applicator, there is a pattern of vacuum holes 24 distributed to evenly draw the entering web onto the surface of anvil 14 and thence into the cut point where the knife edge 18 engages the anvil 14.

It can be seen from FIG. 1 that in the prior art, the infeed of the ear tab forming material 16 can be at a first speed (with individual ears 12 spaced together), after which the individual ears gain speed to the speed of the anvil 14. Typical infeed speeds could be 120 mm/product for the infeed, while anvil speeds could be 450 mm/product on the anvil. This transition from the slower first speed to the quicker second speed takes place at the cut point, the ear tab forming material 16 slipping on the anvil 14 until cut. However, immediately at the transition cut point 18 from the slower speed to the faster speed, it is desired to place vacuum on the ears because centrifugal force would try to throw the ears off of the vacuum anvil 14.

Ear webs 16 can be comprised of two portions, 12a and 12b, as shown in FIG. 2. Segment 12a is more specifically referred to as the tab section of the ear 12, segment 12b is the ribbon section of the ear 12.

Figure 3:
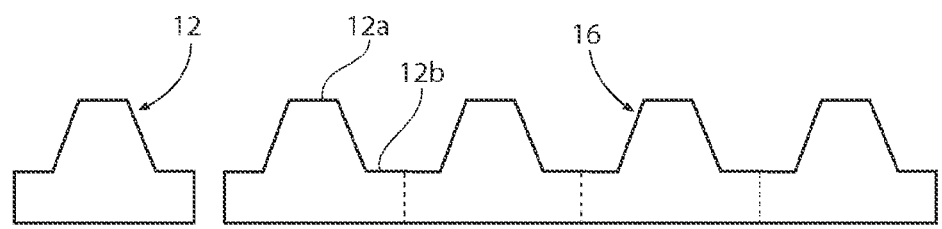
FIG. 3 is a top view of an ear forming web including an individual ear detached from the web.
Figure 6:
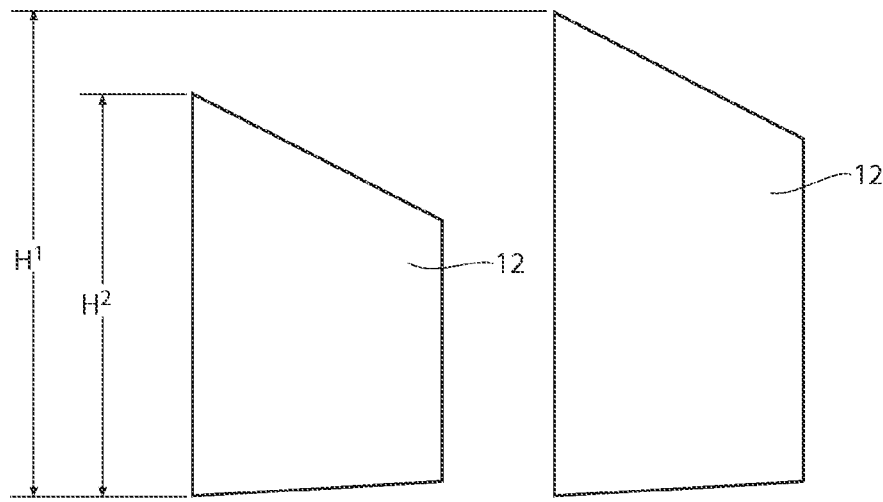
FIG. 6 shows an alternate ear pattern and alternate ear sizes.
Figures 7A, 7B:
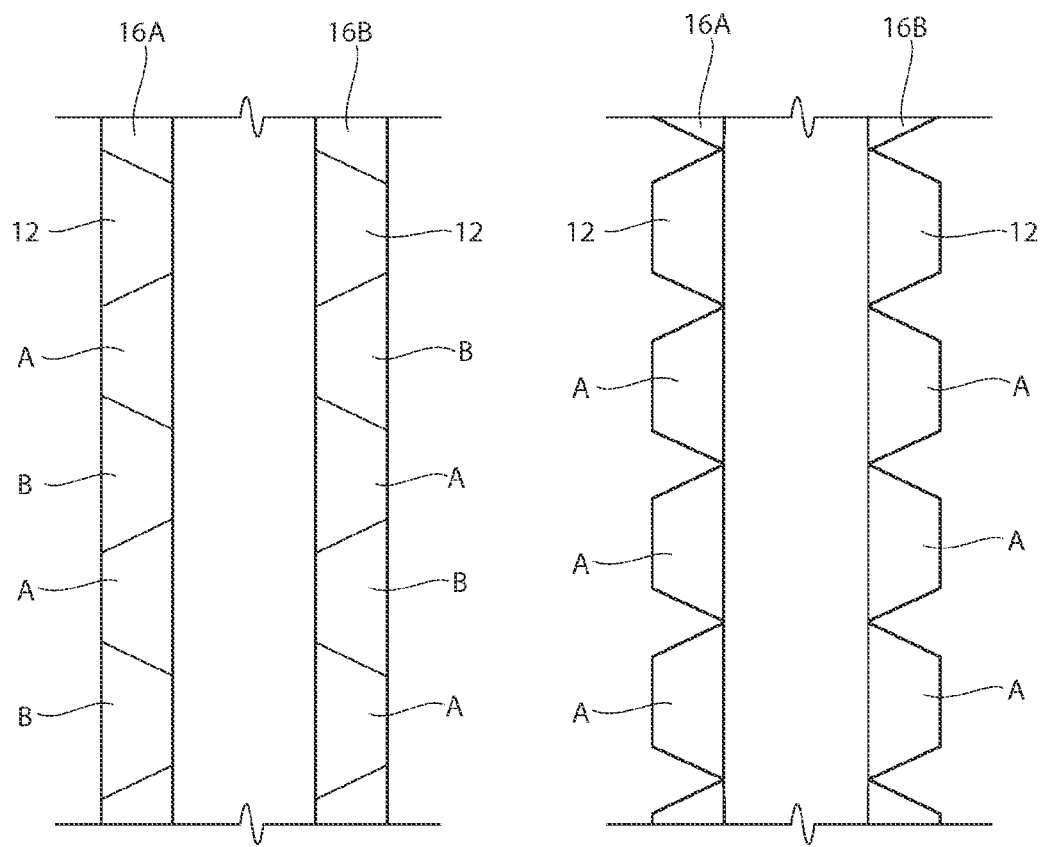
FIGS. 7A, 7B, 7C, 7D, 7E, and 7F are top views of ear webs, FIG. 7A showing non-rotated alternating die cut ear webs, and FIG. 7B showing alternating rotated die cut ear webs, and FIGS. 7C, 7D, 7E, and 7F showing alternate ear configurations.

Alternatively, the ears can comprise a trapezoidal shape, as shown in FIGS. 6, 7A and 7B, which will be described later. The trapezoidal shape of FIGS. 7A and 7B is particularly advantageous for zero waste applications, where it is desired to reduce or eliminate the scrapping of raw material. In another zero waste technique, two parallel series of alternating ear webs 16 with ribbon sections of the ear 12 could be created by mirroring the web 16 as shown in FIG. 3 and placing the mirrored web down one/half of an ear length (not shown).

Figure 4:
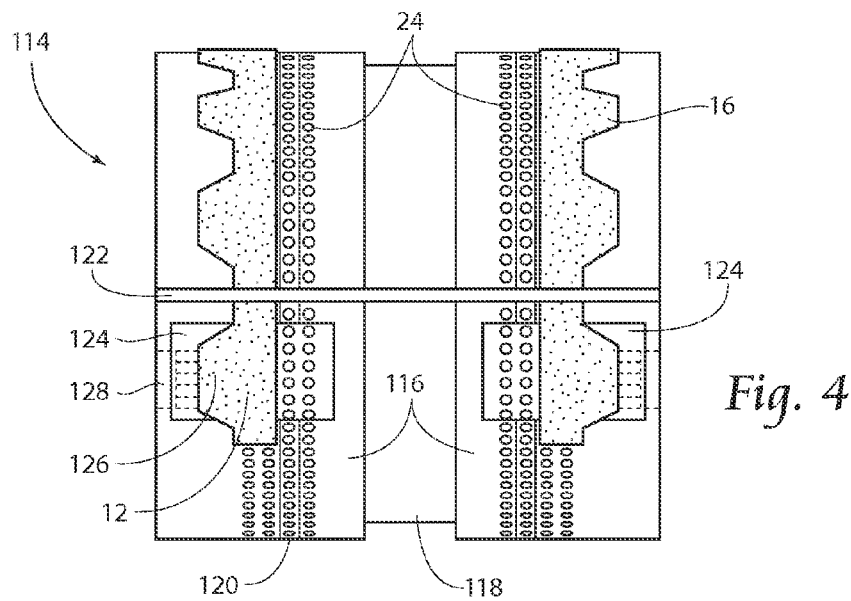
FIG. 4 is a front view of an anvil roll carrying two ear webs.

Referring now to FIG. 4, a front view of an anvil roll 114 is shown carrying ear forming material 16 (and later, individual ears 12) in phantom. The anvil roll 114 is preferably formed with two vacuum portions 116 separated by a center groove portion 118. The vacuum portions 116 are preferably mirror images of each other. The anvil roll 114 is symmetrical about a center plane through its circumference. Each vacuum portion 116 contains several circumferential rows of circular vacuum holes 24. Each vacuum portion 116 may also contain a circumferential groove 120 with an additional circumferential row of vacuum holes 24 located in the circumferential groove 120.

Still referring to FIG. 4, two diametrically opposed anvil pockets 122 and two diametrically opposed pairs of ear retaining portions 124 are shown. The ear retaining portions can be created as inserts, with different vacuum patterns applied as the user deems necessary. Each anvil pocket 122 is a groove which extends across the face of the entire anvil roll 114.

One ear retaining portion 124 is located on each of the vacuum portions 116. Each ear retaining portion 124 has an ear vacuum hole pattern 126 made of a plurality of vacuum holes 24 located at or near the surface of the anvil roll 144. A plurality of rows of vacuum holes 24 can be employed, each row having a plurality of vacuum holes 24, although more or less than those configurations or patterns shown can be used.

Figure 5:
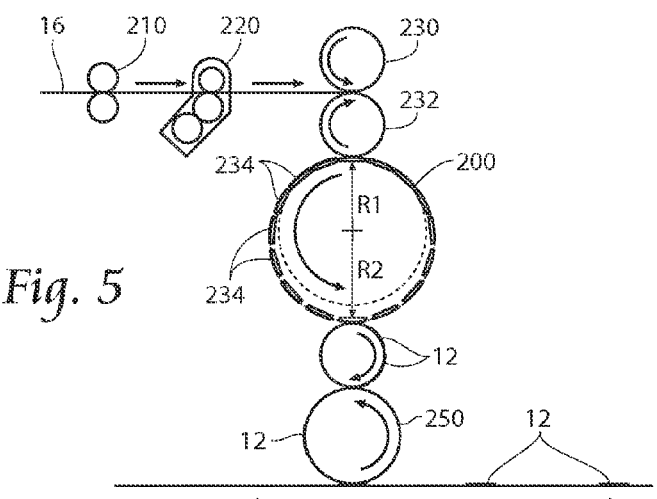
FIG. 5 is a schematic view of a nested zero waste back ear applicator device and methods of the present invention.

Referring now to FIG. 5, a schematic view of a nested zero waste ear applicator device and methods of the present invention are shown. Components of this ear applicator include a web slitter 210, which processes incoming ear web material 16 into two parallel paths (not shown from this view). After being slit, ear web material is processed by tape applicator 220, which can add tape to the ears for securing the ears 12 about the waist of a wearer.

After slitting and application of the tape to the ear web 16, an ear die is used to cut the ear web 16 into the pattern shown in FIG. 7A. The ear material 16 is die cut with a nested pattern on a synchronized vacuum anvil/die combination 230/232 and carried by rotation or otherwise to an ear turner assembly 200.

Referring still to FIG. 5, the cutting edges of the ear dies 230 turn against and in coordination with a corresponding anvil 232 to create preferably trapezoidal ears. It is noted that as shown in FIG. 6, ears 12 having different heights, H1 and H2, can be produced in this configuration by speeding up or slowing down the infeed rate of material 16 into the anvil/die combination 230/232. In this manner, more or less slip is allowed on material 16 prior to cutting, resulting in longer or shorter ears.

Figure 5A:
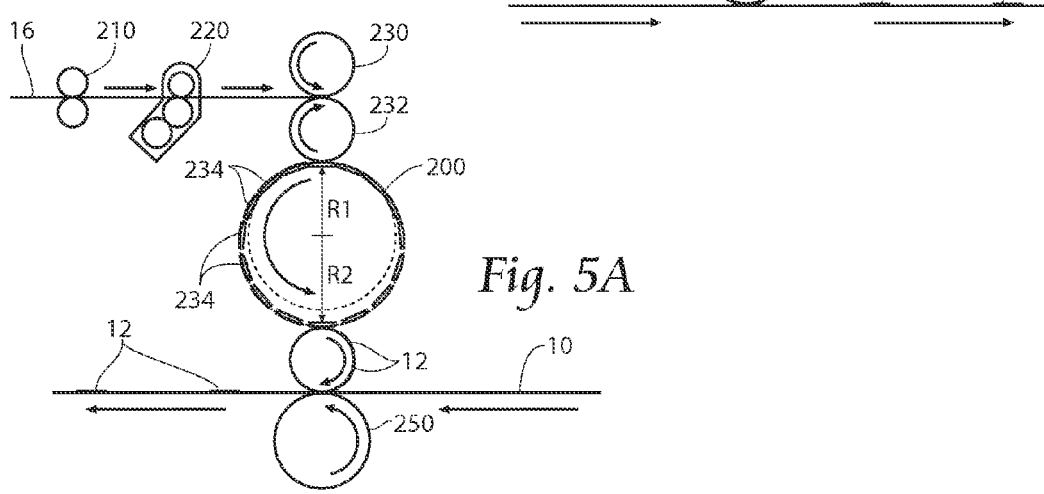
FIG. 5a is a schematic view of a nested zero waste back ear applicator device and methods of the present invention, with an alternate web path configuration.

Because the ear material 16 has already been slit into two lanes, one for a left side of a diaper and the other for a right side of a diaper, it is noted that two parallel ear dies 230 are used to produce the pattern shown in FIG. 7A to the slit web 16, but because of the side vantage point of FIG. 5a only one of the lanes is visible if more than one is desired.

The resulting discrete ear pieces however, due to the trapezoidal pattern of the ears shown in FIG. 7A, alternate between a correct orientation A and an incorrect (reversed) orientation B. The reversed ears B are required to be rotated 180° into the correct orientation A such that the ears and associated tape present a left ear and a right ear on the diaper, such as that shown on FIG. 7B. In correct orientation A, such as shown in FIG. 7B, the shorter of the parallel edges of the trapezoid will face toward an outside, left for the left side, and right for the right side. This geometry is desirable to accommodate the legs of the wearer when the ears 12 are pulled about the waist of the wearer.

To accomplish the reversal of the ear pattern, discrete ear pieces are picked up at the nested ear pitch by an ear turner assembly 200 (see FIGS. 5 and 8) that has a series of pucks 234 that travel radially from a minimal radius R1 (and therefore a minimal tangential speed) to a maximal radius R2 (and therefore a maximal tangential speed) at a depositional site. The difference between R1 and R2 is such that individual pucks 235 can be unnested and allow clearance (in the radial direction from adjacent pucks 234) for every other ear to be rotated, as will be described later in relation to FIGS. 10a and 10b. The rotated ears are then unnested and into the correct orientation and brought to the proper speed for deposition onto either an additional vacuum drum (as shown on FIG. 5a) and subsequently onto web 10 or high vacuum drum 250.

Referring to FIG. 7A, two lanes of ears 12 are depicted, 16A and 16B representing right and left ears intended for a product. The longest side of the ears 12 is intended for attachment to web 10, so because trapezoids are desirable, every other trapezoid in each lane will require 180° rotation to allow the desired side (for example, the longest side) of the ear 12 to be confronted with attachment to web 10. All of the "B" labeled ears 12 on supply 16A will be rotated 180° into an A position. All of the "B" labeled ears 12 on supply 16B will be rotated 180° into an A orientation position to achieve the desired depositional orientation shown in FIG. 7B.

Figure 7C:
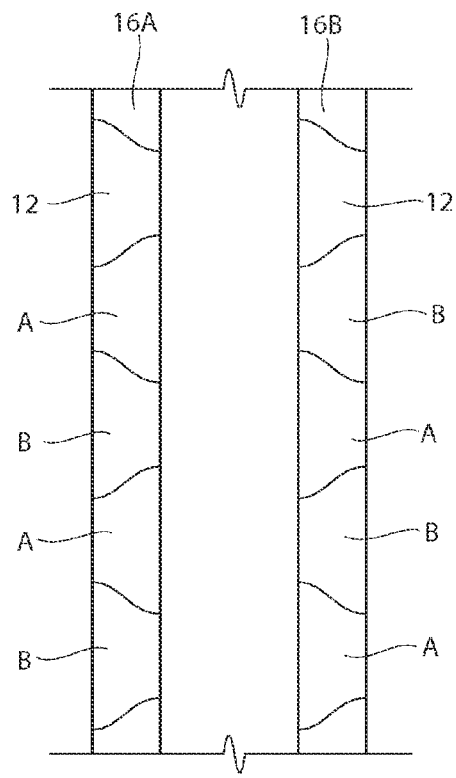
Figure 7D:
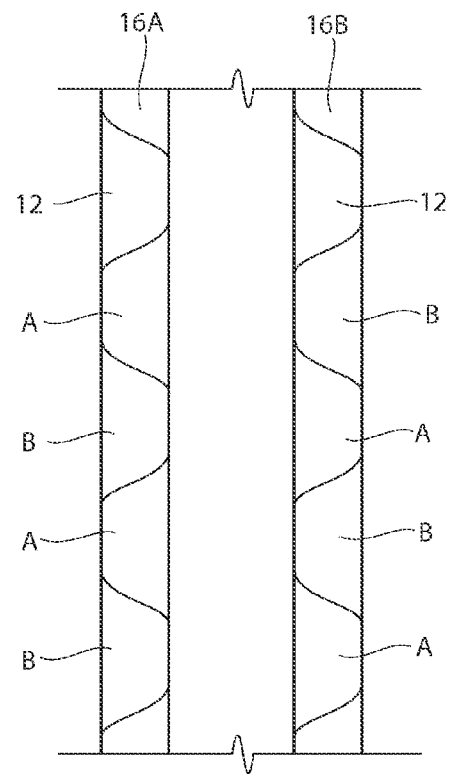
Figure 7E:
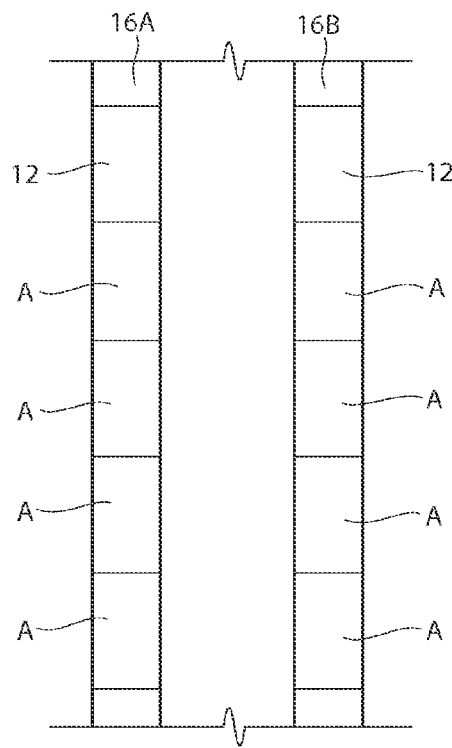
Figure 7F:
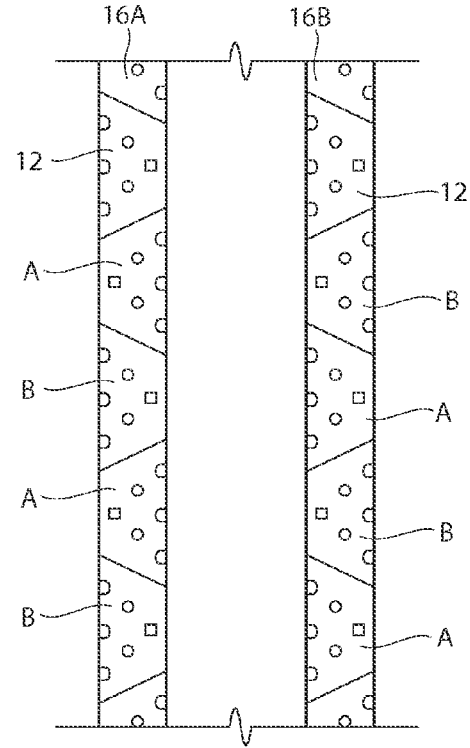

It is noted that ear configurations can vary as shown in FIGS. 7C-7F. In FIGS. 7C and 7D, wavy or curved ear patterns are shown. In FIG. 7E, a square pattern is shown. In FIG. 7F, a trapezoidal pattern is shown. Chips may be cut out in any shape of ear patterns, such as such in FIG. 7F. The chips can be of any shape or size, and can be positioned either on edges of the ears or on the interior of the ears.

Referring now back to FIG. 5, following rotation of every "B" labeled ear 12, each ear is deposited onto vacuum drum 240, rotated and picked up by high vacuum drum 250. Vacuum drum 240 is a size change roll that matches pitch. Vacuum drum 240 can also be used as a roller, in conjunction with or replacing roller 260, FIG. 16.

Because the ears 12 need to be sped up to match the speed of chassis web 10, the rotation of high vacuum drum 250 is quicker than that of vacuum drum 240.

The higher vacuum in drum 250 relative to drum 240 allows the ears 12 to be snatched or grabbed at the higher rotational speed present in drum 250.

Referring now to FIG. 5a, a schematic view of a nested zero waste back ear applicator device and methods of the present invention is shown, with an alternate web path configuration.

Referring now to FIG. 8, a perspective schematic view of the nested zero waste back ear applicator device and methods of the present invention is shown. As can be seen, two ear turner assemblies 200R (right) and 200L (left) are provided, to rotate every other ear 12 applied to the right side of the chassis web 10, and every other ear 12 applied to the left side of the chassis web 10. In this manner, for a single product, one of the two ears will have been rotated 180°.

As can be seen from FIG. 8, two types of pucks are provided, non-rotating pucks 234A and rotating pucks 234B. The non-rotating pucks 234A carry the "A" ears shown in FIG. 7A, or the ones that do not require rotation. The rotating pucks 234B carry the "B" ears shown in FIG. 7A. As the ear turner assemblies 200R and 200L go through their rotation, ears 12 are picked up from the ear die/anvil station 230/232 and rotate about the rotator 200, while every rotating puck 234B also rotates radially during rotation of the rotator 200, as will be described later.

The ears 12 are then deposited onto chassis web 10 and bonded thereto, for instance by ultrasonic bonding ring 252, where the resulting product is sent downstream for further processing.

Referring now to FIG. 8a, a perspective schematic view of the nested zero waste back ear applicator device and methods of the present invention with an alternate web path configuration is shown. This is the preferred embodiment of the vacuum drum/ultrasonic bonding ring 250/252 in relation to the vacuum drum 240. In this configuration, the ears are ultrasonically bonded to the chassis web 10 between the vacuum drum/ultrasonic bonding ring 250/252 and the vacuum drum 240 as the chassis web 10 travels from right to left as pictured.

Referring now to FIG. 9 a side view of the ear turner assembly device 200 is shown. The ear turner assembly device 200 used to rotate alternating ears, again with the entire device 200, rotating about a central axis, and each puck 234 traveling radially from a minimal radius R1 to a maximal radius R2 at a depositional site during rotation, and then back to the minimal radius R1. The difference between R1 and R2 is such that individual pucks 235 can be unnested and allow clearance for every other ear to be rotated. Comparing the During rotation from the R1 to the R2 position, rotating pucks 234B undergo not only the increase in radius, but also undergo 180° rotation about an axis perpendicular to the central axis. This can be performed preferably with a screw operation (reference letter S, FIG. 12). During rotation from the R2 position back to the R1 position, the rotating pucks 234B rotate back through their 180° rotation to get to their initial position by use of a yankee screw, which is capable of both advancing and retracting the pucks 234B, and rotating the pucks 234B, upon driving the shaft of the yankee screw inward and outward radially.

Referring now to FIG. 10a, a front view of the ear turner assembly device 200 used to rotate alternating ears is shown. As can be seen, the pucks 234 are each equipped with vacuum voids 236 through which a vacuum is pulled, retaining ears on the rotator device 200 through their rotation (radially rotating for every ear, radially and axially rotating for every other ear) until deposition. As can be seen, the pucks 234 are can be roughly trapezoidal in shape to roughly match the shape of the ears 12. It is also seen from this view that the non-rotating pucks 234A remain in their axial non-rotated position relative to the rotating pucks 234B, which rotate from their initial position nested between two non-rotating pucks 234A, and back.

Referring now to FIG. 10B, an alternate shape of the pucks 234 is shown. In FIG. 10A, the pucks 234 are configured to receive wavy shaped ears as described earlier. In FIG. 10B, the pucks 234 are configured to receive trapezoidal shaped ears as described earlier. It is preferable to configure the pucks 234 to match the desired ear pattern.

Figure 11:
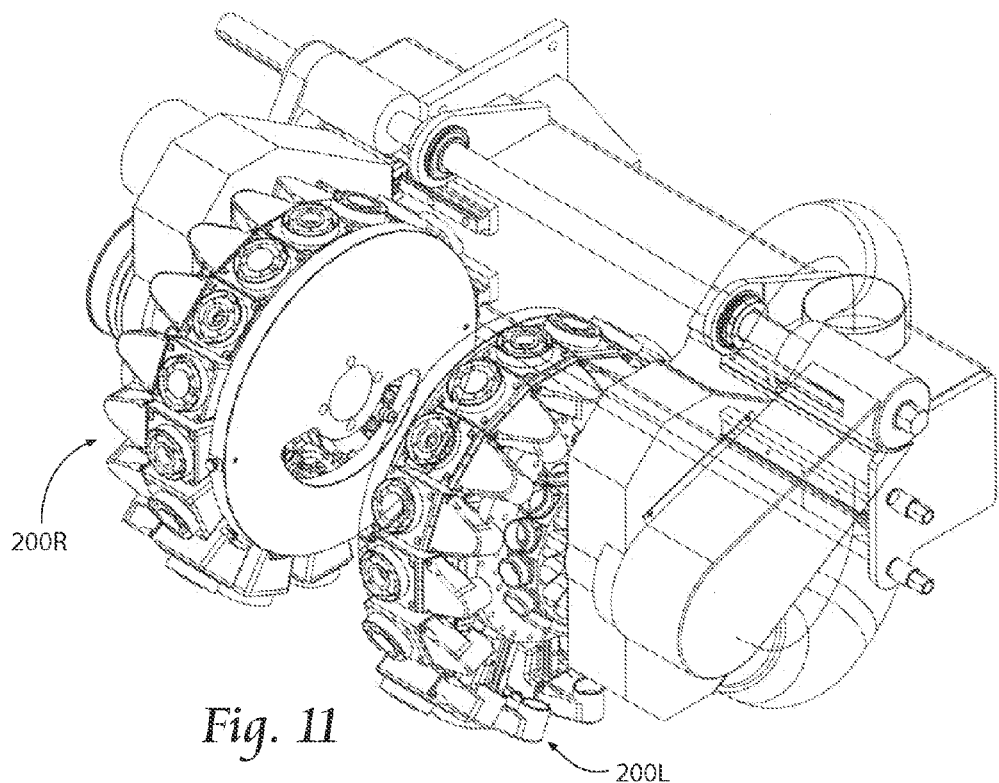
FIG. 11 is a perspective view of two ear turner assembly devices used to rotate alternating ears on a left and a right ear web.

Referring now to FIG. 11, a perspective view of the two ear turner assembly devices 200R and 200L are shown. Also shown are vacuum manifolds used to apply the vacuum to the pucks 234. In this sense, the rotation of the pucks 234 is described in currently pending U.S. application Ser. No.

Figure 13:
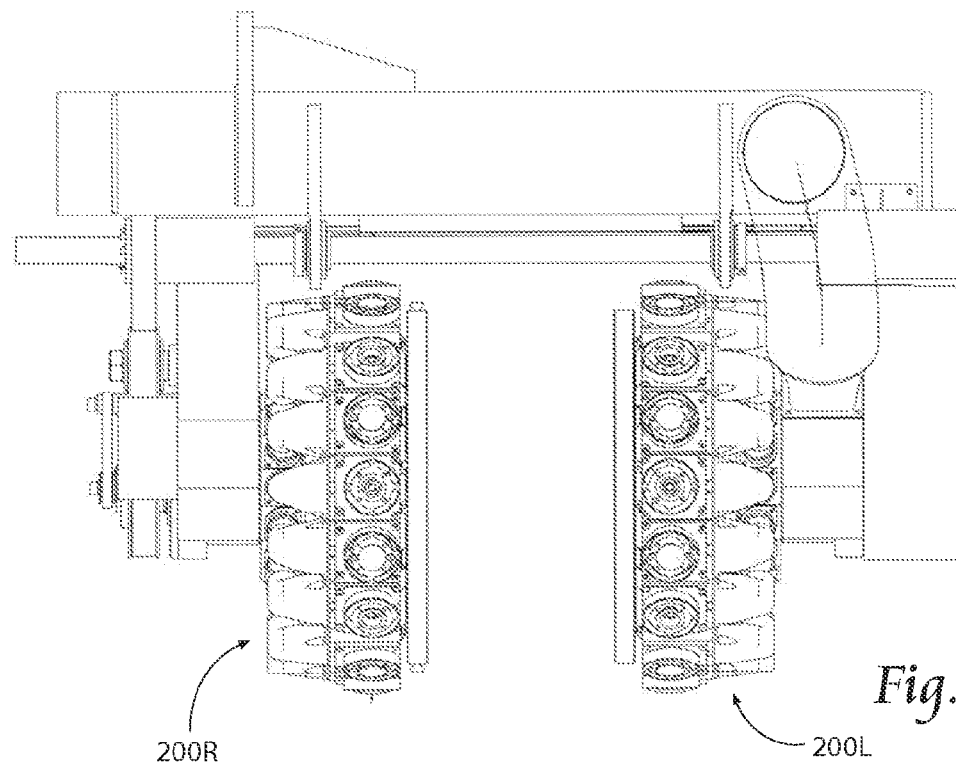
FIG. 13 is a front view two ear turner assembly devices used to rotate alternating ears on a left and a right ear web.
Figure 14:
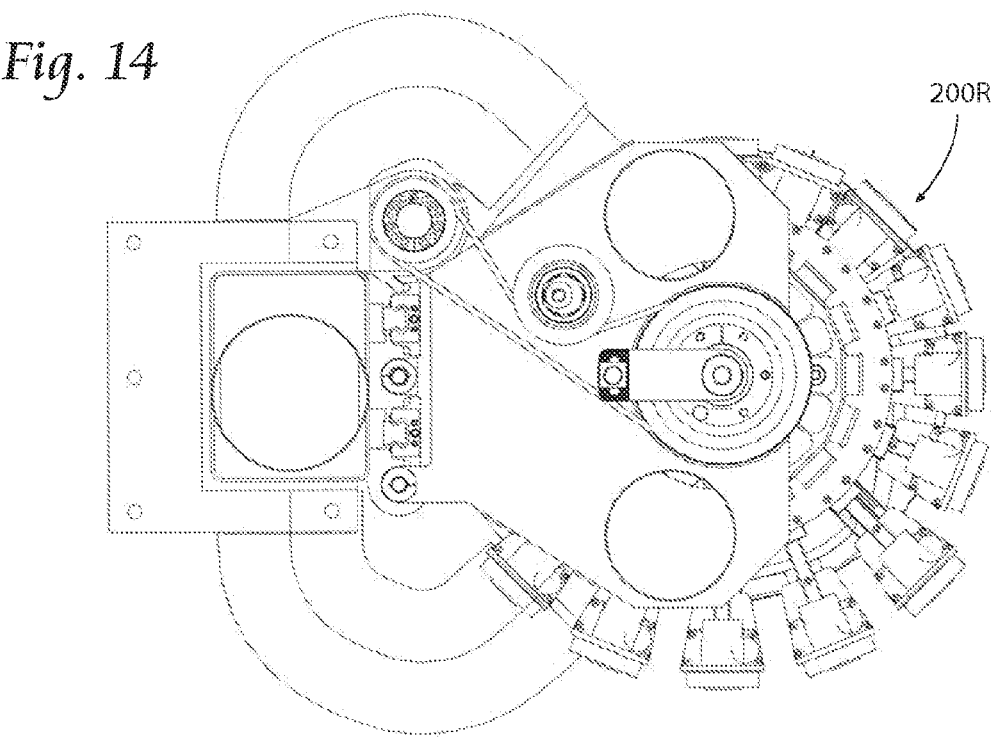
FIG. 14 is a side view of an ear turner assembly device used to rotate alternating ears.

11/244,387, which is incorporated herein by reference. A front view of this configuration is shown in FIG. 13 and a side view in FIG. 14.

Figure 12:
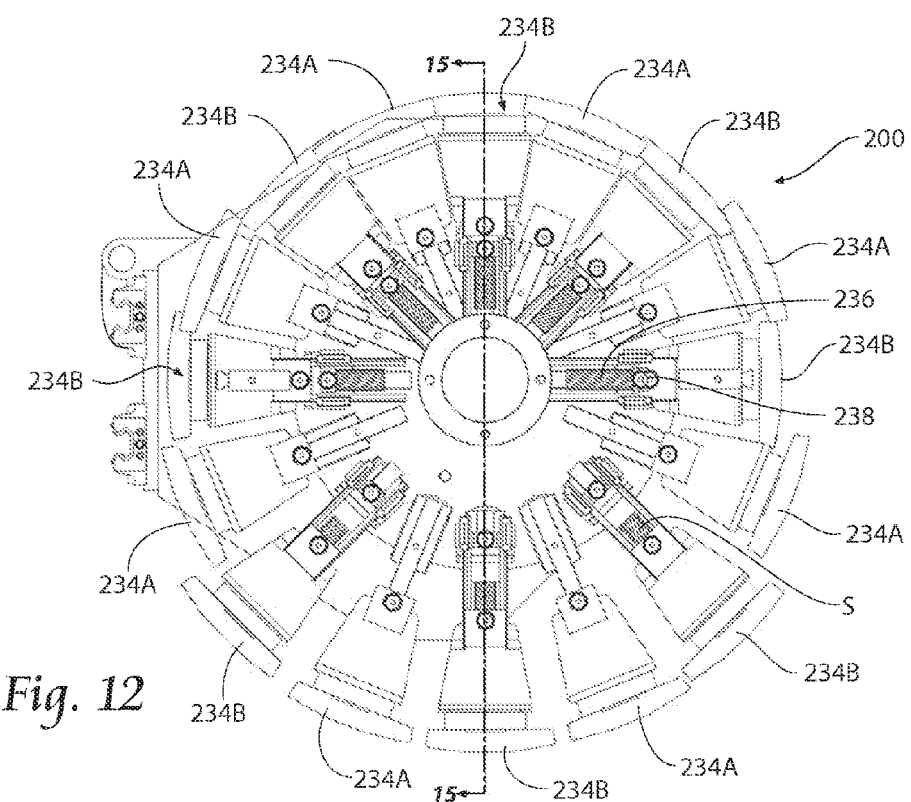
FIG. 12 is a side view of an ear turner assembly device used to rotate alternating ears.

Referring now to FIG. 12 a mechanism for rotating pucks 234b is shown. There, it is seen that screws 236 are provided such that movement of the pucks 234B away from the center axis simultaneously causes rotation of puck 234B. A radially traveling coupling 238 couples the puck with the screw 236, and when the threads of the screw are engaged with the radially traveling coupling 238, rotation is caused.

Figure 15:
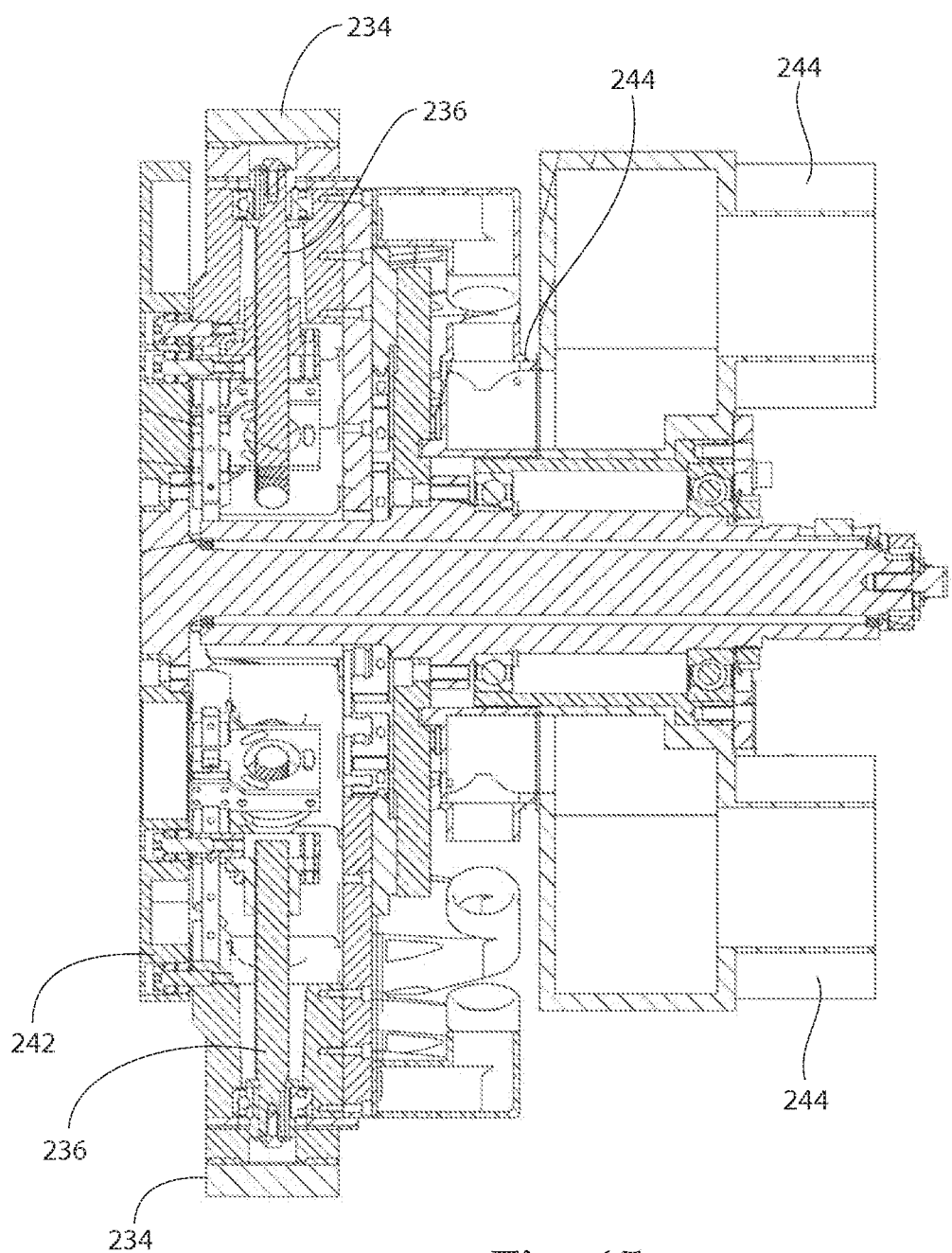
FIG. 15 is a sectional view of the ear turner assembly device used to rotate alternating ears shown in FIG. 10.

FIG. 15 is a cross-sectional view of the ear turner assembly device 200 used to rotate alternating ears along the line shown in FIG. 12. Particularly, screws 236 are operably coupled with pucks or rotator assemblies 234. By rotation of the screw 236, pucks 234 are moved along a radial line in relation to shaft turner 246. Vacuum manifold 244 is provided to commute vacuum to the pucks 234 and ultimately to hold the ears 12 in place. Ear turner cam 242 is provided for rotative purposes.

Figure 16:
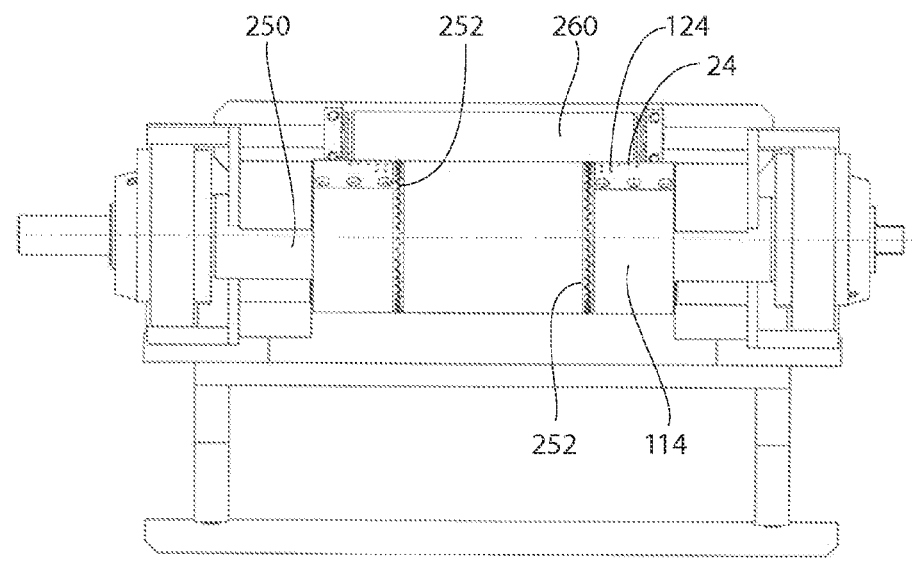
FIG. 16 is a front view of an anvil, ultrasonic bonding ring, and vacuum pattern used for pitch changing ears from a slower web and applying and bonding the ears to a faster moving chassis web.

Referring now to FIG. 16, a front view of a rotatable vacuum wheel 114, ultrasonic bonding ring 252, and vacuum pattern 124 used for pitch changing ears from a slower web and applying and bonding the ears 12 sandwiched between roller 260 and the anvil 114 to a faster moving chassis web is shown.

In this embodiment, the aggressive vacuum pattern 124 on high vacuum drum 250 will have withdrawn ears 12 from vacuum drum 240. This step follows the rotation of the "B" ears as described above. The chassis web 10 is fed in between the roller 260 and the high vacuum drum 250. The ultrasonic bonding ring 252 couples the ears 12 with the chassis web 10 (refer to FIG. 5).

Figure 17:
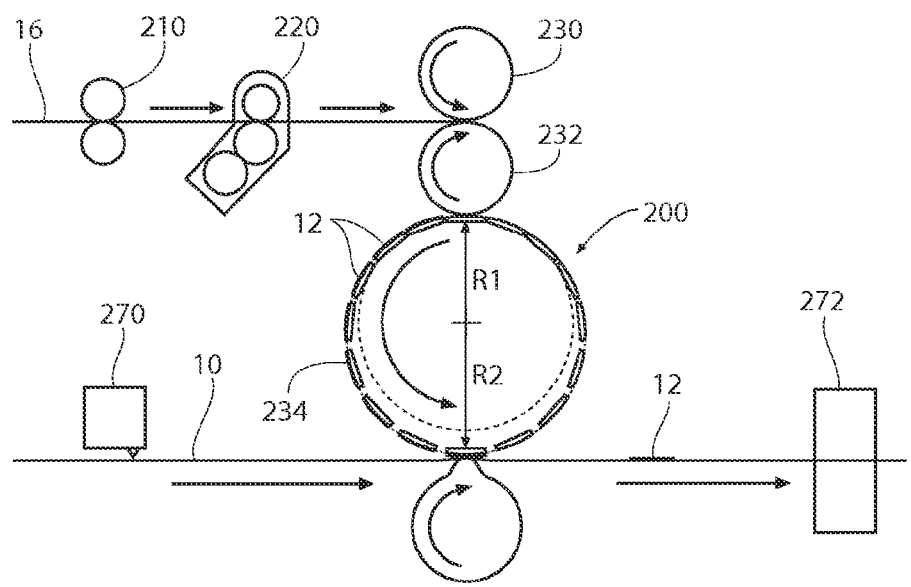
FIG. 17 is a schematic view of the nested zero waste back ear applicator device and methods of the present invention, shown with an alternate embodiment of a means for applying the ear to the chassis web.

Referring now to FIG. 17, a schematic view of the nested zero waste back ear applicator device 200 an alternate embodiment of a means for applying the ear 12 to the chassis web 10 is shown. Instead of the vacuum porting system as previously described, a protuberance carrying rotatable body 274 is urged against the chassis web 10, as disclosed in U.S. Pat. No. 6,475,325, which is incorporated herein as if fully set forth. The disclosure of U.S. Pat. No. 6,475,325 is referred to as the "bump transfer" method. In this embodiment intermittent adhesive is applied to the chassis web 10 at station 270. The intermittent adhesive is applied at intervals to make contact with ears 12 carried by rotating body 200. The protuberance carried by body 274 urges the chassis web 10 towards an ear 12 carried by a puck 234. With the ear 12 coupled with the chassis web, the coupled material is processed by final bonding station 272, after which the ear/chassis combination is sent downstream for further processing as desired.

Referring generally to FIGS. 18-28, schematic and plan views are presented of a novel disposable garment configuration using methods of performing nested zero waste back ear application including a multi-component ear portion fabrication, bonding and folding. The embodiments of FIGS. 18-28 are particularly well suited for formation of what is called in the industry as an adult-sized diaper.

One difficulty with adult-sized products is sheer size. The products are required to be quite large (for instance, 32" wide in a non-stretched condition) in the waist section to fit about the waist of an adult. However, the adult-sized products are typically shipped in packages about 8" wide, so the products require folding, particularly at the waist zone where the product is the widest, in order to be compactly packaged and shipped.

The prior art often employed a Z-fold of ears to get the waist band down to size. For instance, the ears 12 applied to web 10 shown in FIG. 2 would have to be folded as to not extend much past the profile of the chassis web 10. This assists both processing of the web as it avoids flying parts, but also assists packaging and transport of the material.

The embodiments of FIGS. 18-28 show construction of an ear segment that can be formed of multiple pieces, as opposed to the one piece ears of the prior art (see, e.g., ears 12 of FIG. 2). This allows both creation of a contoured multi-piece ear segment, as well as assembly of at least portions of the ear segment in a pre-folded condition.

Figure 18:
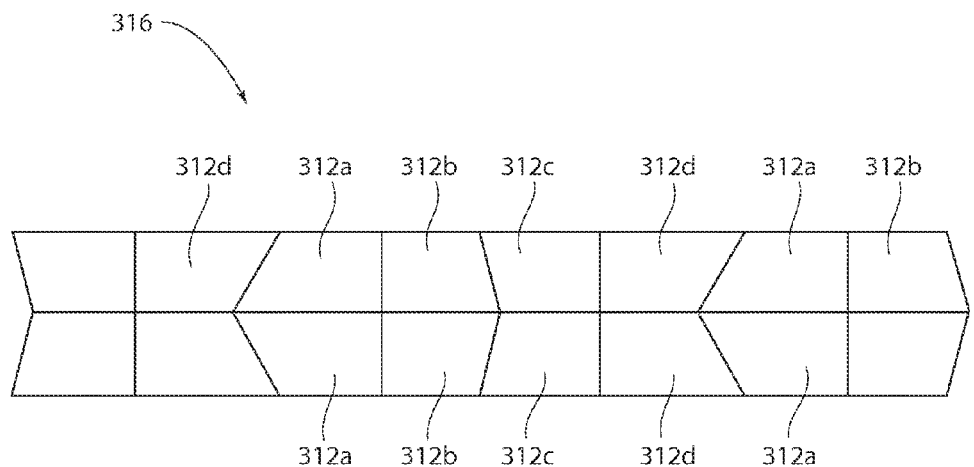

Referring now to FIG. 18, a plan view of an ear tab forming material 316 is shown entering the system similarly positioned to material 16 shown on FIG. 8 or 8a. Preferably the ear tab forming material (or wing) 116 is a non-woven continuous web of material which is ultimately formed into shaped ear portions 312. Shaped ear portions 312, as described with respect to FIGS. 7a-7f, can take on different shapes, and can have correct original orientation, or orientation that requires re-phasing or turning as described above.

In a preferred embodiment ear portions 312 of the present invention will have side panel assembly receiving ear portion configurations 312a and 312d, and non-receiving ear portion configurations 312b and 312c as will be described later.

Figure 19:
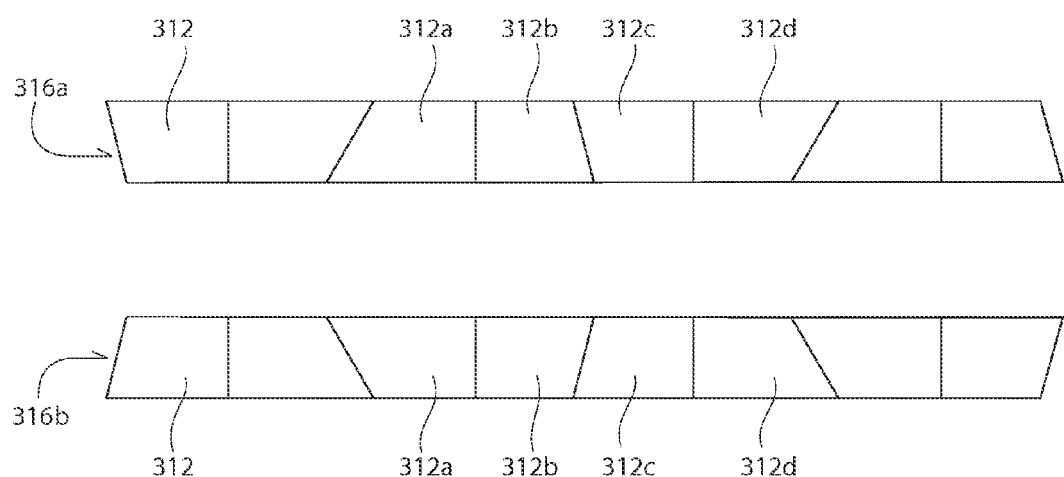

Referring to FIG. 19, the ear tab forming material 316 is slit and spread, for instance as shown on FIG. 8 at station 210. Lanes 316a and 316b of slit and spread ear tab forming material 316 receive the side panel assemblies described in FIG. 19a, and ultimately become left and right ear segments on a disposable product.

Referring now to FIG. 19a, a schematic view of formation of side panel assemblies 320 is shown. The formation of side panel assemblies 320 begins with an outer non-woven web material 318, which is slit and spread into discrete non-woven web portions 318a, 318b, 318c, and 318d, each of the non-woven web portions also preferably being cut in the cross-machine direction into the preferred size.

To each of the discrete non-woven web portions 318a, 318b, 318c, and 318d, one or more fastening mechanisms 322 are applied. Fastening mechanisms 322 can be tape tabs, covered tape tabs, strips of hook and loop material, continuous hook and loop material, patches of hook and loop material, etc. The fastening mechanisms 322 will be unfastened and refastened about the waist of the user to tighten the disposable garment about the waist.

Next, the non-woven webs 318 carrying fastening mechanisms 322 are folded over, creating a folded web 318 and folded fastening mechanisms 322'.

This causes the combination of the non-woven web 318 and the fastening mechanisms 322 to be narrower than the discrete non-woven web portions 318a, 318b, 318c, and 318d. It is noted that the folded fastening mechanisms 322' of web portions 318a and 318b will have opposing fastening mechanisms 322' as they will become the right and left hip waist fastening mechanisms, respectively, once placed about the waist of a user (shown later in the process).

In addition to the discrete non-woven web portions 318a, 318b, 318c, and 318d, a stretch laminate web 324 is also provided. This too is slit and spread into discrete stretch laminate web portions 324a, 324b, 324c, and 324d.

Next, the non-woven web portions 318a, 318b, 318c, and 318d, including their respective fastening mechanisms 322', are bonded to stretch laminate web portions 324a, 324b, 324c, and 324d respectively, forming the side panel assemblies 320 in four different lanes, 318a+324a, 318b+324b, 318c+324c, and 318d+324d. The non-woven web portions 318a, 318b, 318c, and 318d can be bonded to the stretch laminate web portions 324a, 324b, 324c, and 324d in any fashion, such as by ultrasonic bonding using a mechanism such as shown in FIG. 16, by lap seams, by adhesives, fin seams, etc.

The stretch laminate portions 324a, 324b, 324c, and 324d can also be folded if desired, or the stretch laminate portions 324a, 324b, 324c, and 324d in combination with the nonwoven web portions 318a, 318b, 318c, and 318d can all be folded together and again.

Figure 20:
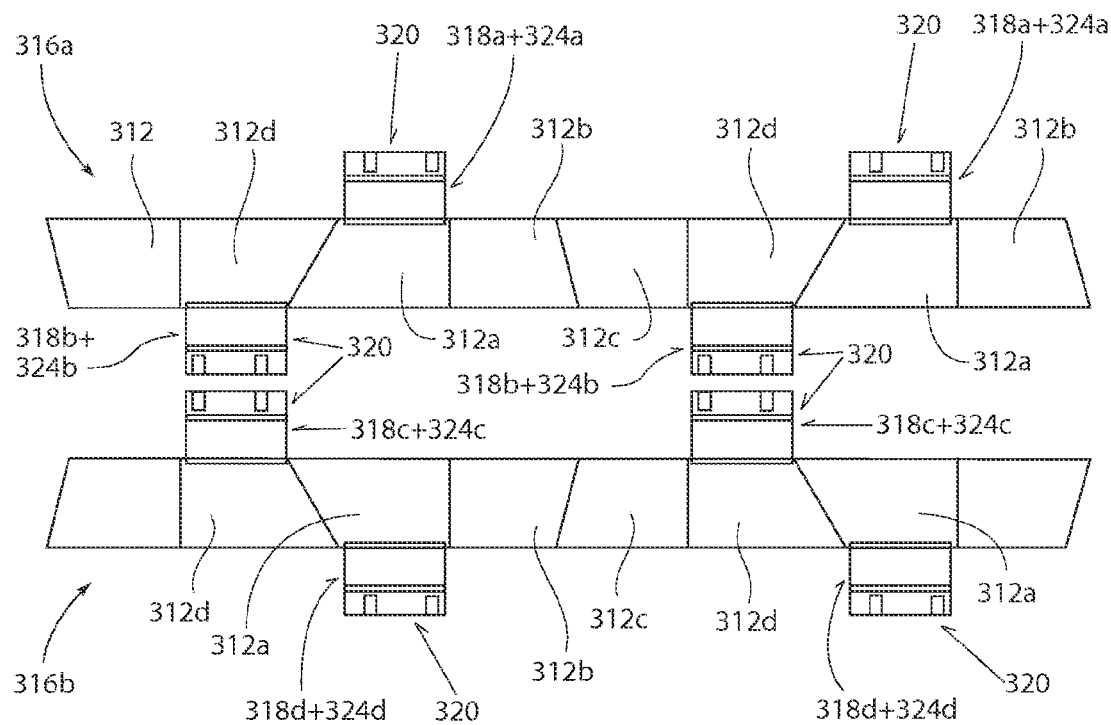

Referring now to FIG. 20, a plan view of a side-panel assembly 320 coupled to the ear tab forming material is shown. In a preferred embodiment, side-panel assembly 320, and particularly the panel 320 having configuration 318a+324a (from FIG. 19), is slip-cut onto the top of lane 316a, and particularly slip-cut and coupled to ear portion configuration 312a.

Similarly, side-panel assembly 320, and particularly the panel 320 having configuration 318b+324b (from FIG. 19), is slip-cut onto the bottom of lane 316a, and particularly slip-cut and coupled to ear portion configuration 312d.

In lane 316b, side-panel assembly 320, and particularly the panel 320 having configuration 318c+324c (from FIG. 19), is slip-cut onto the top of lane 316b, and particularly slip-cut and coupled to ear portion configuration 312d.

Similarly, side-panel assembly 320, and particularly the panel 320 having configuration 318d+324d (from FIG. 19), is slip-cut onto the bottom of lane 316b, and particularly slip-cut and coupled to ear portion configuration 312a.

The panels 320 can be coupled to the slit and spread ear tab forming material 316 in any fashion. Preferred methods may include ultrasonic bonding, adhesive bonding, heat, etc. Also, the coupling between the panels 320 and the ear tab forming material 316 could be contained in, or be a portion of a larger laminate involving other materials and bonds.

Figure 21:
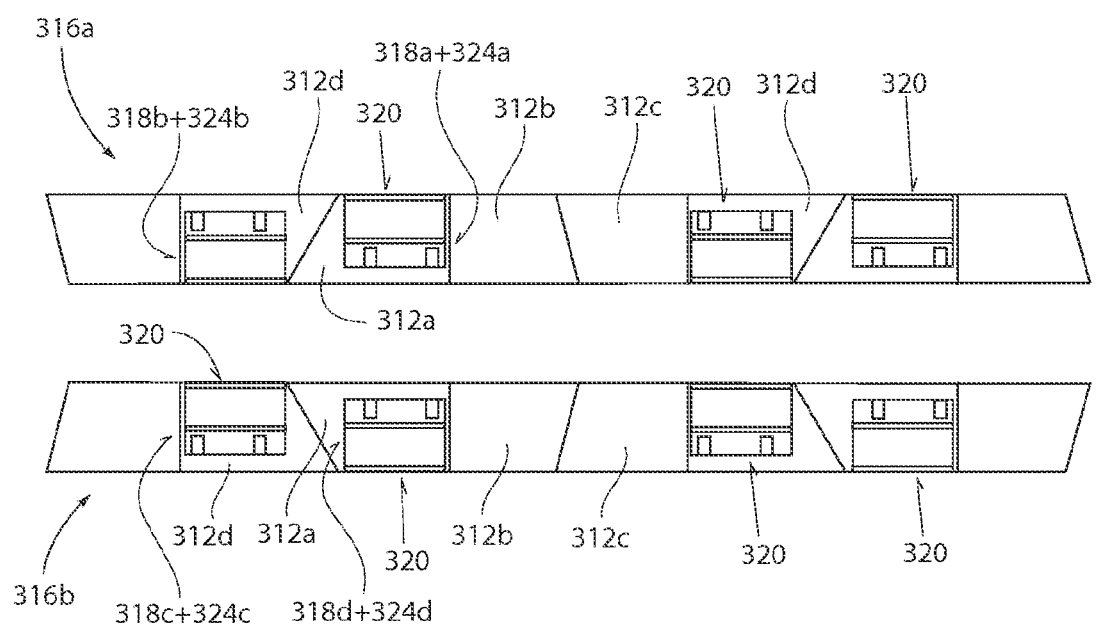
Figure 22:
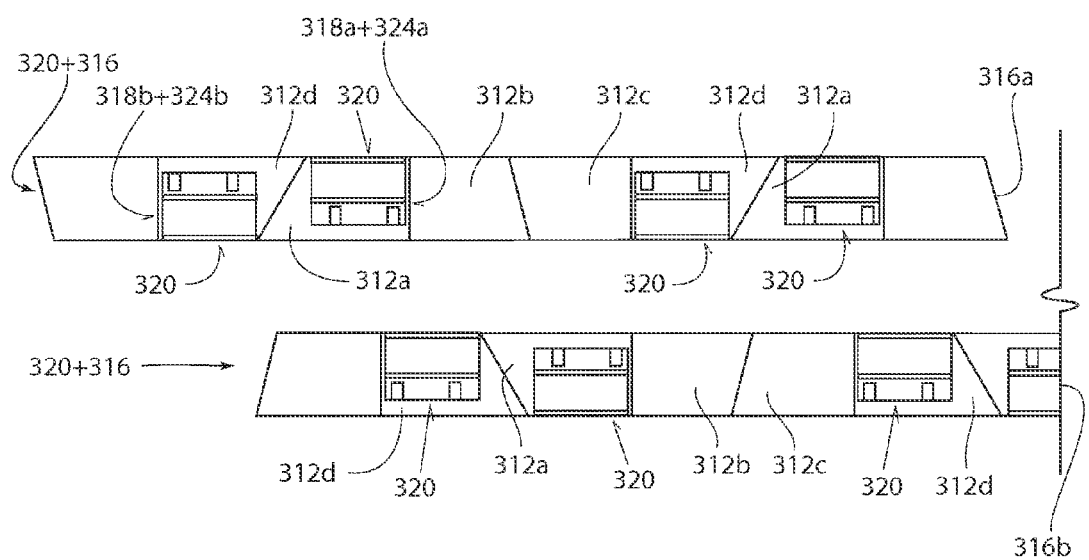
Figure 23:
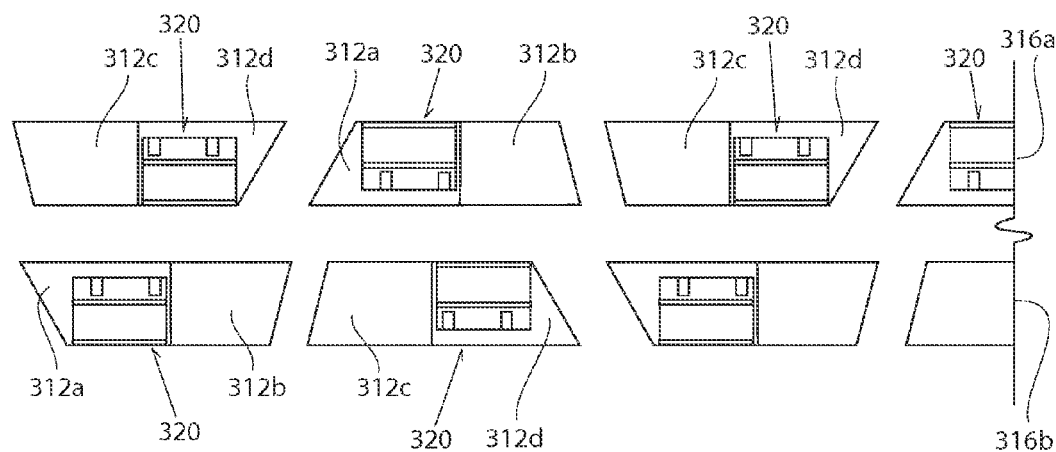

Next, referring now to FIG. 21, the side-panel assemblies 320 have been folded over (or under) the ear tab forming material 316, to conform to, and preferably be narrower than, the ear portions 312 of lanes 316a and 316.

It is desirable to process the combination of the side-panel assemblies 320 temporarily staked to the ear tab forming material 316 together, so that components do not become entangled in the machinery during processing. It is also desirable so that packaging can be accomplished orderly and uniformly. Preferably, the side-panel assemblies 320 are temporarily staked to the ear tab forming material 316. The temporary staking can be done, for instance but not by way of limitation, by a light application of adhesive, by a light compression bond, by a light compression bond assisted by slight penetration of pins through the layers, by a weak ultrasonic bond, or by other types of temporary and light bonds may be employed.

Referring now to FIGS. 22-25, after the side-panel assembly 320 has been coupled to the ear tab forming material 316, and after the side-panel assembly 320 has been folded, the side panel and wing assembly 320+316 is treated as the ear 12 was treated with reference to FIGS. 1-17. For instance, the side panel assembly 320 and ear tab 316 can be re-phased (FIGS. 22-23), then die-cut, repitched, and rotated (FIGS. 24-25).

In particular, the ear portion configurations 312c and 312d can be slip-cut together with a unit such as shown on FIG. 8 or 8a onto the machine shown on FIG. 9, which would die-cut, re-pitch and rotate every other wing assembly as shown on FIG. 24.

The 316a lane would be treated by one of the ear turner assemblies 200R (right) or 200L (left) of FIG. 11, and the 316b lane would be treated by the other of the 200R or 200L ear turner assemblies.

As a result, and as shown on FIG. 25, every other of the ear portion configurations 312c and 312d will have been rotated 180° and re-phased, such that the 312a/312b ear portion configurations will appear identical to the rotated 312c/312d ear portion configurations and the 316a and 316b lanes would be mirror images of one another.

Figure 26:
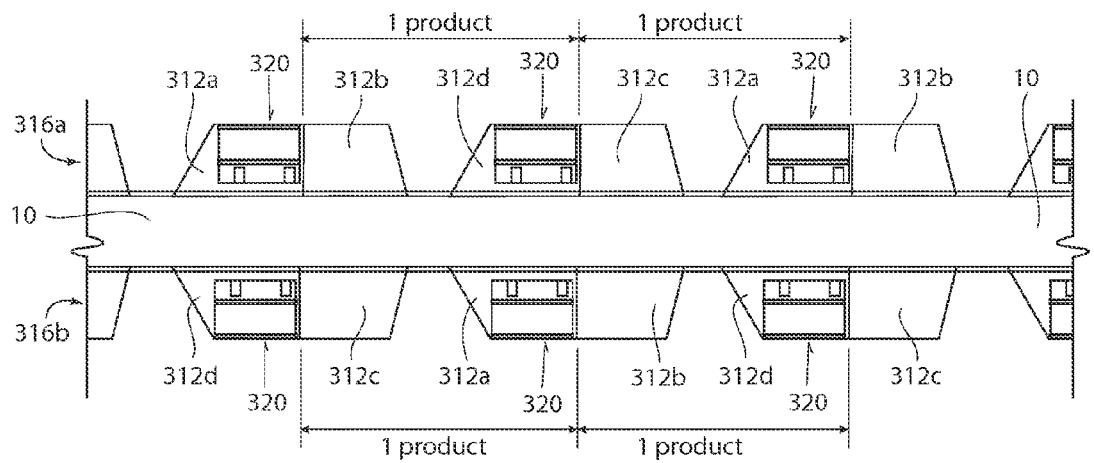

Referring now to FIG. 26, the ears 312 and side panels 320 have been properly oriented and re-phased such that right front ear 312b (front of product, no side panel 320 attached) and its associated right back ear 312d (back of product, with a side panel 320 attached and folded) are mirrored with left front ear 312c (front of product, no side panel 320 attached) and its associated left back ear 312d (back of product, with a side panel 320 attached and folded). These ears 312 and side panels 320 are introduced to, and coupled with web 10 (or chassis top sheet), typically a composite material used in formation of diapers which is generally formed of various layers of material such as plastic back sheets, absorbent pads 340 and nonwoven top sheets (visible in FIGS. 27 and 28).

Figure 27:
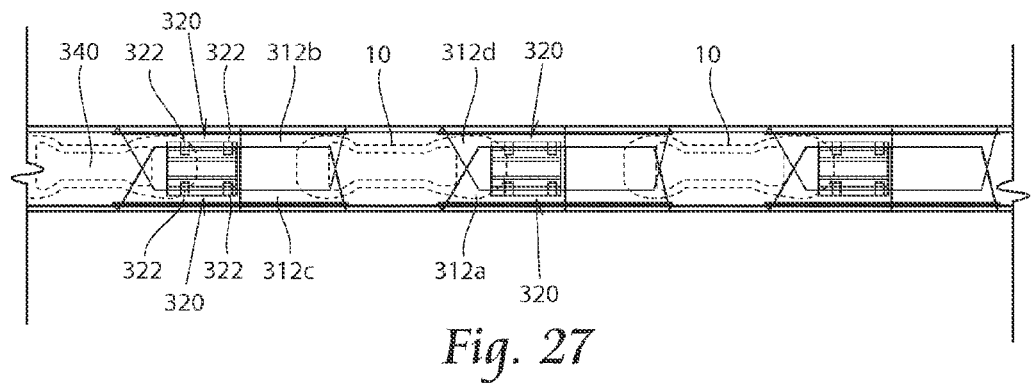

Referring now to FIG. 27, the next step is to fold the ears 312b and 312c, and 312a and 312d their associated side panels 320 down, in overlapping fashion, such that either one of lanes 316a and 316b is folded down first, followed by the other. As can be seen, the ears 312b and 312c, and 312a and 312d their associated side panels 320 are folded into, and narrower than, the width of the chassis assembly 10 in the cross-machine direction.

Figure 28:
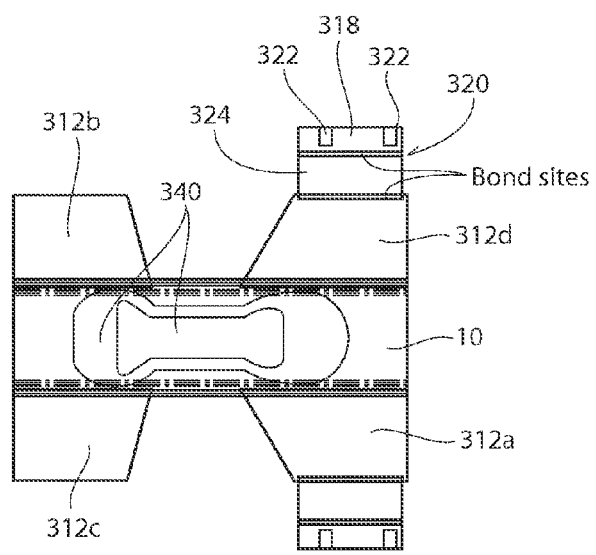

FIG. 28 is an in-use plan view of a inventive disposable product formed by the methods of the present invention. As can be seen, the ears 312a and 312d are coupled to their associated side panels 320, which had been previously folded onto the ears 312. A user can place the absorbent pad 340 in the crotch region, and couple the fastening mechanisms 322 of the side panels 320 about the waist, to reach the front of ears 312b and 312c and fasten the disposable product.

Referring now to FIGS. 29-42, schematic and plan views of methods of assembling a disposable product, including forming a nested zero waste ear to a nested zero waste wing portion, attaching ear and wing portions to a chassis top sheet, and folding the product to form a folded diaper are shown. In general, the product shown in FIGS. 29-42 is formed by cutting (preferably die cutting) a web (preferably a stretch laminate or non-woven) to form an ear, alternately turning and attaching the ear to a wing, fold and stack the ear to the wing, die cutting the wing, alternately turning and attaching wing and ear assembly to a chassis, folding and stacking a wing to a chassis non-woven.

Referring to FIG. 29, the process begins with a web portion 1000 (preferably non-woven), introduced into the system, which, as shown in FIG. 30, is split and spread into four lanes of non-woven webs 1002, 1004, 1006, and 1008, similar to that described above with reference to FIG. 19a. Instead of the rectangular cuts created of the discrete non-woven web portions 318a, 318b, 318c, and 318d of FIG. 19a, the ears 1012 shown in formation of the ear of FIGS. 29-32 can be cut of a zero waste trapezoidal configuration as shown, or other zero waste rectangular or non-rectangular configurations (such as in FIGS. 7a-7f).

As shown in FIG. 31, tapes 1022 are applied to the non-woven (similar to 322 and 322' of FIG. 19a) and folded. Next, referring to FIG. 32 the ears 1012 are die cut, repitched and rotated, in the fashion shown, for instance utilizing a machine depicted in FIGS. 11-14. The final orientations shown tapes 1022 folded in-line of the ears 1012, and the ear orientations after folding resulting in four different ear orientations, 1012*a*, 1012*b*, 1012*c*, and 1012*d*.

In orientation 1012*a*, the tapes 1022 are on the top side, with the long side (opposite the top side) on the bottom side. In orientation 1012*b*, the tapes 1022 are on the bottom side, with the long side (opposite the bottom side) on the top side. Similar rotation and resulting orientations are shown with respect to 1012*c* and 1012*d*.

Figure 35:
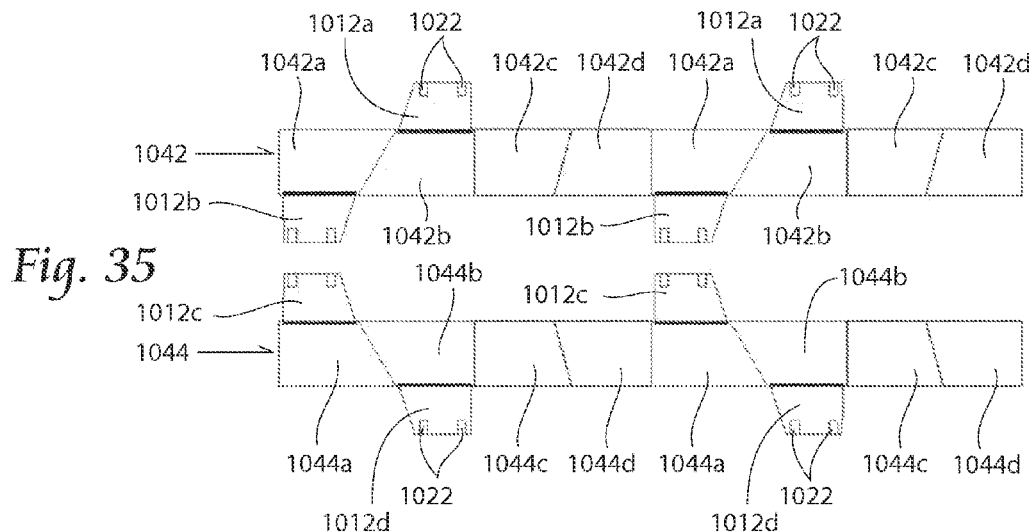

Referring to FIGS. 33 and 34, a wing web 1040, preferably non-woven for receiving folded tapes 1022 coupled to ears 1012 is shown, with wing web 1040 slit and spread such as in FIGS. 18 and 19, and the ear after cutting, repitching and rotation, is introduced to the wing web as shown in FIG. 35 (similar to FIG. 20 above).

As can be seen in FIG. 35, the folded tapes 1022 coupled to ears 1012 are introduced in the fashion shown, with the 1042 lane of wing web material receiving folded tapes 1022 coupled to ears 1012 in orientation 1012*a* coupled to a wing web portion 1042*b*, such that the short edge of the trapezoid in the cross-machine direction (left to right) receives the long edge of the ears 1012 from the 1012*a* orientation. The short edge of wing web portions 1042*a* in the cross-machine direction receives the long edge of ear 1012 in the 1012*b* orientation. The configuration that results is pictured in FIG. 35, also regarding lane 1044 of wing web material with the short portions of portions 1040*a* in the cross-machine direction receiving ears 1012 in the 1012*c* orientation on the long side of the 1012*c* orientation in the cross-machine direction, and similarly with portions 1044*b* receiving 1012*d* orientated ears 1012*d* as shown.

Figure 36:
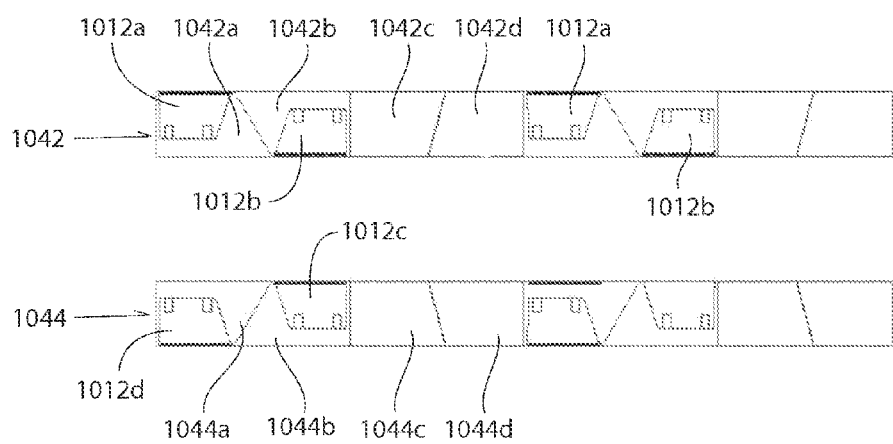
Figure 41:
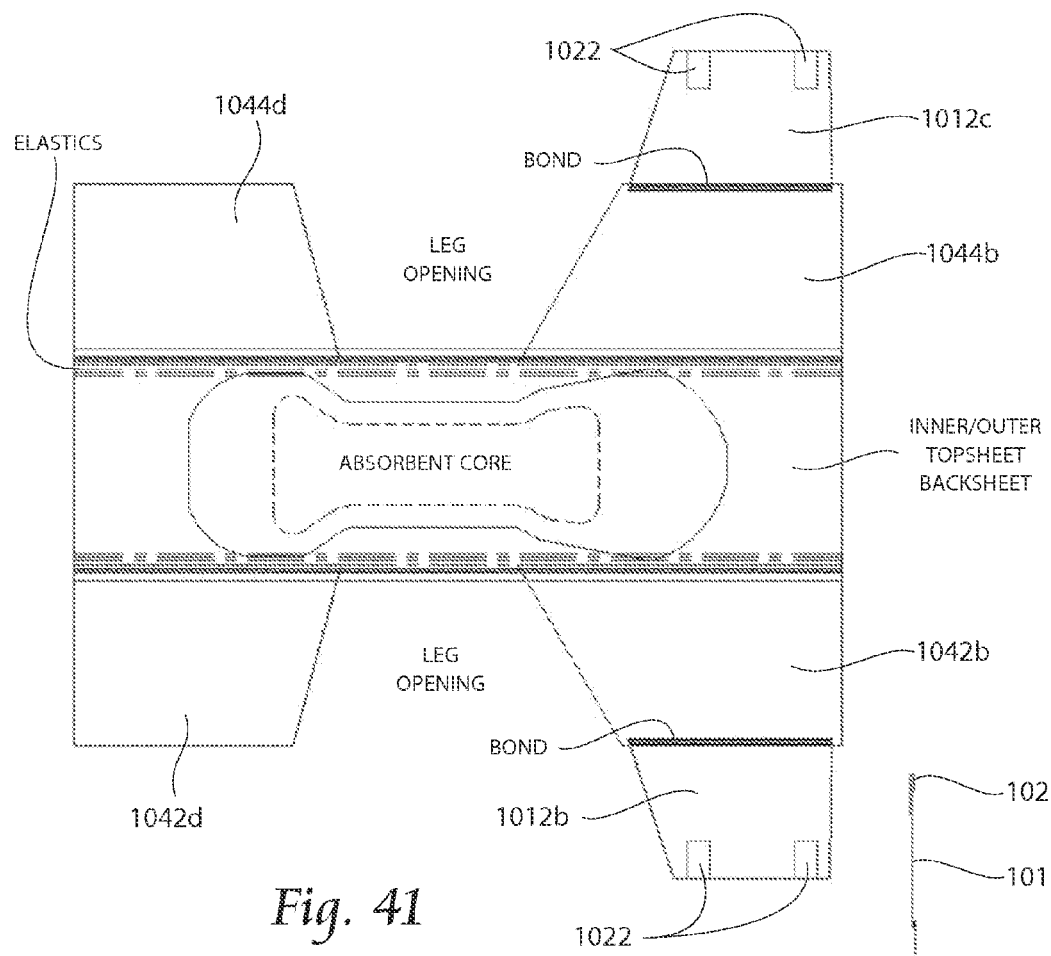
Figure 42:
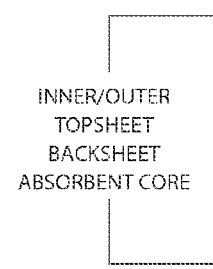

All of the ears are then folded down as shown in FIG. 36, such that portions 1042*a* and 1042*b* host ears 1012, while portions 1042*c* and 1042*d* do not host ears. Portions 1044*a* and 1044*b* host ear portions 1012 orientaed in the 1012*c* and 1012*d* orientations, respectively. In FIGS. 36-40, the process continues as shown, similar to the process described above in relation to FIGS. 21-27. A representative product as shown in FIG. 41 is formed thereby, its cross section shown in FIG. 42.

Figure 37:
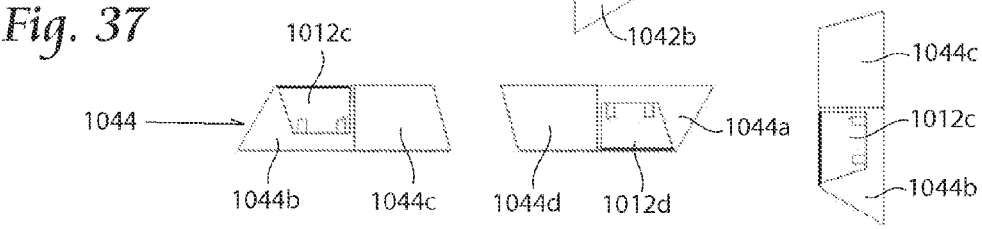

Referring to FIG. 37, it is seen that every other of the pair of elements from the 1042 lane are rotated. The 1042*d* and adjacent 1042*a* elements are not rotated, while the 1042*b* and adjacent 1044*c* are rotated 180° into sequence. Similarly with respect to lane 1044, elements 1044*c* and 1044*b* are rotated into sequence while elements 1044*a* and 1044*d* are not rotated in orientation relative to the machine direction.

What can be seen in FIG. 38 is that the elements have been positioned properly to be deposited onto a chassis web (preferably pre-formed with the elements such as an absorbent core, top sheet and back sheet as shown, but not labeled in the remaining figures). All of the folding of the ear portions 1012 on the wing portions 104*s* are to the top of lane 1042 and the bottom of lane 1044, so that when a chassis portion is coupled between lanes 1042 and 1044 as shown in FIG. 39, the wings 1042*a* carrying ears 1012*d* and 1044*a* can form two waist-wrapping portions. The space between elements 1042*a* and 1042*c* will form left leg portions and the space between elements 1044*a* and 1044*c* will form right leg portions.

Referring now to FIG. 40, the elements 1042*a* (carrying ear 1012*a*), 1042*b* (carrying ear 1012*b*), 1042*c* and 1042*d*, as well as 1044*a* (carrying ear 1012*d*), 1044*b* (carrying ear 1012*c*), 1044*c* and 1044*d* are folded over to be in-line with the chassis web 10.

Referring now to FIGS. 43-60, and additional embodiment is formed using the procedure shown therein.

Referring to FIG. 43, a laminate is shown after slit stretching (501-504), and four lanes of hook material 505 are shown below. In FIG. 44, the hooks 505 are shown attached to the stretch laminate webs 501-504, while additional slit outer non-woven web 510 and 512 is introduced, and as shown in FIG. 45, the stretch laminate webs 501-504 are coupled to outer non-woven webs 510 and 512 as shown, for instance by ultrasonic bond methods.

Next, as shown in FIG. 46, the side panel laminate is folded as shown. The side panel laminate is slit as shown in FIG. 47, forming side panel assemblies 501/501*a*, 502/501*b*, 503/501*c*, and 504/501*d* respectively. Next, the back ear web 610*a*, 610*b* (preferably non-woven) as shown being formed in FIG. 51 and slit in FIG. 52, are introduced, preferably in slip/cut fashion to and coupled with the side panel assemblies 501/501*a*, 502/501*b*, 503/501*c*, and 504/501*d* as shown in FIG. 48.

The side panel assemblies 501/501*a*, 502/501*b*, 503/501*c*, and 504/501*d* are then folded and preferably temporarily staked together as shown in FIG. 49.

Figure 50A:
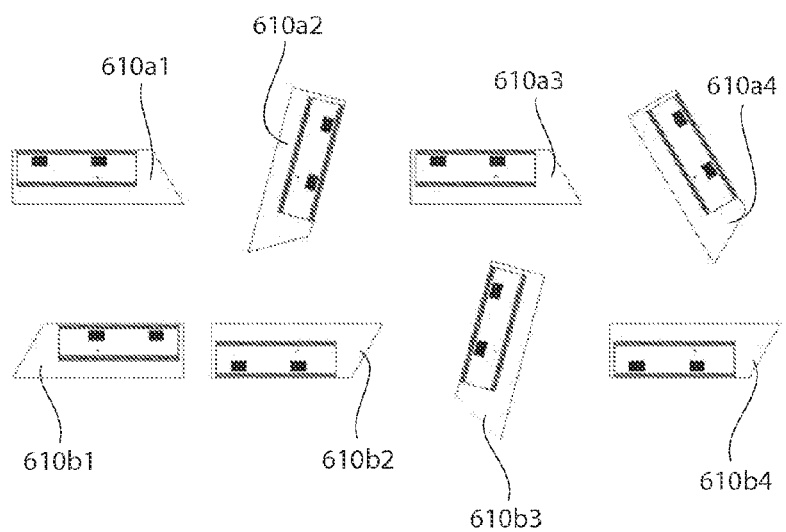
Figure 50B:
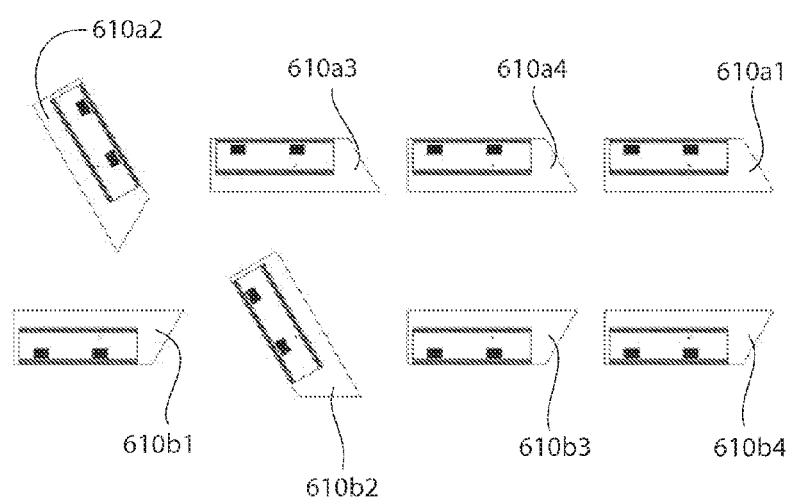

Next, the side panel assemblies side panel assemblies 501/510*a*, 502/510*b*, 503/510*c*, and 504/510*d* coupled with respective back ear web portions 610*a*1, 610*a*2, 610*a*3, and 610*a*4, and 610*b*1, 610*b*2, 610*b*3, and 610*b*4 are die cut, repitched and rotated according to FIGS. 50*a* to result in the end orientation shown in FIG. 50*b*, wherein every other of 610*a*1, 610*a*2, 610*a*3, and 610*a*4 has been rotated 180 degrees, and every other of 610*b*1, 610*b*2, 610*b*3, and 610*b*4 has also been rotated 180 degrees and rephrased to result in the matched folded right and left sets.

The front ear non-woven web 702/704, and particularly portions 702*a*, 702*b*, 702*c*, and 702*d*, and 704*a*, 704*b*, 704*c*, and 704*d* are shown being formed and slit in FIGS. 53 and 54, and then die cut, repitched, and rotated as shown in FIGS. 55-56.

As shown in FIG. 57, the front ear non-woven portions 702*a*, 702*b*, 702*c*, and 702*d*, and 704*a*, 704*b*, 704*c*, and 704*d* are introduced to and coupled about opposite sides of the chassis web 10, and the respective back ear web portions 610*a*1, 610*a*2, 610*a*3, and 610*a*4, having been properly aligned, as well as respective back ear web portions 610*b*1, 610*b*2, 610*b*3, and 610*b*4 also having been properly aligned, are likewise introduced to and coupled about opposite sides of the chassis web 10 as shown in FIG. 58, positioned alternating with front ear portions as shown.

Figure 59:
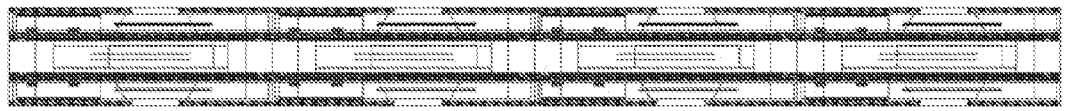

The front ear portions 702*a*, 702*b*, 702*c*, and 702*d*, and 704*a*, 704*b*, 704*c*, and 704*d*; and the back ear web portions 610*a*1, 610*a*2, 610*a*3, and 610*a*4; and 610*b*1, 610*b*2, 610*b*3, and 610*b*4; are all folded to conform with (slightly greater than, equal to, or slightly less than) the cross-machine directional width of the chassis 10 as shown in FIG. 59.

Figure 60:
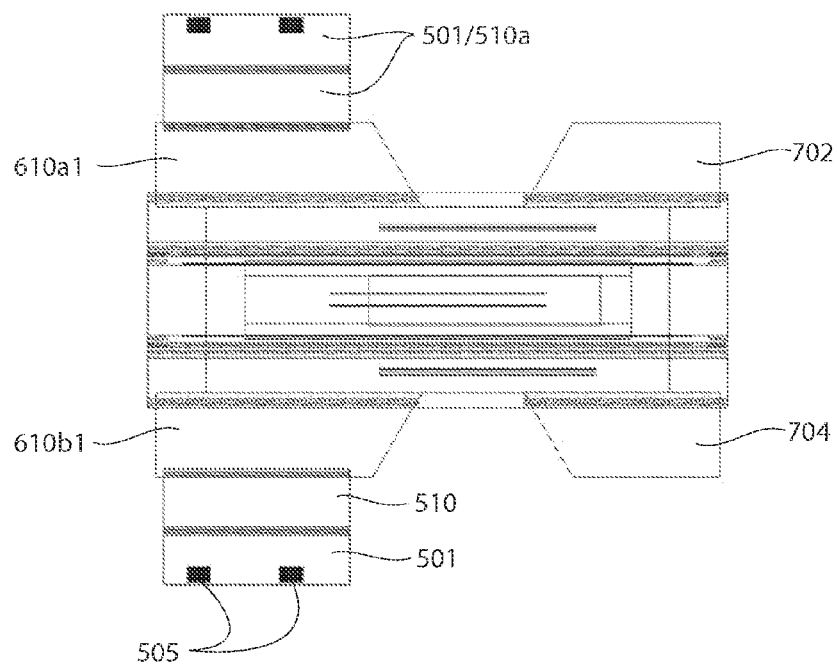

A product is formed having the configuration shown in FIG. 60.

Figure 61:
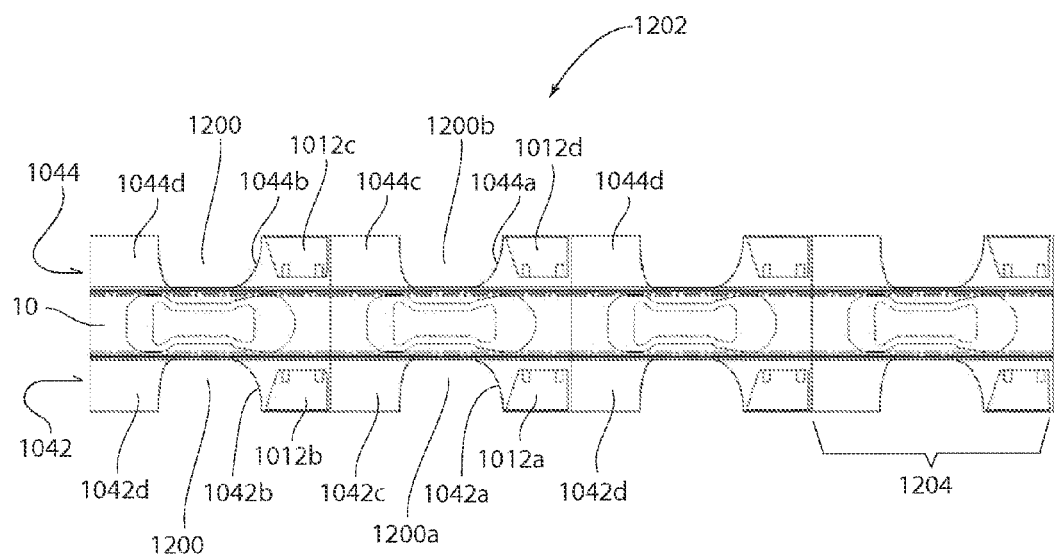
FIG. 61 is a plan view of wing assemblies coupled to a chassis assembly with chips removed from the wing assemblies.
Figure 62:
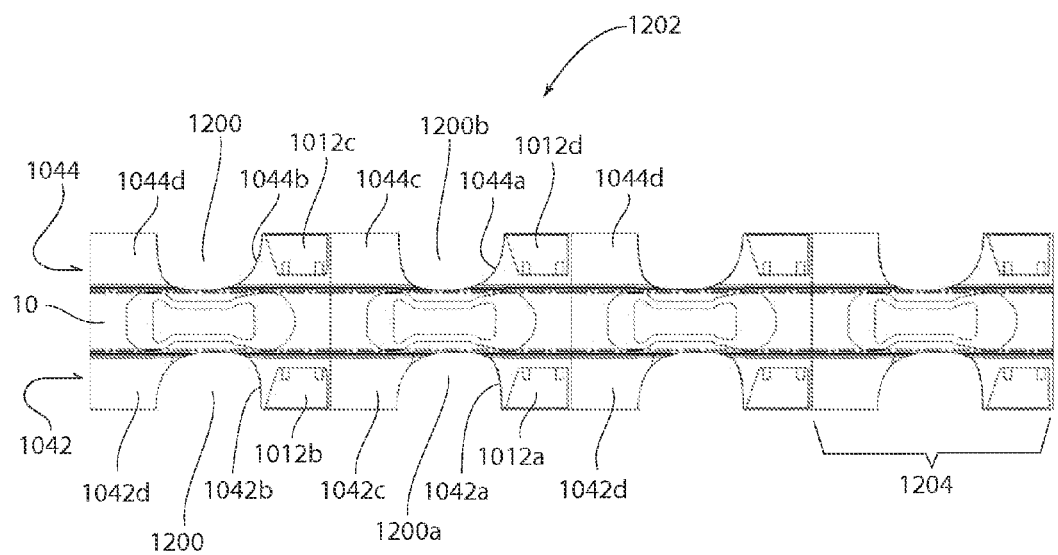
FIG. 62 is a plan view of wing assemblies coupled to a chassis assembly with chips removed from the wing assemblies and chassis assembly.

It is contemplated that it may be desirable to provide a disposable product with a contoured or curved leg opening 1200 by trimming a portion of a combined web 1202 after wings 1042*a*-1042*d*,1044*a*-1044*d* have been placed on the chassis web 10 as shown in FIGS. 61 and 62. For illustrative purposes, the combined web 1202 and resulting disposable garment 1204 of FIGS. 39-41 are shown in FIGS. 61 and 62, however, it should be understood that the methods described herein may be utilized on any combined web. Preferably, the combined web 1202 includes a chassis web 10, a plurality of ear carrying wings 1042*a*, 1042*b*, 1044*a*, 1044*b* and non-ear carrying wings 1042*c*, 1042*d*, 1044*c*, 1044*d* as shown in FIG. 39.

Preferably, a portion of the ear carrying wings 1042*a*, 1042*b*, 1044*a*, 1044*b* and the non-ear carrying wings 1042*c*, 1042*d*, 1044*c*, 1044*d* on each side of the garment 1204 may be removed to create a contoured shape, as shown in FIG. 61. However, it is also contemplated that a portion of the chassis web 10 between the ear carrying wing 1042*a*, 1042*b*, 1044*a*, 1044*b* and non-ear carrying wing 1042*c*, 1042*d*, 1044*c*, 1044*d* may also be removed to create a contoured shape as shown in FIG. 62. For example, as shown in FIG. 61, a portion of the chassis web between a first non-ear carrying wing portion 1042*d* and a first ear carrying wing portion 1042*b* has been removed.

It is contemplated that any means known in the art may be utilized to remove the desired portions of the wings 1042*a*-1042*d*,1044*a*-1044*d* and, if desired, chassis web 10, to create the contoured leg opening 1200. For example, and not by way of limitation, a knife roll may be utilized to cut the garment leg opening 1200 to the desired contour. In such a system, a contoured knife roll, with a cutting edge sized and configured to cut the leg opening 1200 to the desired shape would be provided.

It is contemplated that both the left 1200*a* and the right 1200*b* leg opening could be cut at the same time for example with a knife roll with two cutting surfaces, or that a pair of knife rolls, one for the left leg opening 1200*a* and one for the right leg opening 1200*b* may be utilized. Each knife roll is provided with an associated anvil, as is well known in the art. In use, the anvil and the knife roll each rotate, with the combined web 1202 to be cut between the surface of the knife roll and the anvil. As the knife roll rotates, the cutting edge cuts the combined web 1202 against the anvil.

Figure 63:
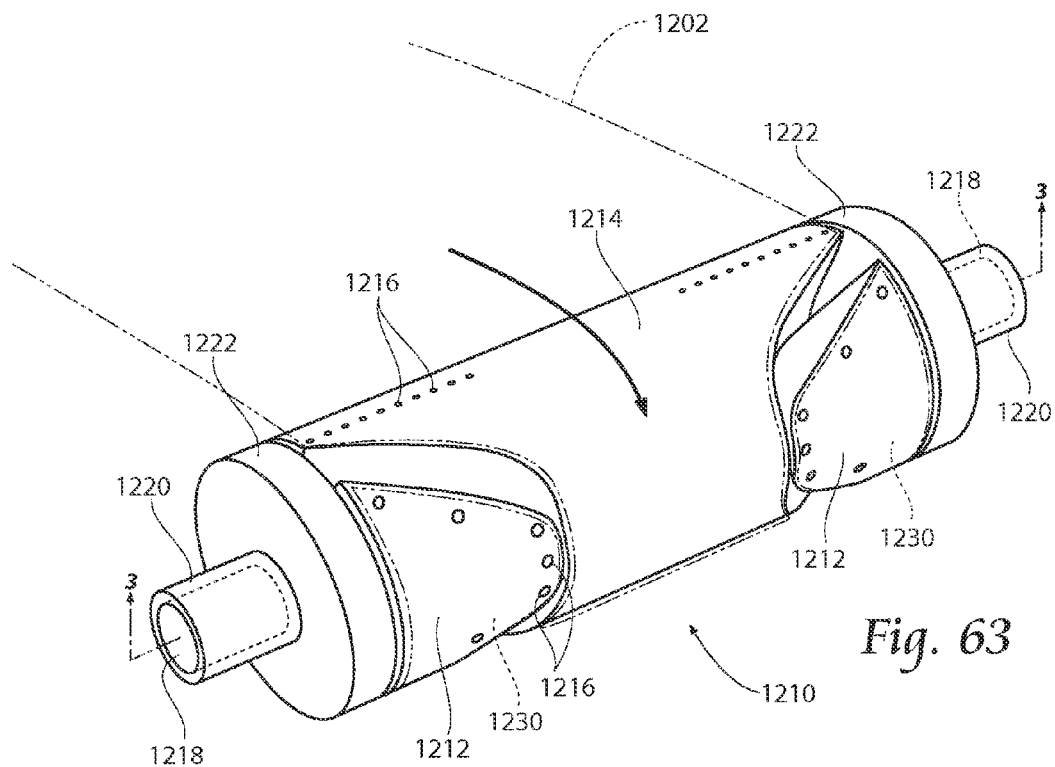
FIG. 63 is a perspective view of a trim removal system of the present invention, with an infeed chassis web, and a chip to be removed therefrom.
Figure 76:
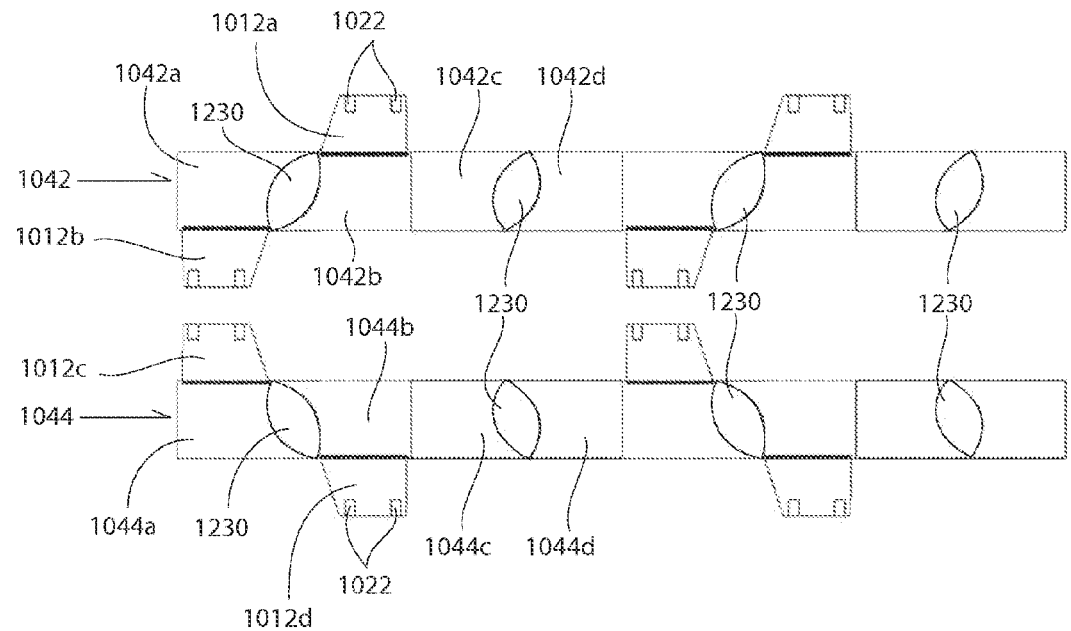
FIG. 76 is a plan view of a web of wing assemblies with chips removed from each wing assembly.

It is further contemplated that a trim removal system 1210 such as shown in FIG. 63 may be utilized to remove the cut chips from the combined web 1202. FIG. 63 shows an infeed web 1202, and a chip or chips 1230 to be removed therefrom. A transfer roll 1214 and an associated trim shoe or trim shoes 1212 are provided to engage the combined web 1202 and chips 1230. Preferably, the trim shoes 1212 are shaped complimentary with the chips 1230. Vacuum ports 1216 are provided on the transfer roll 1214 and trim shoes 1212 for maintaining the combined web 1202 and chips 1230 in close contact with the transfer roll 1214 and trim shoes 1212. It is noted that other methods of cutting the web, in addition to the particular trim removal system 1210 may be used to form the products of the present invention. It is also noted that the chip removal system 1210 as pictured, is configured to cut two chips 1230 from the incoming web 1202 at outboard portions of the incoming web 1202. Different shoe 1212 configurations can be used to cut different sized and/or shaped chips 1230, such as the chips 1230 desired to be removed from successive back ears 1042*a* and 1042*b* as shown in FIG. 76, or chips 1230 from between successive front ears 1042*c* and 1042*d* as shown in FIG. 76 if desired. Compare FIGS. 76 showing chips removed between successive front ears 1042*c* and 1042*d*, and FIG. 77, with no chips between front between front ears 1042*c* and 1042*d*.

An inner axle 1218 and an outer axle 1220 are coupled to the transfer roll 1214 (or hub 1222) and the trim shoes 1212, respectively. The inner axle 1218 and the outer axle 1220 are capable of being operated at different speeds in relation to one another by servo motor (not shown). This difference in speed allows the trim shoes 1212 to rotate faster or slower with respect to the transfer roll 1214 as desired. In use, as will be described later, this speed differential creates a ripping effect by first pulling the combined web 1202 away from the chip 30 as the transfer roll 1214 is rotating faster than the shoe 1212, then by pulling the chip 1230 away from the combined web 1202 as the shoe 1212 is rotating faster than the transfer roll 1214.

Figure 64:
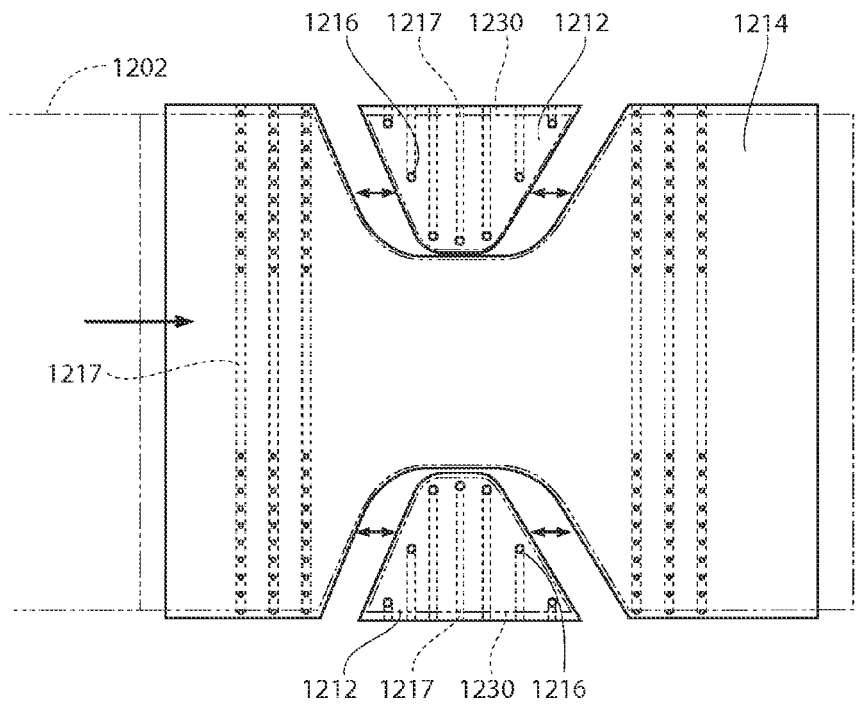
FIG. 64 is a two dimensional representation of the trim removal system of FIG. 63.

Referring now to FIG. 64, a two dimensional representation of the trim shoe 1212 and transfer roll 1214 of FIG. 63 is shown. As can be seen, vacuum channels 1217 communicate with vacuum ports 1216 on both the trim shoe 1212 and transfer roll 1214 to maintain control of the chip 1230 and combined web 1202. From this perspective, it can be seen that different rotational speeds of the trim shoe 1212 and transfer roll 1214 will cause a ripping effect by first pulling the web 1202 away from the chip 1230 as the transfer roll 1214 is rotating faster than the shoe 1212, then by pulling the chip 1230 away from the combined web 1202 as the shoe 1212 is rotating faster than the transfer roll 1214.

Figure 65:
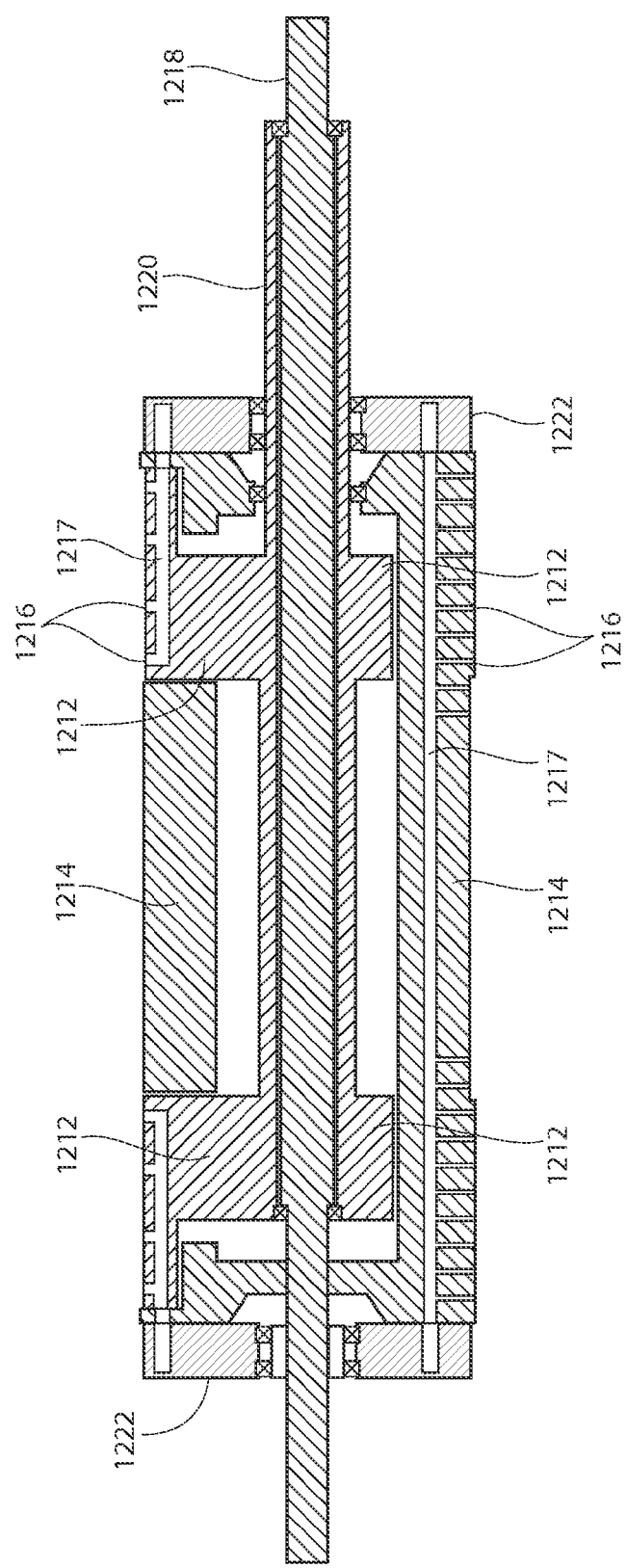
FIG. 65 is a cross sectional view of a trim removal system.

FIG. 65 is a cross sectional view of a trim shoe 1212 and transfer roll 1214 of the present invention. As can be seen, vacuum is communicated to ports 1216 through channels 1217, which are coupled to a source of vacuum (not shown). Rotation of the outer axle 1220, which is coupled to the shoe 1212, causes rotation of the shoe 1212. The inner axle 1218 is coupled preferably to hub 1222 and to transfer roll 1214.

Referring now to FIGS. 66-71, a sequence is shown of the trim removal system 1210 removing chips 1230 and discharging them, and then the system 1210 returning to its initial position to remove more chips 1230 from the next segment of web 1202. FIGS. 72-75 are plan views of the position of the chips 1230 relative to the web 1202 at the positions associated with FIGS. 66-68 respectively, demonstrating the ripping effects of the present invention.

Figure 66:
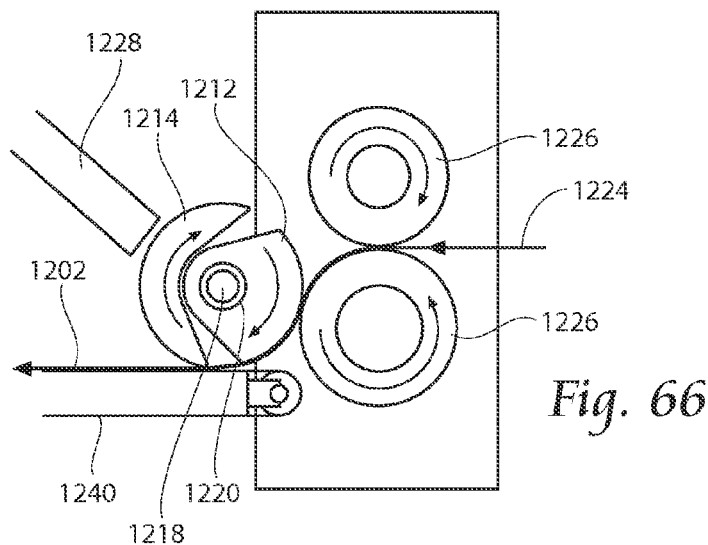
FIG. 66 is a schematic view of a trim removal system receiving an article from a transfer roll in an initial chip engaging position.

Referring now to FIG. 66, a schematic view of the system 1210 is shown receiving an infeed web 1202. In this figure, die and anvil system 1226 is shown rotating to engage the web 1202 and cut from it chips 1230 (not apparent in this view), as is well known in the art. Unfortunately, the die of the die and anvil system 1226 is susceptible to wear and tear and requires replacement once the die dulls to an unacceptable condition.

In this view, the trim shoe 1212 can be seen in an initial chip engaging position, aligned to receive the chip 1230 of the web 1202 onto the shoe 1212, which, as described previously, will be urged against the surface of the shoe 1212 by vacuum ports 1216. The trim shoe 1212 will be seen to be rotating about outer axis 1220. In this view, a discharge chute 1228 is shown for ultimately receiving waste chips 1230, and an outfeed conveyor 1240 is provided for receiving the web 1202 with the chip 1230 removed, for further processing and manufacturing steps in the composition of the disposable garments, as desired.

Inner axle 1218 is preferably operated at a first continuous speed, rotating hub 1222 and transfer roll 1214 at a continuous speed, consistent with the infeed speed of the web 1202. At this initial chip engaging position shown in FIG. 66, the outer axle 1220, and associated shoes 1212, are rotated at the same speed as the inner axle 1218.

Figure 72:
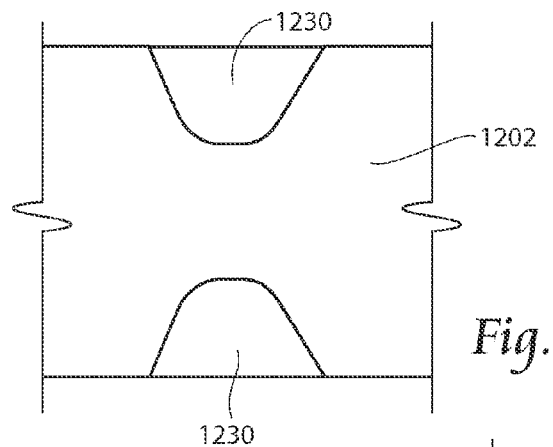
FIGS. 72-75 are plan views of the position of the chip relative to the web, demonstrating the ripping effects of the present invention.
Figure 73:
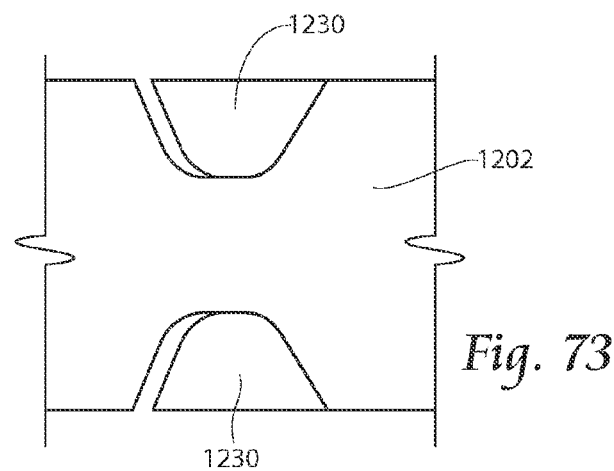

The position of the chip 1230 relative to the web 1202 is shown in FIG. 72 for the initial chip engaging position. In this position, the anvil and die 1226 has created a sever, but the chip 1230 and web 1202 could remain somewhat coupled depending on the sharpness of the die 1226. The severing method shown in the figures, particularly the severing trim removal device 1210 is just one method of forming the novel products of the present invention, other methods of severing and/or trim removal may be used.

Figure 67:
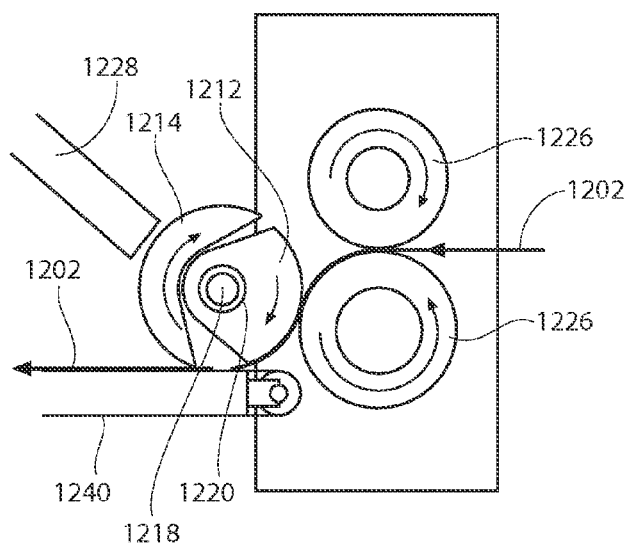
FIG. 67 is a schematic view of the trim removal system separating a first article from a second article.

Referring now to FIG. 67, the outer axle 1220, and associated shoes 1212, are toggled slower than inner axle 1218 to allow the web 1202 to be ripped from the chip 1230 at the leading edge of the chip 1230 in the machine direction. It is apparent in this view that the distance between the trailing edge of the shoes 1212 has become closer to the leading edge of the transfer roll 1214. This ripping is caused by the main web 1202 being ripped away from the chip 1230 at the leading edge of the chip 1230 as is shown in associated FIG. 73.

Figure 68:
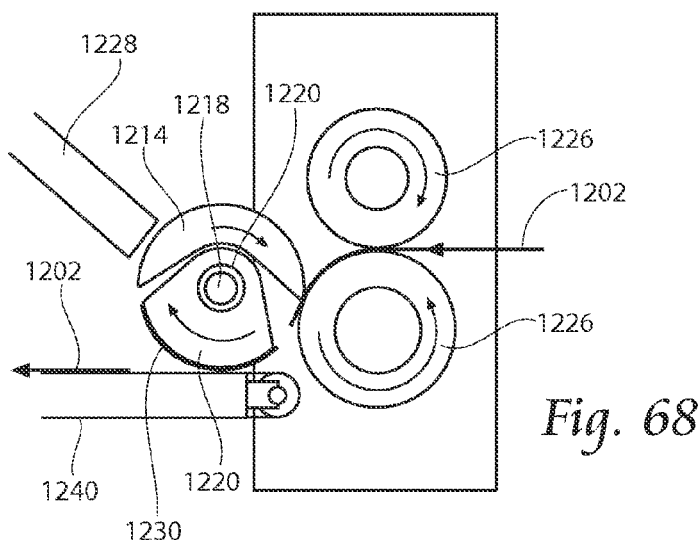
FIG. 68 is a schematic view of the trim removal system separating trim from the first article.
Figure 74:
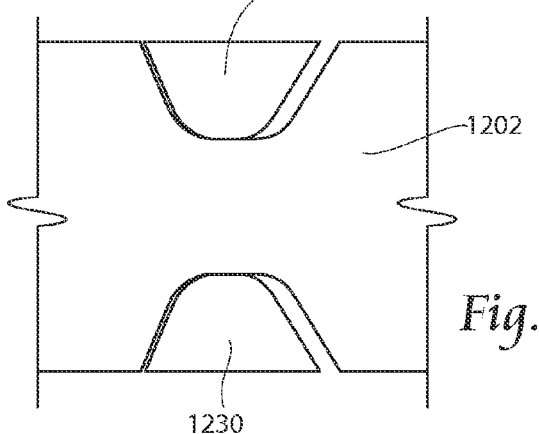

Referring now to FIG. 68, the outer axle 1220 is toggled equal to and then faster than the inner axle 1218, to allow the chips 1230 to rip from the web 1202 at the trailing edge of the chips 30 as is shown in associated FIG. 74. At this point in the process, the chip 1230 will be removed from the web 1202 by ripping first the main web 1202 away from the chip 1230 at the leading edge of the chip 1230, and next by ripping the trailing edge of the chip 1230 from the web 1202.

Figure 75:
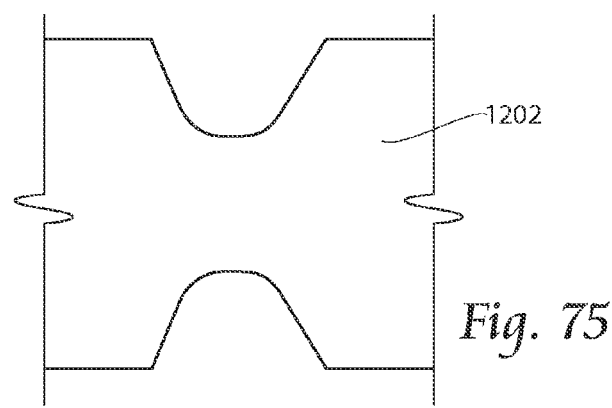

The outfeed conveyor 1240 is provided for receiving the web 1202 with the chip 1230 removed as shown in FIG. 75, for further processing and manufacturing steps in the composition of the disposable garments, as desired. The vacuum of the transfer roll 1214 can be turned off at this point to allow for release of the web 1202 to the conveyor, for instance in accordance with application Ser. No. 11/141,552, entitled "High Speed Vacuum Porting" which is incorporated herein by reference.

Figure 69:
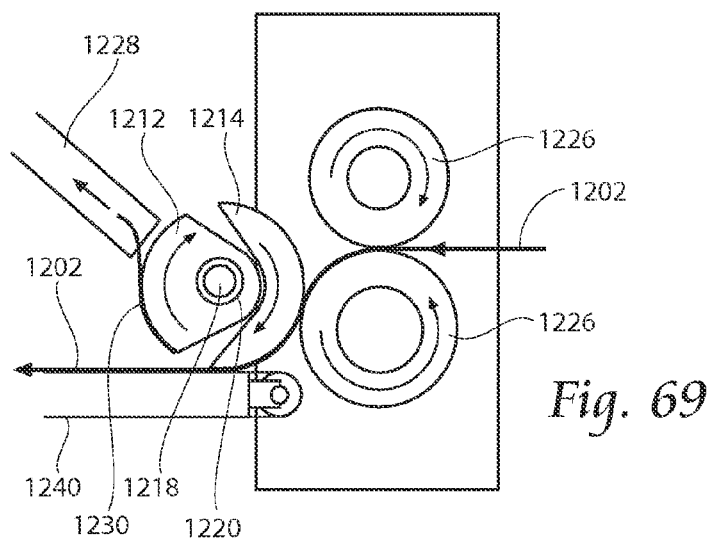
FIG. 69 is a schematic view of the trim removal system discharging the trim.
Figure 70:
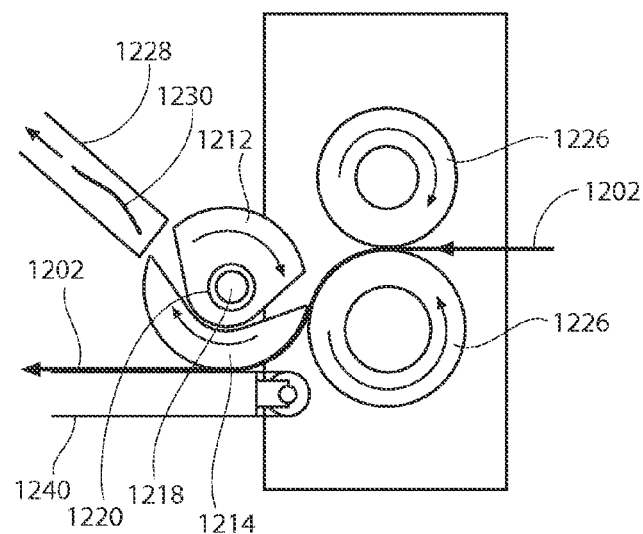
FIG. 70 is a schematic view of the trim removal system returning to its initial chip engaging position.
Figure 71:
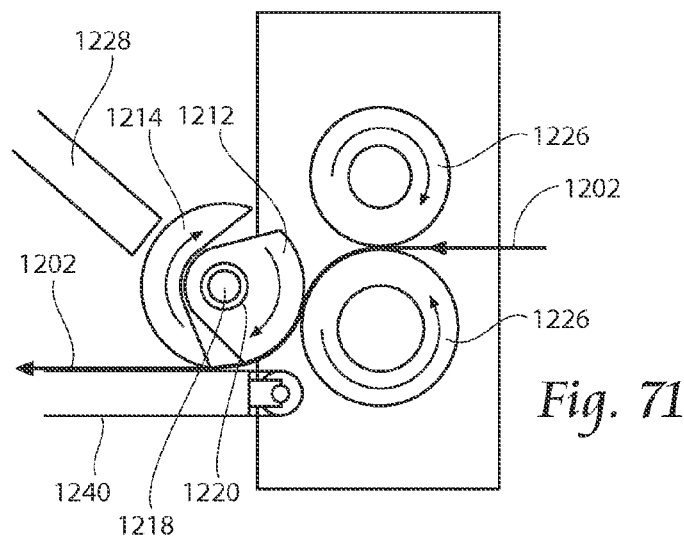
FIG. 71 is a schematic view of the trim removal system returned to its initial chip engaging position.

Referring now to FIG. 69, the chip 1230 is discharged into a discharge chute 1228, which is preferably vacuum assisted, although other collection means would satisfactorily accomplish the function of collecting waste chips 1230. It is noted that vacuum is allowed to turn off of the shoes 1212 to allow the chips 1230 to release into the chute 1228. Alternatively a vacuum in the chute 1228 could simply be provided that is stronger than the vacuum applied to the shoes 1212.

The rotational speed of the shoes 1212 and outer axle 1220, which were first operated at a speed roughly equal to inner axle 1218, rotating hub 1222 and transfer roll 1214, initially decreased, or lagged as is shown by comparing FIG. 66 with FIG. 67.

Next, the rotational speed of the shoes 1212 and outer axle 1220, increased, or surged relative to the inner axle 1218, rotating hub 1222 and transfer roll 1214.

In order to return to the initial chip engaging position, the rotational speed of the shoes 1212 and outer axle 1220, must again decrease, or lag relative to the inner axle 1218, rotating hub 1222 and transfer roll 1214. This lag is apparent by comparing FIG. 68 to FIGS. 69, 70 and 71. Finally, in FIG. 71, through one revolution, the system 1210 has removed and discharged the chips 1230, discharged the web 1202 for further processing, and the shoes 1212 have been returned to their initial position to remove more chips 1230 from the next segment of web 1202.

It is contemplated that the die of the die and anvil system 1226 in the above described trim removal apparatus may be replaced by a perforating apparatus. The perforating apparatus preferably forms the chips 1230 on the web 1202, but does not completely sever the chips 1230 from the web 1202. The perforated chips 1230 perforated could then be removed from the web 1202 in the same manner described above. The perforating apparatus may take any form known in the art including, but not limited to, a perforating die roll.

It is further contemplated that the chips may be removed from the wings 1042a-1042d,1044a-1044d prior to attaching the wings 1042a-1042d,1044a-1044d to the chassis web 10. The chips may be removed from the wings 1042a-1042d, 1044a-1044d, using any means known in the art. For example, the wing web 1042,1044 may be fed between an anvil and knife roll, the knife roll having a cutting edge sized and configured to cut the desired chips from the wings 1042a-1042d,1044a-1044d.

Although the illustrated embodiments of FIGS. 61, 62 and 76 show a particular configuration or shape of chip being removed from the wings 1042a-1042d,1044a-1044d and web 10, is contemplated that the chips removed from the wings 1042a-1042d,1044a-1044d could take any desired shapes to provide a contoured leg opening 1200.

Figure 77:
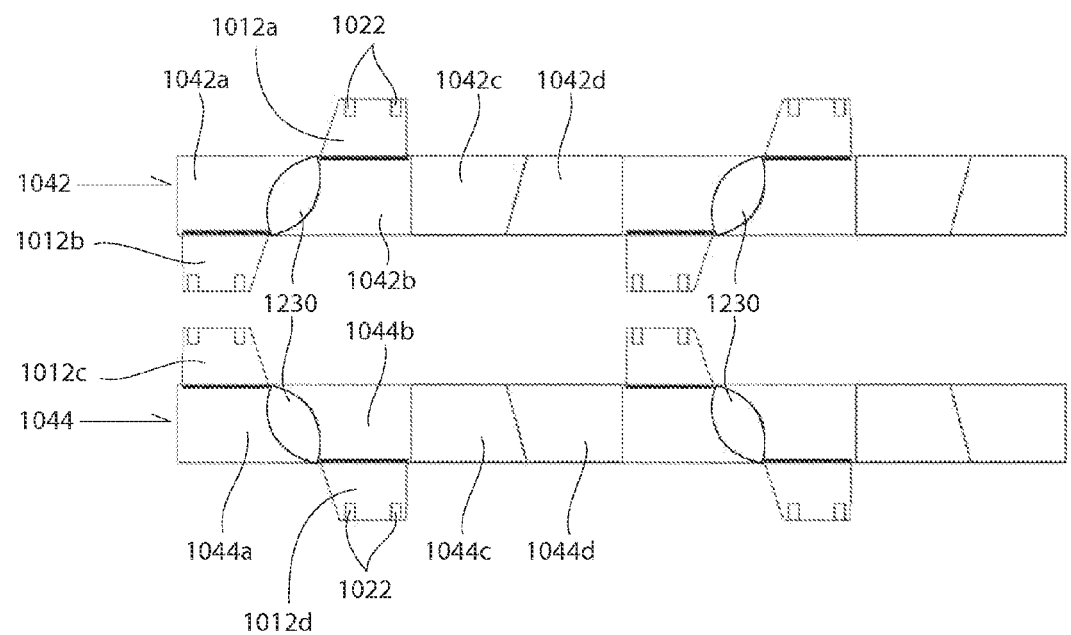
FIG. 77 is a plan view of wing assemblies with chips removed from the selected wing assemblies.

It is further contemplated that, if desired, chips could be removed from only the ear carrying wings 1042a, 1042b, 1044a, 1044b or the non-ear carrying wings 1042c, 1042d, 1044c, 1044d. For example, FIG. 77 shows a chip removed from only the ear carrying wings 1042a, 1042b, 1044a, 1044b. The chips may be cut from the desired wings 1042a-1042d,1044a-1044d using any means known in the art, including those means described above.

Figure 78:
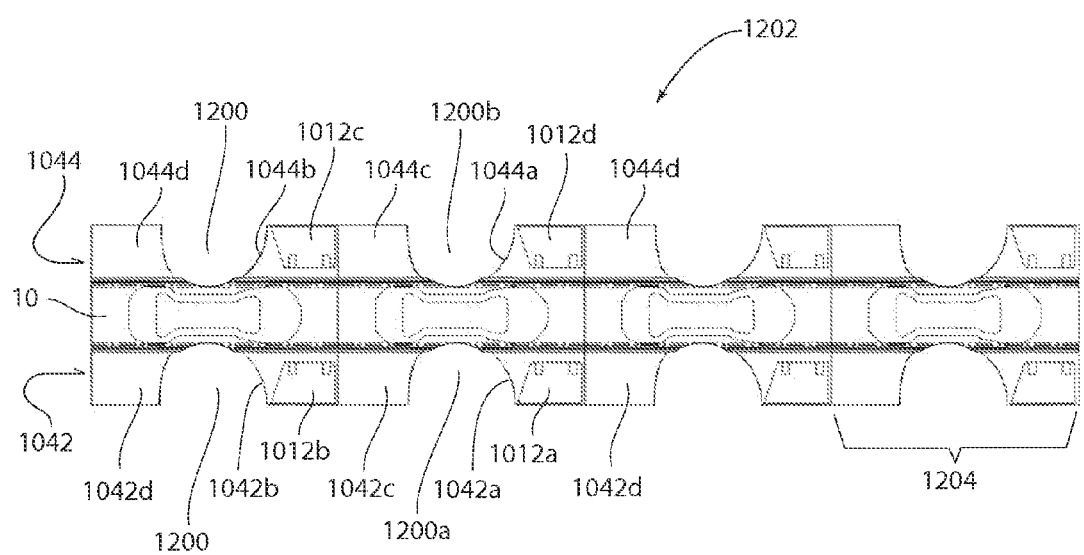
FIG. 78 is a plan view of wing assemblies coupled to a chassis assembly with chips removed from the wing assemblies and chassis assembly.

It is further contemplated that chips may be removed from the wings 1042a-1042d,1044a-1044d and the chassis 10 in separate steps as shown in FIG. 78. For example, chips may be cut from the wings 1042a-1042d,1044a-1044d in a first step and then cut from the web 10 in a second step, or vice versa. The chips may be cut from the wings 1042a-1042d, 1044a-1044d and web 10 using any means known in the art, including those means described above.

Referring now to FIGS. 79-90, using the principles of the present invention, several product configuration variations are shown. For instance, it is possible to pre-apply either front 1042 (c or d) or 1044 (c or d) or back 1042 (a or b) or 1044 (a or b) ears to a chassis web using previously known slip/cut techniques (e.g., the slip/cut applied ears 1144 shown in FIG. 79), and then use the alternate rotation technique of the present invention to assemble a novel product configuration (see., e.g., FIG. 79). Similarly, it is possible to post-apply either front or back ears to a chassis web using previously known slip/cut techniques, after using the alternate rotation technique of the present invention to assemble a novel product configuration, resulting in a configuration such as FIG. 79. In this method, the slip/cut technique is used to, for instance, apply each front ear 1144 (both left and right front ears 1144, FIG. 79), and the alternating rotation technique described previously is used to apply each back ear portion (e.g., 1042b and 1044b, FIG. 79)

Figure 79:
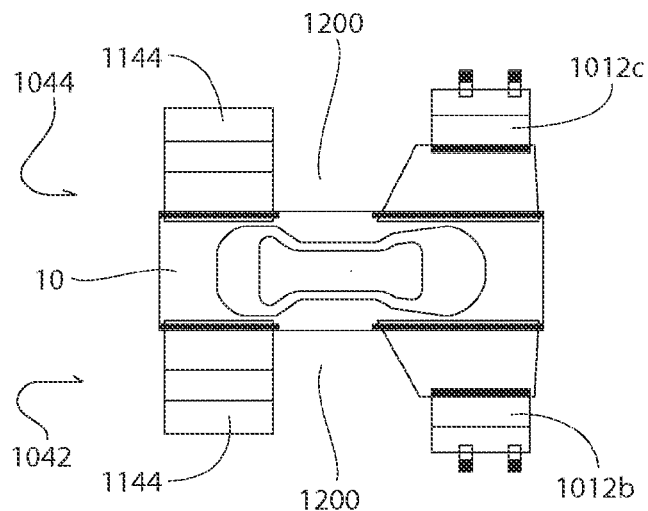
FIG. 79 is a plan view of a product variation showing a slip/cut applied front ear, alternately rotated back ears, and extension panels extending from the back ears.

Additionally, it is seen that extension panels 1012 can be applied or not, if desired (compare FIG. 79 with extension panels 1012 and FIG. 85, without extension panels 1012) to the back ear portions 1044 if desired, and that those extension panels 1012 can be paired with the back ears 1044 with the extension panels 1012 in pre-folded (or unfolded) condition if desired (e.g., shown unfolded, with fold lines, on FIG. 79). Additionally, front ear portions 1144 can arrive at the chassis web in a pre-folded condition (e.g., shown unfolded, with fold lines, on FIG. 79), if a wider front ear portion 1144 is desired. These configurations can also be combined with the chip removal technique previously discussed (or any other chip removal or die cutting or ear web formation technique), in which curved portions of either one or both ears 1144, 1044, or 1042, or a leg portion 1200a and 1200b of the chassis, or any combination of the foregoing (see, e.g., FIGS. 80 and 81), the product configurations of FIGS. 79-90 can be achieved.

Referring to FIG. 79, a plan view of a product variation showing slip/cut applied front ears 1144, alternately rotated back ears 1042, 1044, and extension panels 1012 extending from the back ears 1042, 1044 is shown.

Figure 80:
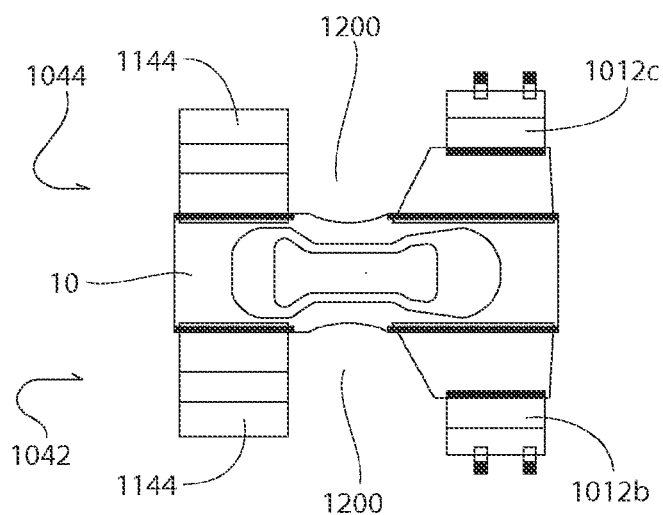
FIG. 80 is a plan view of a product variation showing a slip/cut applied front ear, alternately rotated back ears, and extension panels extending from the back ears, and a die cut chassis.

Referring to FIG. 80, the embodiment of FIG. 79 is shown, with the additional product feature of leg portions 1200*a* and 1200*b* of the chassis removed from the chassis, to fit around the leg of a wearer.

Figure 81:
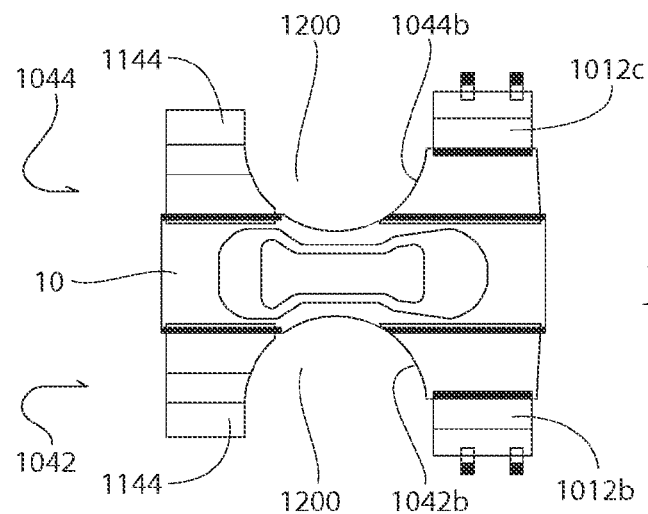
FIG. 81 is a plan view of a product variation showing a slip/cut applied front ear, alternately rotated back ears, and extension panels extending from the back ears, die cut front and back ear portions, and a die cut chassis.

Referring to FIG. 81, the embodiment of FIG. 80 is shown, with the additional product feature of chips 1230 having been removed from both the front ear and back ear portions of the product, for instance using the severing and chip removal pattern of FIG. 76.

Figure 82:
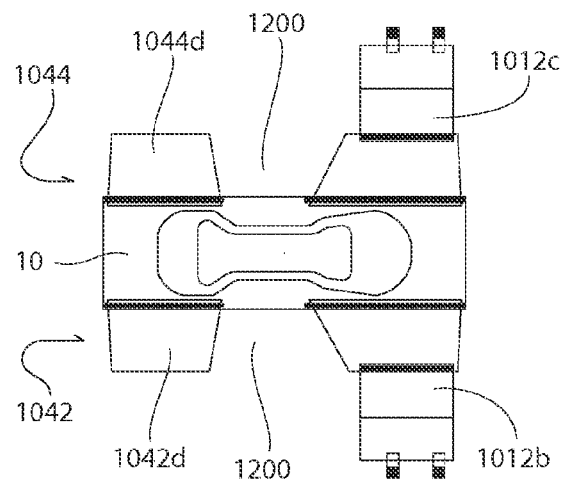
FIG. 82 is a plan view of a product variation showing alternately rotated front ears, alternately rotated back ears, and extension panels extending from the back ears.

Referring to FIG. 82, a plan view of a product variation showing alternately rotated front and back ears using the techniques described above (e.g., using the technique to construct the embodiments shown in FIG. 28 and/or FIG. 60 above) is shown.

Figure 83:
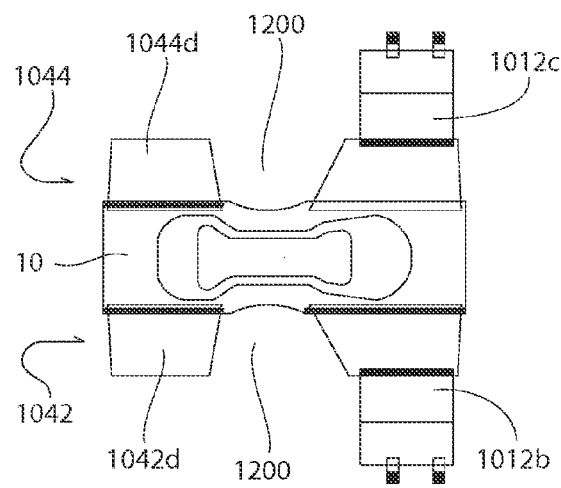
FIG. 83 is a plan view of a product variation showing alternately rotated front ears, alternately rotated back ears, extension panels extending from the back ears, and a die cut chassis.

Referring to FIG. 83, the embodiment of FIG. 82 is shown, with the additional product feature of leg portions 1200*a* and 1200*b* of the chassis removed from the chassis, to fit around the leg of a wearer.

Figure 84:
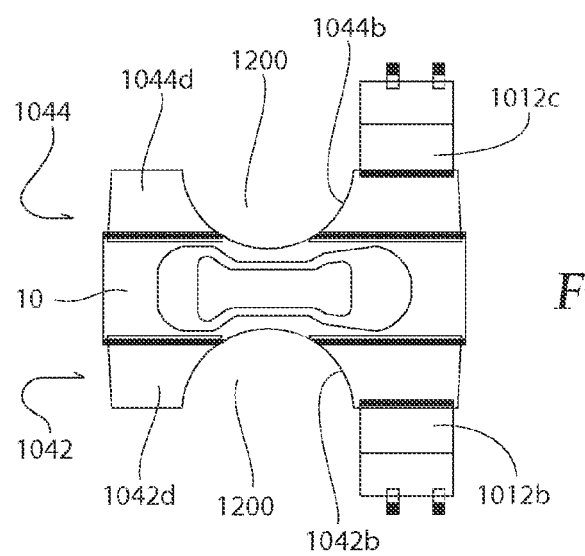
FIG. 84 is a plan view of a product variation showing alternately rotated front ears, alternately rotated back ears, extension panels extending from the back ears, a die cut chassis, and die cut ears.

Referring to FIG. 84, the embodiment of FIG. 83 is shown with the additional product feature of chips 1230 having been removed from both the front ear and back ear portions of the product, for instance using the severing and chip removal pattern of FIG. 76.

Figure 85:
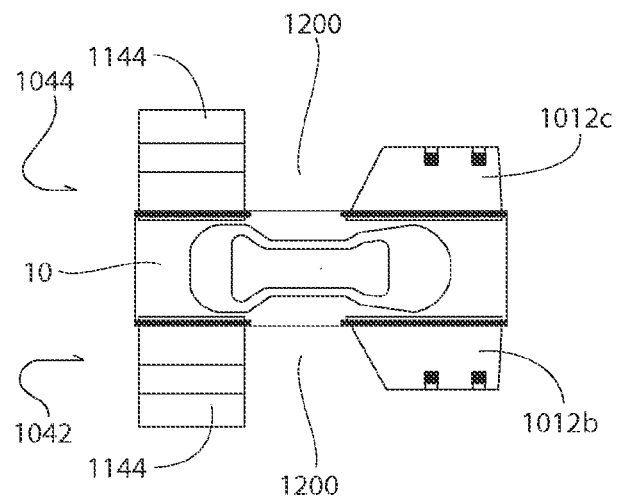
FIG. 85 is a plan view of a product variation showing slip/cut applied front ears, and alternately rotated back ears.

Referring to FIG. 85 a plan view of a product variation showing slip/cut applied front ears 1144, and alternately rotated back ears is shown.

Figure 86:
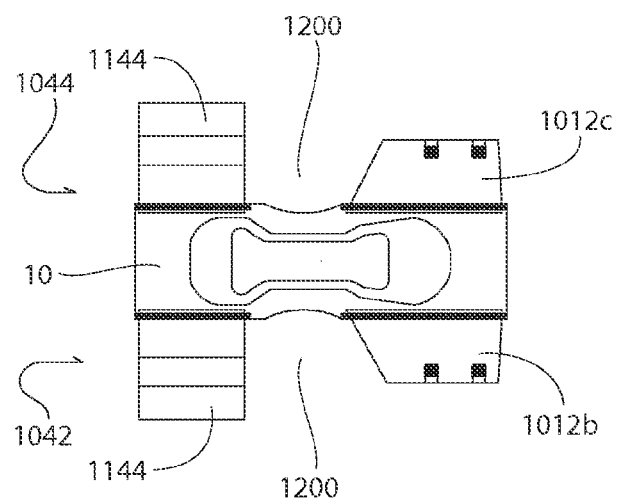
FIG. 86 is a plan view of a product variation showing slip/cut applied front ears, and alternately rotated back ears, and a die cut chassis.

Referring to FIG. 86, the embodiment of FIG. 85 is shown, with the additional product feature of leg portions 1200*a* and 1200*b* of the chassis removed from the chassis, to fit around the leg of a wearer.

Figure 87:
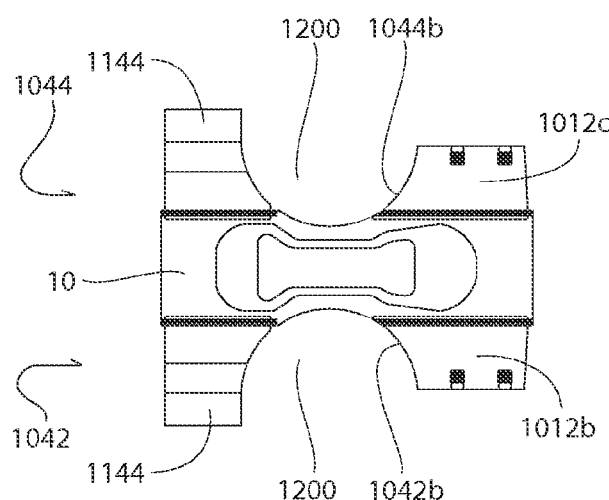
FIG. 87 is a plan view of a product variation showing slip/cut applied front ears, and alternately rotated back ears, a die cut chassis, and die cut ears.
Figure 88:
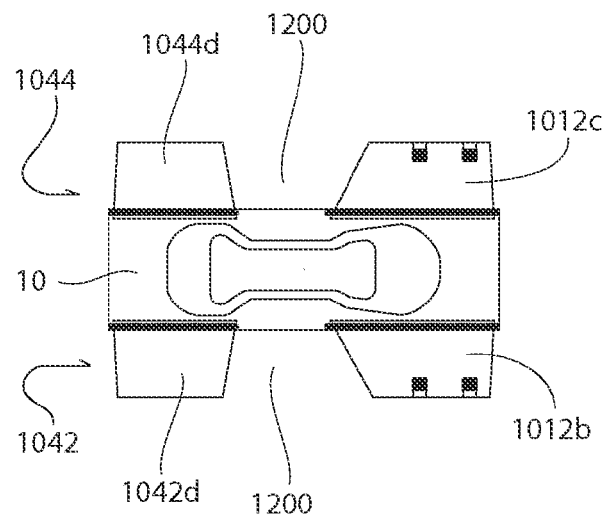
FIG. 88 is a plan view of a product variation showing alternately rotated applied front ears, and alternately rotated back ears.

Referring to FIG. 87, the embodiment of FIG. 86 is shown with the additional product feature of chips 1230 having been removed from both the front ear and back ear portions of the product, for instance using the severing and chip removal pattern of FIG. 76. Referring to FIG. 88, a plan view of a product variation showing alternately rotated applied front ears, and alternately rotated back ears, using the previously described techniques, for instance the technique used to construct the product configuration shown in FIG. 28 is shown, with the exception that no extension panel is present in the embodiment shown in FIG. 88.

Figure 89:
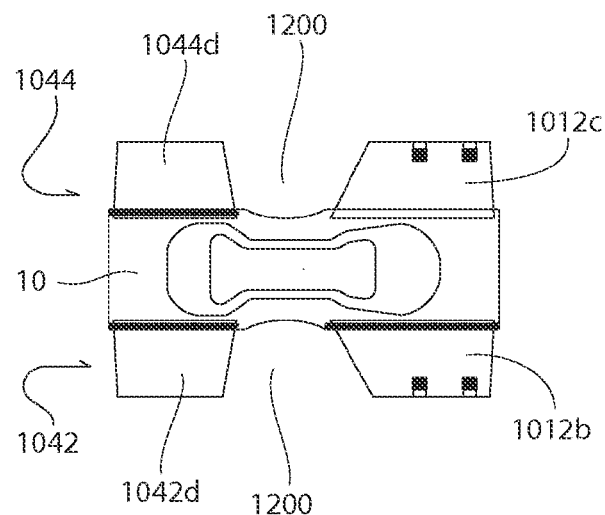
FIG. 89 is a plan view of a product variation showing alternately rotated applied front ears, and alternately rotated back ears, and a die cut chassis.
Figure 90:
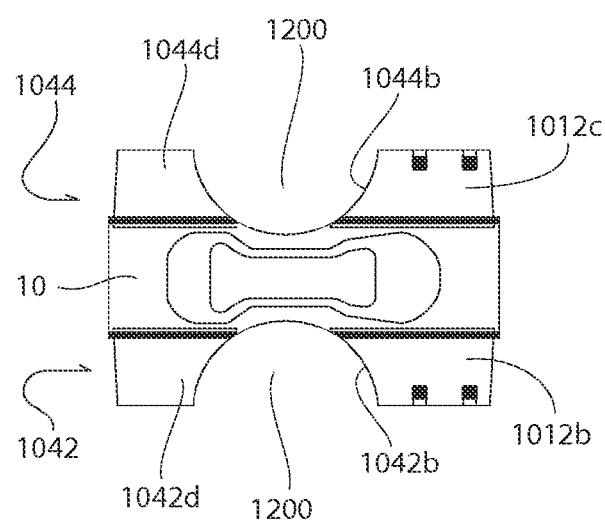
FIG. 90 is a plan view of a product variation showing alternately rotated applied front ears, and alternately rotated back ears, a die cut chassis, and die cut ears.

Referring to FIG. 89, the embodiment of FIG. 88 is shown, with the additional product feature of leg portions 1200*a* and 1200*b* of the chassis removed from the chassis, to fit around the leg of a wearer Referring to FIG. 90, the embodiment of FIG. 89 is shown with the additional product feature of chips 1230 having been removed from both the front ear and back ear portions of the product, for instance using the severing and chip removal pattern of FIG. 76.

Figure 91:
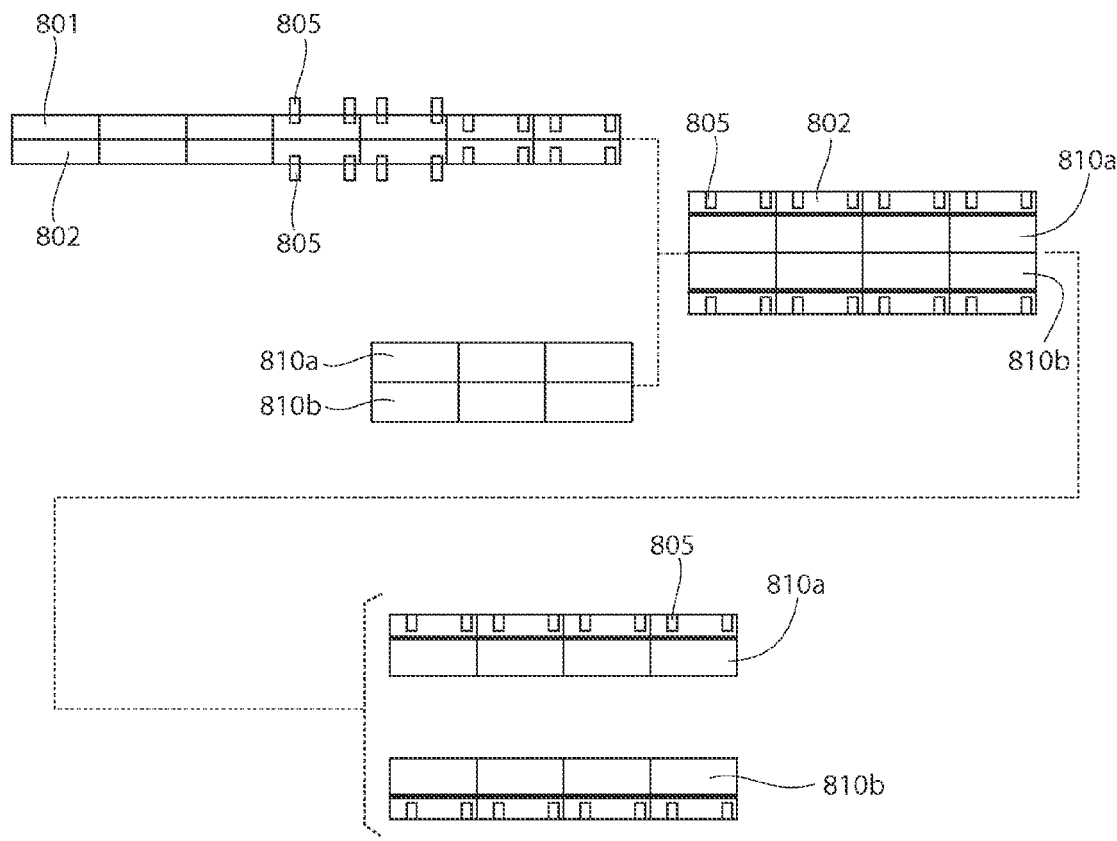
FIG. 91 is a schematic plan view of an extension panel nonwoven web, receiving tapes, which are folded. A stretch laminate web is provided, which receives slit and spread extension panels of the extension panel nonwoven, and the combination stretch laminate web, coupled with the extension panels holding folded ears, is itself slit and spread.

Referring to FIG. 91 a schematic plan view of an extension panel nonwoven web 801/802 is shown, receiving tapes 805, which are then folded down over the extension panel nonwoven web 801/802. A stretch laminate web 810*a*/810*b* is provided, which receives slit and spread extension panels 801/802 of the extension panel nonwoven, and the combination stretch laminate web 810*a*/810*b* coupled with the extension panels 801/802 holding folded ears 805, is itself slit and spread.

Figure 92:
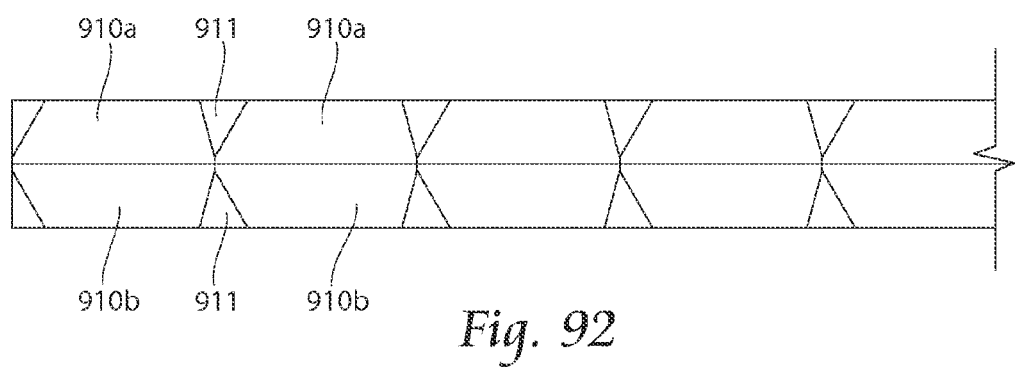
FIG. 92 is a side panel nonwoven web with chip portions.
Figure 93:
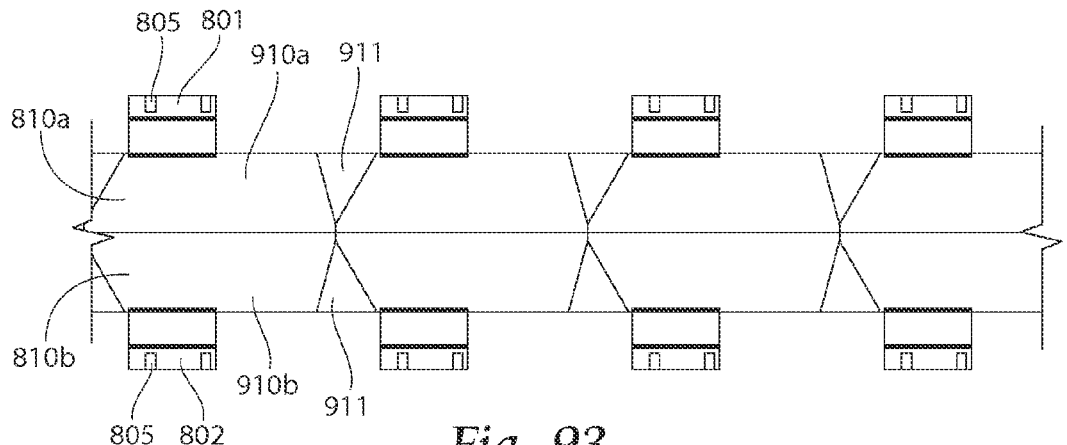
FIG. 93 is the side panel nonwoven web having received (preferably by slip/cut techniques) discrete pieces of the slit and spread combination stretch laminate web, coupled with the extension panels holding folded ears.
Figure 94:
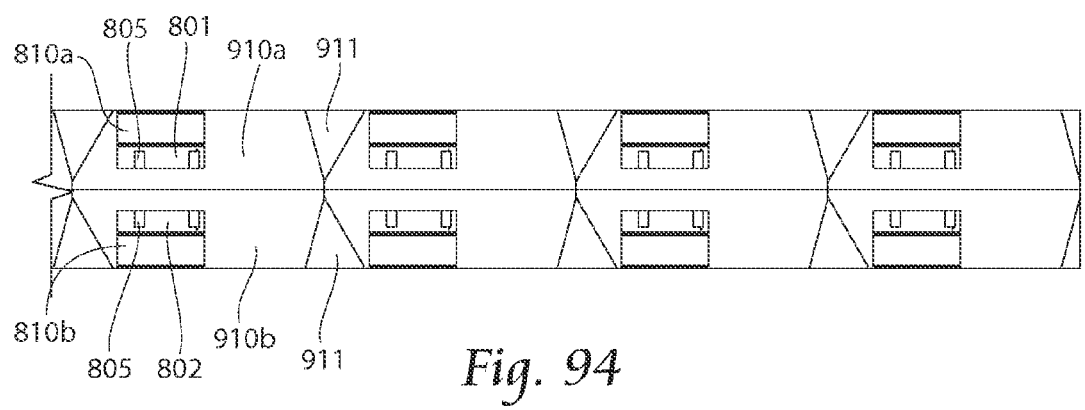
FIG. 94 is the side panel nonwoven web having received (preferably by slip/cut techniques) discrete pieces of the slit and spread combination stretch laminate web, coupled with the extension panels holding folded ears, with the discrete pieces of the slit and spread combination stretch laminate web, coupled with the extension panels holding folded ears folded over.
Figure 95:
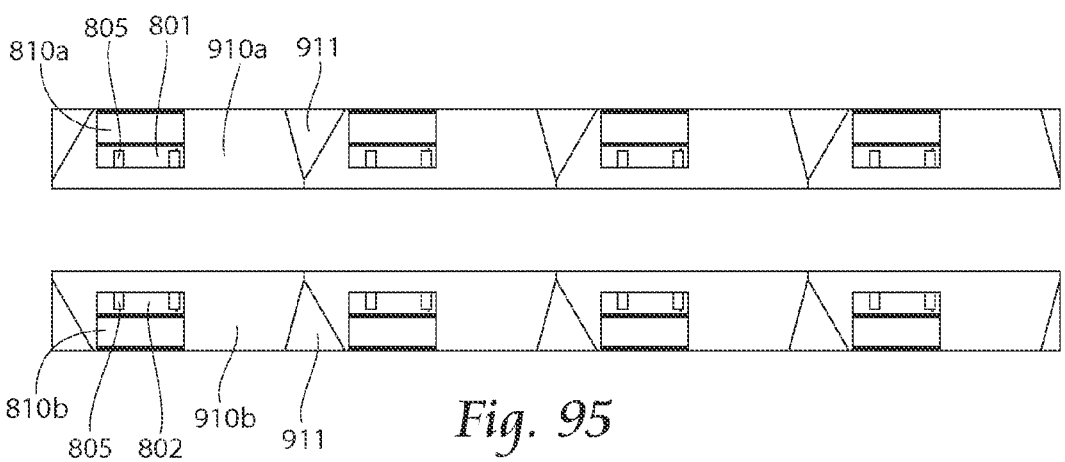
FIG. 95 shows the components of FIG. 94 slit and spread.
Figure 99:
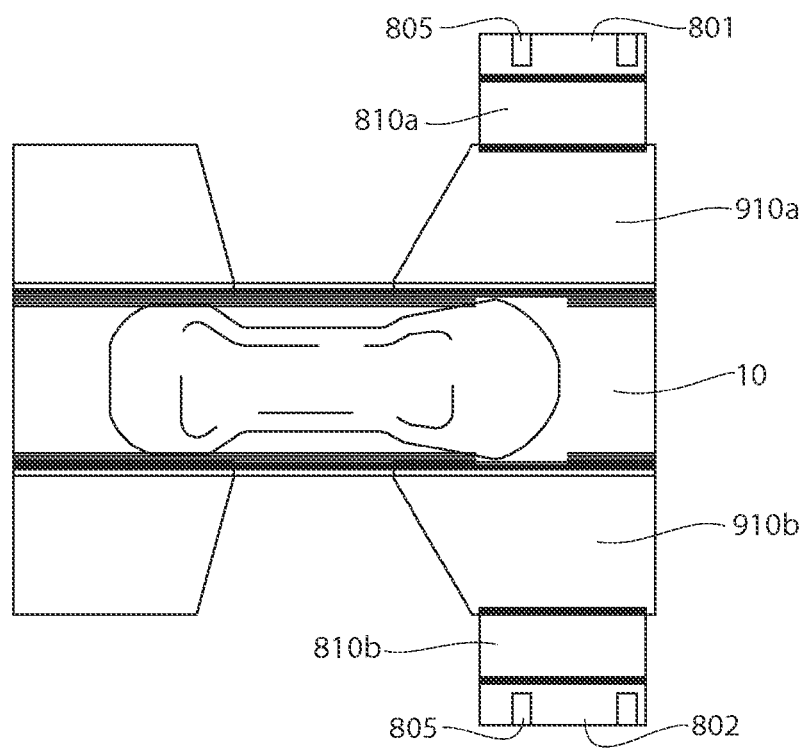
FIG. 99 shows a plan view of a finished diaper in a laid open position.

Referring now to FIG. 92, side panel nonwoven web is provided with chip portions 911 for later removal. As shown in FIG. 93, the side panel nonwoven web 910A/910B receives (preferably by slip/cut techniques) discrete pieces of the combination stretch laminate web 810*a*/810*b* coupled with the extension panels 801/802 holding folded ears 805. The combination stretch laminate web 810*a*/810*b* coupled with the extension panels 801/802 holding folded ears 805 is then folded over, as shown in FIG. 94, slit and spread as shown in FIG. 95. Next, chips 911 are removed as shown in FIG. 96. Next, discrete combination stretch laminate web 810*a*/810*b* coupled with the extension panels 801/802 holding folded ears 805 carried by the nonwoven web 910A/910B portions are then severed, and joined with a chassis web as shown in FIG. 98. Next, a die cut unit is used to sever discrete diapers as shown in FIG. 99 which shows a plan view of a finished diaper in a laid open position. The severing takes place between desired portions of the combination stretch laminate web 810*a*/810*b* coupled with the extension panels 801/802 holding folded ears 805, carried by carried by the nonwoven web 910A/910B to form a discrete product.

Figure 100:
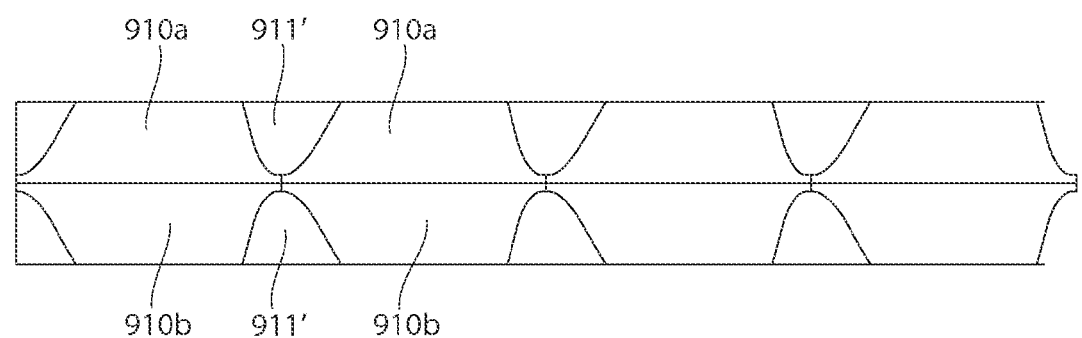
FIG. 100 shows an alternate chip pattern for use in the construction of FIGS. 91-99.

Referring now to FIG. 100, an alternate chip pattern 911' is shown, for use in the construction of FIGS. 91-99. This shape allows for greater flexibility in the positioning of the sever to form discrete diapers.

Figure 101:
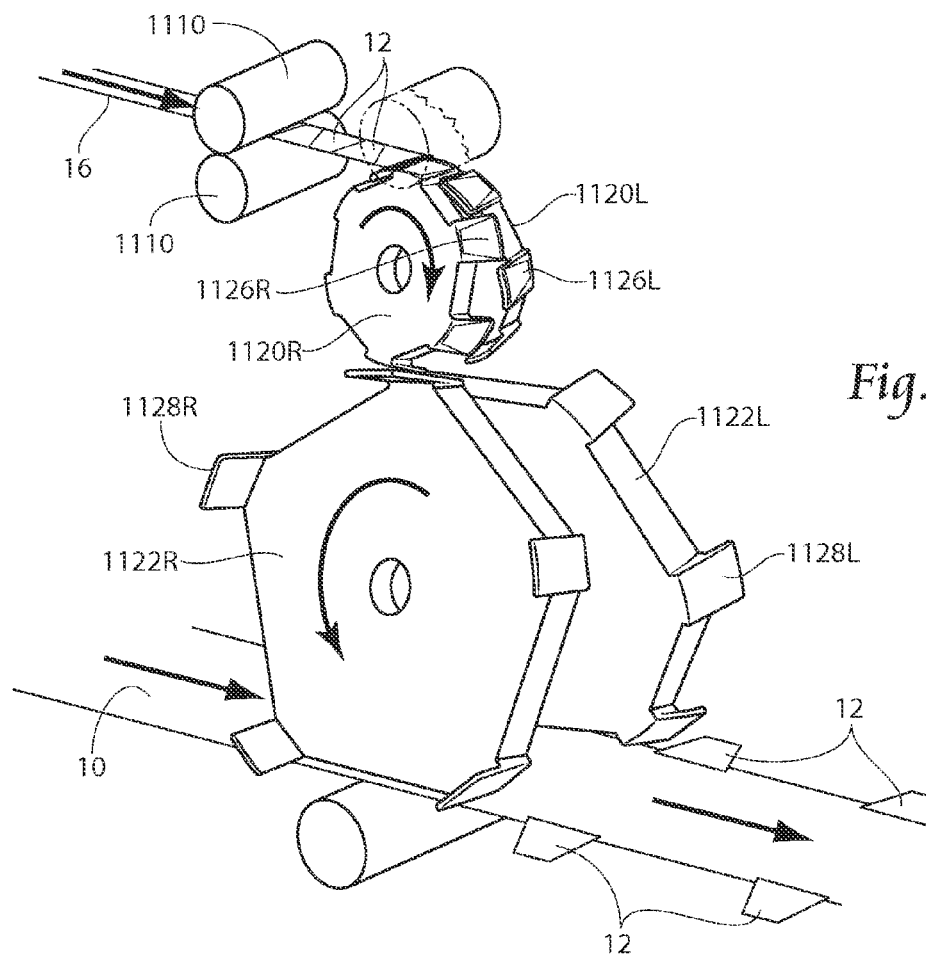
FIG. 101 shows an apparatus for placing ears on a chassis web, with zero waste, from a single incoming lane.

Referring now to FIG. 101, an apparatus for placing ears 12 on a chassis web 10, with zero waste, from a single incoming lane 16 is shown. This embodiment is useful if it is desired to avoid rotation of the ears as previously described, about two different rotational axes.

Figure 104:
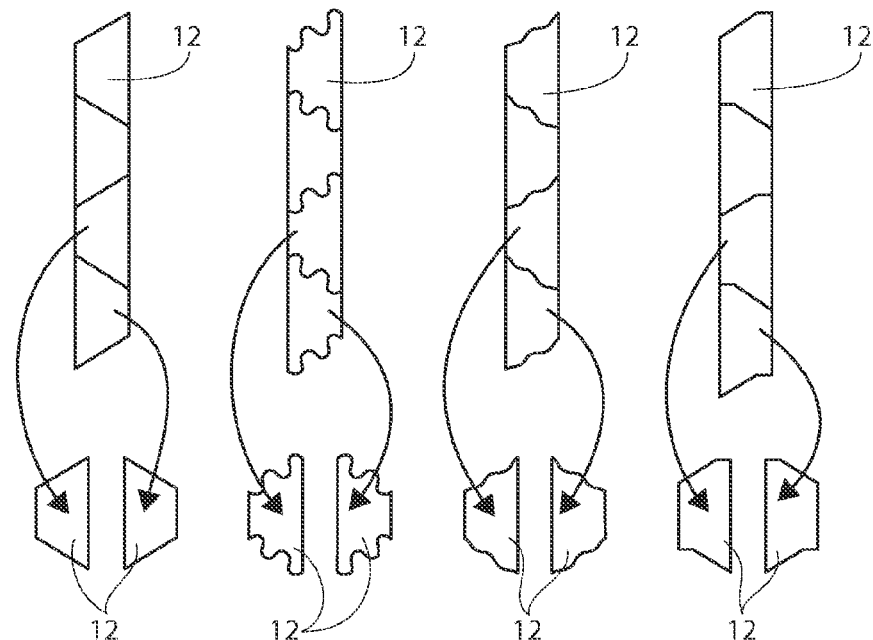
FIG. 104 are additional symmetrical ear patterns that can be formed with a single incoming web.

The apparatus provides for synchronized anvil/die combination 1110 to sever the incoming web 16 into desired preferably symmetrical ear shapes 12, such as those shown in FIGS. 7A-7E, or shown in FIG. 104. A canted right and a canted left ear rotational and spreading assembly 1120R and 1120L acquires individually cut ears 12 (for instance, by slip/cut techniques), which are carried for instance on pucks 1126R and 1126L, for instance of the vacuum assisted variety shown as pucks 234 on FIGS. 10*a* and 10B. The canted spreading assemblies provide for cross machine direction displacement of ears 12 so that ears can be simultaneously spread and accelerated to be placed as desired, with ear 12 rotation about only a single axis, the axis rotating canted right and the axis rotating a canted left ear rotational and spreading assembly 1120R and 1120L, but canted pucks, relative to the axis of rotation, allows correct orientation when picking up and depositing ears 12.

In a preferred embodiment of this apparatus, there is no axial rotation of ears 12 so that the shape of the ear 12 can be provided for symmetrical with respect to right and left ears, with zero incoming web wasted.

The rotational and spreading assemblies 1120R and 1120L are preferably provided with vacuum in order to maintain the ears 12 during rotation and then release the ears onto secondary right rotational assembly 1122R and secondary left rotational assembly 1122L which further spread the ears 12, and further speed up the ears 12 to a depositional velocity of the chassis web 10. Preferably, the secondary right rotational assembly 1122R and secondary left rotational assembly 1122L also rotate ears 12 about a rotational axis, but it is not required to rotate the ears about the axis of the ears. The secondary right rotational assembly 1122R and secondary left rotational assembly 1122L are also preferably vacuum assisted to control ears 12, and likewise contain pucks 1128R and 1128L, again similar to the pucks 234 of FIGS. 10*a* and 10B.

The right rotational assembly 1120R will spread the right ears and speed up the right ears from the incoming velocity to a depositional velocity of the chassis web 10. The left rotational assembly 1120L will spread the left ears and speed up the left ears from the incoming velocity to a depositional velocity of the chassis web 10. It is noted that the left or right ears could be provided in a line vertically spaced from its intended deposition point, and then just one of the other of the left or right ears would require cross-machine direction displacement for deposition.

Figure 102:
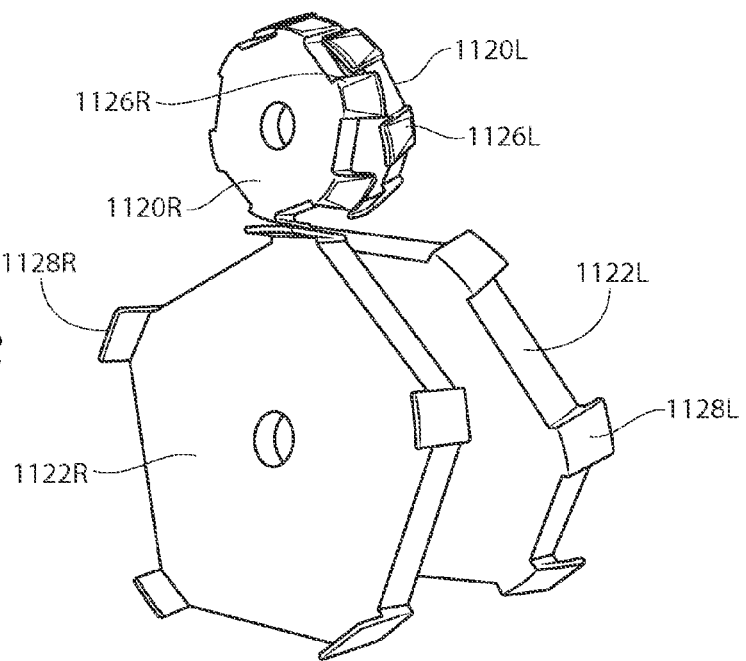
FIG. 102 is a side perspective view of the embodiment shown in FIG. 101.
Figure 103:
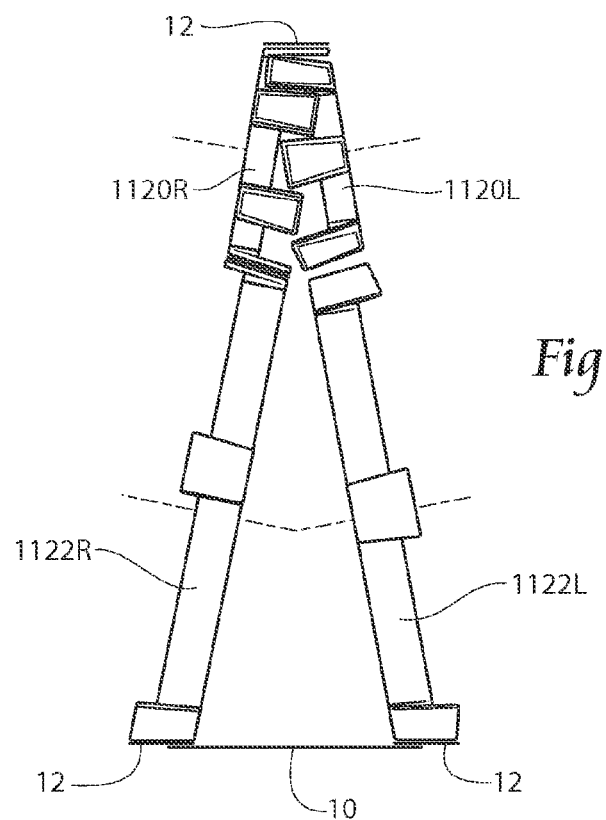
FIG. 103 is a side view of the embodiment shown in FIG. 101.

As can be seen from the side perspective view of FIGS. 102 and 103, the embodiment shown in FIG. 101; the pucks 1126L and 1126L are nested such that they pick up ears 12 coming in sequence. Also preferably, the pucks are canted at an angle relative to their rotation, such that the pick up points and deposition points of the ears 12 are relatively horizontal relative to the machine direction. The pucks 1126L and 1126L match up with rotating pucks 1128R and 1128L respectively, to deposit the ears prior to deposition on chassis web 10.

A small mismatch in speeds is preferred between the pucks 1128R and 1128L respectively is preferable to get the product pickup and placement to match.

Figure 105:
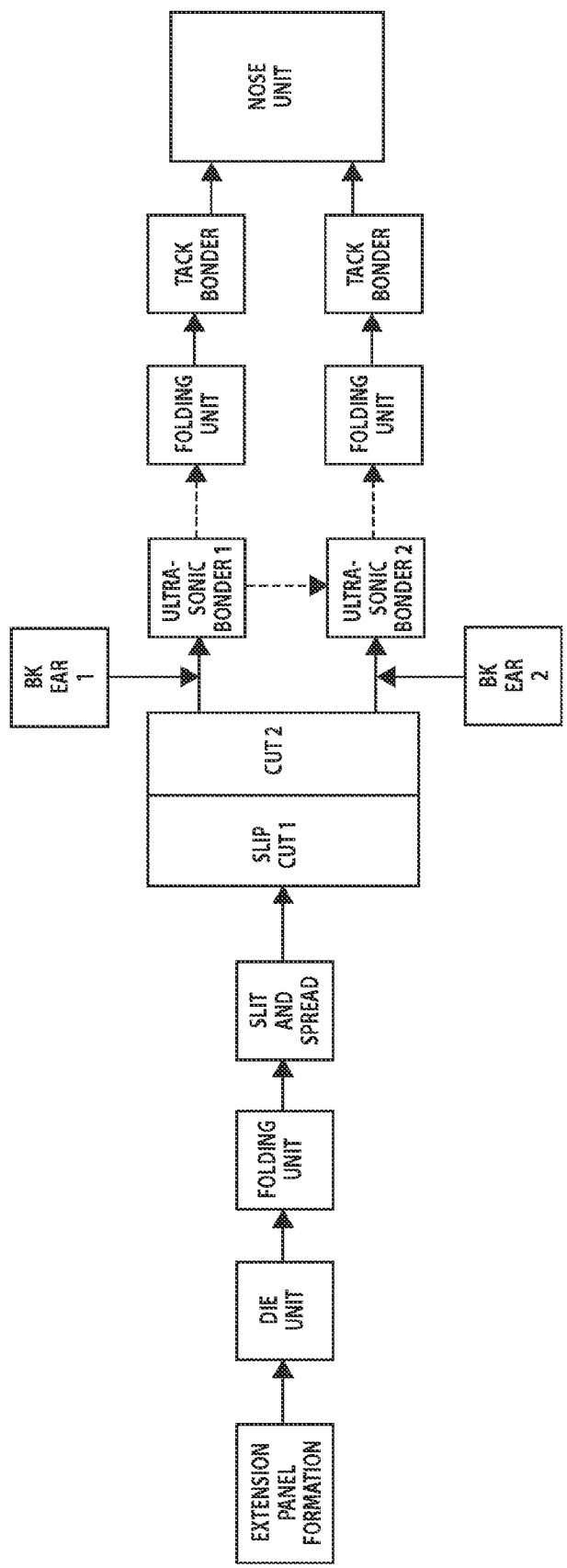
FIG. 105 is a schematic of a process of forming and combining extension panels and ears using a dual cut slip unit.

Referring now to FIG. 105 a schematic of a process of forming and combining extension panels and ears using a dual cut slip unit is shown. An extension panel is formed and passes to a die unit and is optionally folded, slit and spread. The running extension panel web passes to a slip cut unit, is severed by a first knife which cuts the web at a selected speed, such as correlating to two times per product pitch. The anvil, because the unit is preferably a slip cut unit, has the effect of speeding up the web after the web is cut by the first knife.

A second knife then cuts the web a second time, preferably at pitch. This arrangement creates a first gap between pieces having been slip cut, and the pieces having been slip cut are severed in half (preferably) by the second knife cut. The first gap is set when the web speeds up on the knife anvil after the cut by the first knife.

When the severed web portions are transferred from the dual cut slip unit to a dual intermittent ultrasonic bonding anvil roll, incoming ear webs are fed into the system, which are alternately bonded to a first and second incoming ear web, then both lanes are folded, tack bonded and passed to the nested zero waste back ear applicator device, such as that shown in FIG. 8a.

Figure 106:
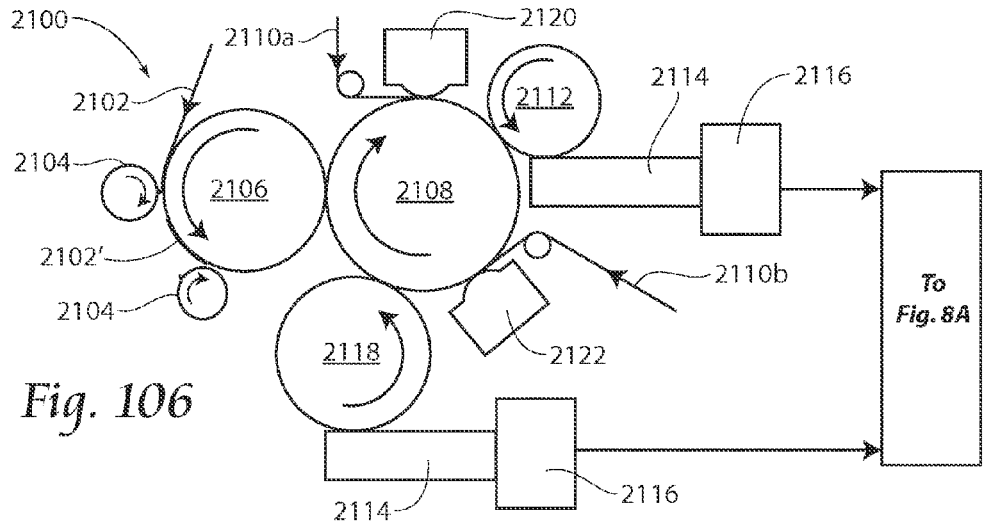
FIG. 106 is a side process view of an apparatus and method of forming and combining extension panels and ears using a dual cut slip unit, and passing the combination to the nested zero waste back ear applicator device, the device having slip cut a first portion from an incoming extension panel web.

Referring now to FIG. 106, a side process view of one side of an apparatus and method of forming and combining extension panels and ears using a dual cut slip unit 2100 is shown. An extension panel web 2102 is fed to a dual slip cut unit with rotating anvil 2106 and rotating knifes 2104. As shown in FIG. 105, the extension panel web 2102 has been previously slit and spread into two, a left side and a right side extension panel web, to create two lanes (see FIG. 112). The same operations will occur to the left and right lanes as described below with respect to web 2102.

Figure 107:
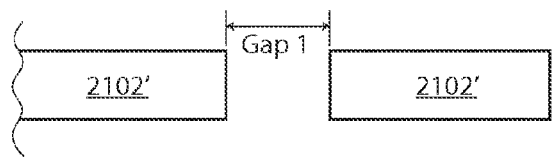
FIG. 107 displays a first gap between two successive first portions of the extension panel web.
Figure 108:
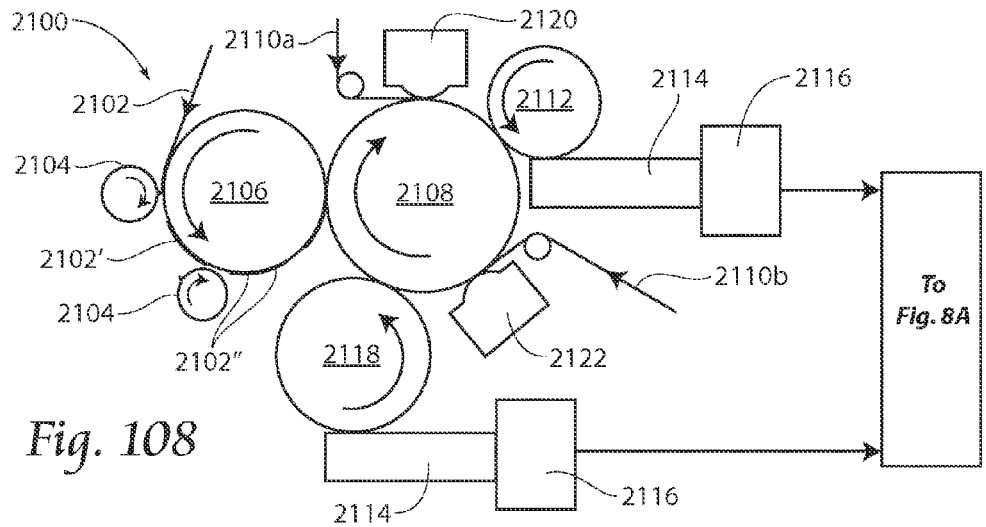
FIG. 108 is a side process view of the device shown in FIG. 106, with a second cut severing the first portion from an incoming extension panel web into two pieces on a knife anvil roll.
Figure 109:
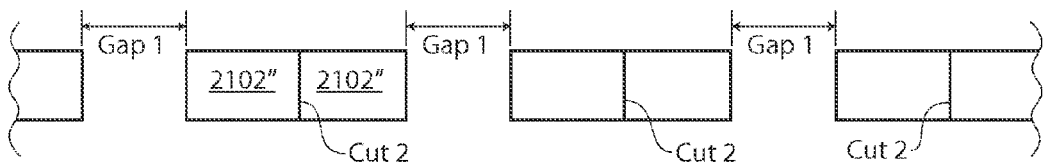
FIG. 109 displays the first gap between two successive first portions of the extension panel web, the discrete portions of the extension panel web being further divided by a second cut prior to being passed to a transfer roll.

A first gap is formed, as shown on FIG. 107, between successive severed pieces 2102' after passing the first knife 2104. Referring now to FIG. 108, severed pieces 2102' are carried by the dual slip cut unit and anvil 2106 by means such as vacuum, to a second knife unit 2104 which subdivides the severed pieces 2102' into subdivided pieces 2102". The subdivided pieces 2102" are past to a transfer roll 2108, which creates a second gap between subdivided pieces and also causes a small increase in the first gap, which occurs to the web when they speed up at the transfer roll 2108 described later.

Figure 110:
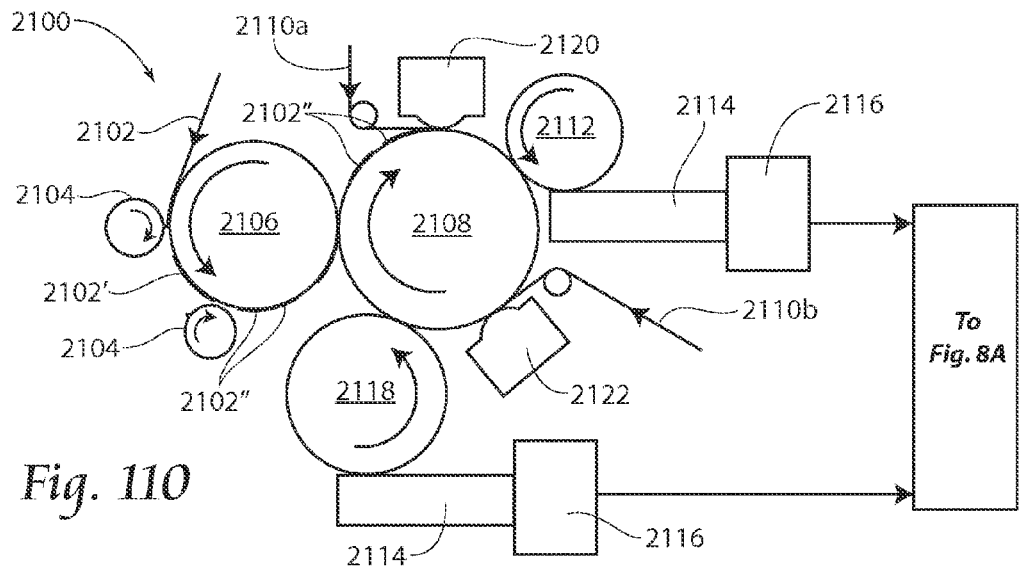
FIG. 110 is a side process view of the device shown in FIG. 108, with a the two discrete pieces of the incoming extension panel entering into a first ultrasonic bonding unit on a transfer roll, which couples every other discrete piece of the incoming extension panel with a first incoming back ear web; and the remaining discrete piece of the incoming extension panel entering a second ultrasonic bonder along with a second incoming back ear web, with both lanes of formed extension panel/back ear webs exiting, being folded and tack bonded, and passed on to the nested zero waste back ear applicator device.

Referring now to FIG. 110, following the cut on the severed pieces 2102', the subdivided pieces 2102" remain carried by the anvil roll 2106 with the first gap and the second cut. Every other of the subdivided pieces are coupled to incoming web 2110a and obtained by roll 2112 and, while remaining pieces are coupled to incoming web 2110b by tack bonder 2112 and passed to transfer roll 2118 (refer to FIG. 112).

Figure 111:
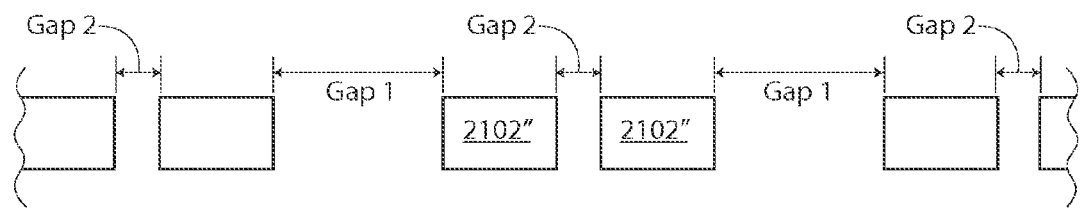
FIG. 111 displays a first gap between two successive first portions of the extension panel web, along with a second gap formed between severed portions of the extension panel web following departure from the knife anvil roll and onto the transfer roll.

Referring now to FIG. 110, the subdivided pieces 2102" are passed to a transfer roll 2108, rotating faster than the anvil roll 2106. Vacuum is turned off the anvil roll 2106 underneath and roughly simultaneously with the approach of a subdivided piece to transfer roll 2108, which allows a leading subdivided piece 2102" to advance in front of a trailing subdivided piece 2102" of a severed piece 2102'. FIG. 111 displays both the first gap between two severed portions 2102', which has been enlarged, and the second gap, between the leading subdivided piece 2102" in front of the trailing subdivided piece 2102". The second gap is set when the materials are passed to a faster moving transfer roll 2108, which both increases the first gap and creates the second gap.

Figure 112:
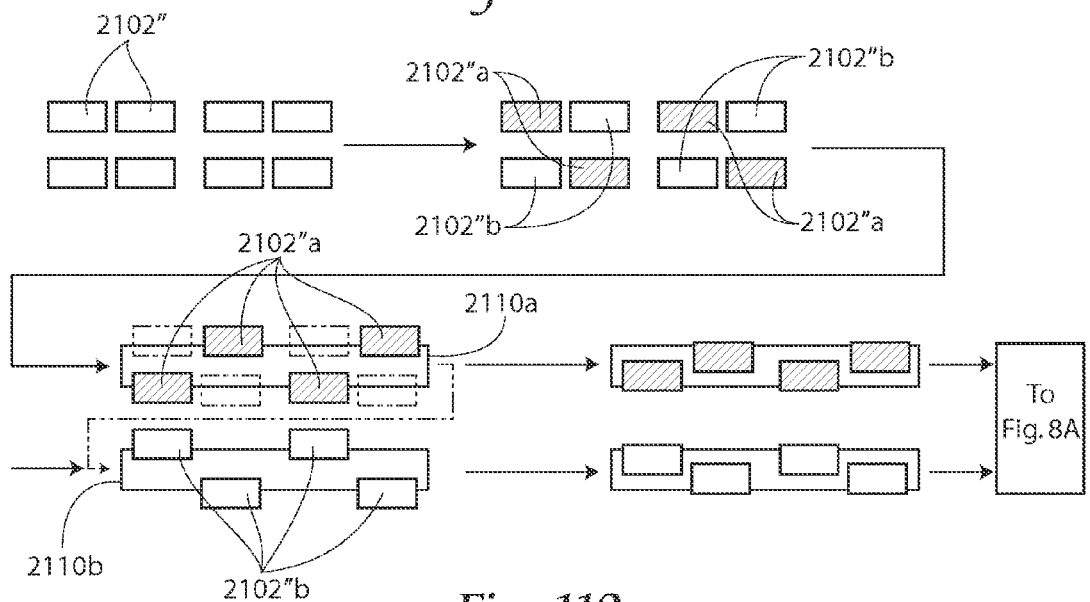
FIG. 112 is a representation of the pieces which are bonded to the first incoming back ear web by the first ultrasonic bonder, and the pieces which are bonded to the second incoming back ear web by the second ultrasonic bonder, both lanes passed to the nested zero waste back ear applicator device.

Referring to FIG. 110 and FIG. 112, a first incoming ear web 2110a is provided to the transfer roll, to bond with the severed pieces 2102"a of FIG. 112, using the first ultrasonic bonding unit 2120. This web is removed from the transfer drum 2108 and passed to transfer roll 2112, folding unit 2114, and tack bonder 2116, and next severed such as shown in FIG. 31, and then passed downstream to the nested zero waste back ear applicator device, such as that shown in FIG. 8a. The drive side ultrasonic bonder in the first set will bond the extension panel onto the ear. Every other extension panel is bonded to the ear. The same application will occur on operator side ultrasonic bonding unit in the first set, in the sequence shown on FIG. 112.

Product pitch is a length of a leading edge of one edge of first product to the leading edge of an adjacent second product in a continuous manufacturing process (or a distance between trailing edges of adjacent products). Product pitch is related to machine speed. For a product of certain length, for instance 500 mm, if the machine speed is 500 meters per minute, then the machine is producing 1000 products per minute.

The severed pieces 2102"b of FIG. 112 are not bonded by the first ultrasonic bonding unit, but instead are still carried by the transfer drum 2108 to be coupled with a second incoming ear web 2110b, and then bonded to that web as shown in FIG. 112 using the second ultrasonic bonding unit 2122. This web is removed from the transfer drum 2108 and passed to transfer roll 2118, folding unit 2114, and tack bonder 2116, and next severed such as shown in FIG. 31, and passed downstream to the nested zero waste back ear applicator device, such as that shown in FIG. 8a. The second web enters the second set of ultrasonic bonding units and bonds the extension panels that were not picked up from the first set of ultrasonic bonding units. The drive and operator side ultrasonic bonding units will intermittently bond the extension panel to the second incoming ear web, as also shown on FIG. 112.

Still referring to FIG. 112, the sequence can be followed. In the first step of the sequence, after the second knife cut on dual slip cut unit 2108, the spacing is set on transfer to unit 2108. In the next step of the sequence, subdivided portions 2102a" are picked up at the first bonder 2120 and coupled to web 2110a. Subdivided portions 2102b" are picked up at the second bonder 2122 and coupled to a web 2110b. In the next step of the sequence the dual webs are spread and folded over on exit, and passed downstream.

Alternatively, two running webs of extension panels and ear webs could be formed, and folded over (not shown). The extension panel can have die cut, c-fold and tack bonding operations performed before entering the dual cut-slip unit 2100.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of severing and spacing a first web of material comprising:
    providing a first web of material at a first speed;
    severing said first web to create a first and a second portion of said first web;
    providing said first and second portions of said first web to an accelerating unit;
    creating a first gap space between said first and second portions of said first web;
    severing said first and second portions of said first web to create a first and a second subdivision of said first portion of said first web; and a first and a second subdivision of said second portion of said first web;
    providing said first and second subdivisions of said first portion of said first web and said first and second subdivisions of said second portion of said first web to an accelerating unit to create a second gap space in a machine direction between said first and second subdivisions of said first portion of said first web and a second gap space between said first and second subdivisions of said second portion of said first web; and
    coupling said first and second subdivisions of said first portion of said first web and said first and second subdivisions of said second portion to a carrier web,
    said method further comprising providing a left lane and a right lane of aid first web of material,
    said method further comprising coupling said second subdivision of said first portion of said left lane of said first web, and said first subdivision of said first portion of said right lane of said first web to a first carrier web; and coupling said first subdivision of said first portion of said left lane of said first web, and said second subdivision of said first portion of said right lane of said first web to a second carrier web.

2. A method according to claim 1, said method further comprising coupling said second subdivision of said second portion of said left lane of said first web, and said first subdivision of said second portion of said right lane of said first web to said first carrier web; and coupling said first subdivision of said second portion of said left lane of said first web, and said second subdivision of said second portion of said right lane of said first web to said second carrier web.

3. A method according to claim 2, said coupling step comprising ultrasonic bonding.

4. A method according to claim 1, the method further comprising passing said first and second webs carrying said portions of said first and second webs to an apparatus for severing said first and second webs and reorienting selected severed portions of said first and second webs.

5. A method according to claim 4, the method further comprising tack bonding said subdivisions to said carrier webs.

6. A method according to claim 1, the method further comprising folding said subdivisions over said carrier webs.

* * * * *